(12) United States Patent
Vidal et al.

(10) Patent No.: US 11,066,395 B2
(45) Date of Patent: Jul. 20, 2021

(54) DIMETHYLAMINOETHANOL SALT OF A GLP-1 RECEPTOR MODULATOR

(71) Applicant: RECEPTOS LLC, New York, NY (US)

(72) Inventors: Ephraim Vidal, Summit, NJ (US); Roger Bakale, Summit, NJ (US); Philip Turnbull, Summit, NJ (US); David Moser, Milton Bridge (GB); Andrew Robbins, Milton Bridge (GB); Craig Grant, Milton Bridge (GB)

(73) Assignee: RECEPTOS LLC, New York, NY (US)

( * ) Notice: Subject to any disclaimer, the term of this patent is extended or adjusted under 35 U.S.C. 154(b) by 0 days.

(21) Appl. No.: 16/337,298

(22) PCT Filed: Sep. 29, 2017

(86) PCT No.: PCT/US2017/054298
§ 371 (c)(1),
(2) Date: Jun. 17, 2019

(87) PCT Pub. No.: WO2018/064476
PCT Pub. Date: Apr. 5, 2018

(65) Prior Publication Data
US 2020/0131164 A1  Apr. 30, 2020

Related U.S. Application Data

(60) Provisional application No. 62/402,565, filed on Sep. 30, 2016.

(51) Int. Cl.
*C07D 409/14* (2006.01)

(52) U.S. Cl.
CPC ........ *C07D 409/14* (2013.01); *C07B 2200/13* (2013.01)

(58) Field of Classification Search
CPC ........ C07D 409/14; A61K 31/506; A61P 3/10
See application file for complete search history.

(56) References Cited

U.S. PATENT DOCUMENTS

2016/0038487 A1\*  2/2016  Boehm ............... A61P 3/08
514/4.9

FOREIGN PATENT DOCUMENTS

WO  2016/015014 A1  1/2016

OTHER PUBLICATIONS

Reid, "Practical Use of Glucagon-Like Peptide-1 Receptor Agonist Therapy in Primary Care", Clinical Diabetes, 31(4), pp. 148-157, (2013).\*

\* cited by examiner

*Primary Examiner* — Deepak R Rao
(74) *Attorney, Agent, or Firm* — Seed IP Law Group LLP

(57) ABSTRACT

Crystalline 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt, and methods related to synthesis and therapeutic use of the same.

16 Claims, 42 Drawing Sheets

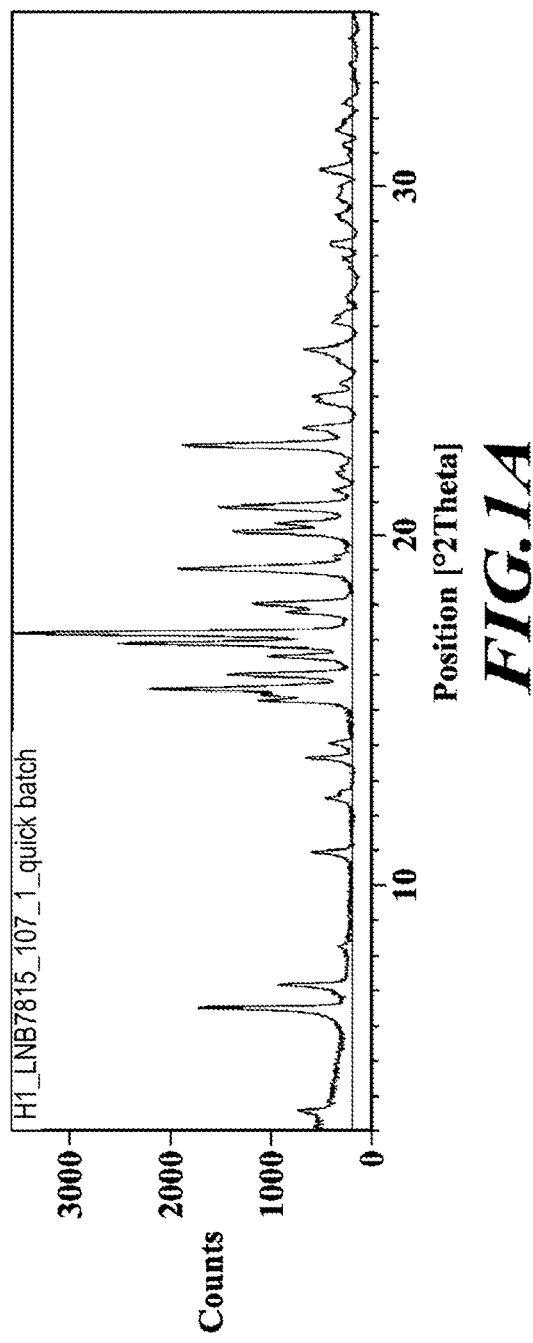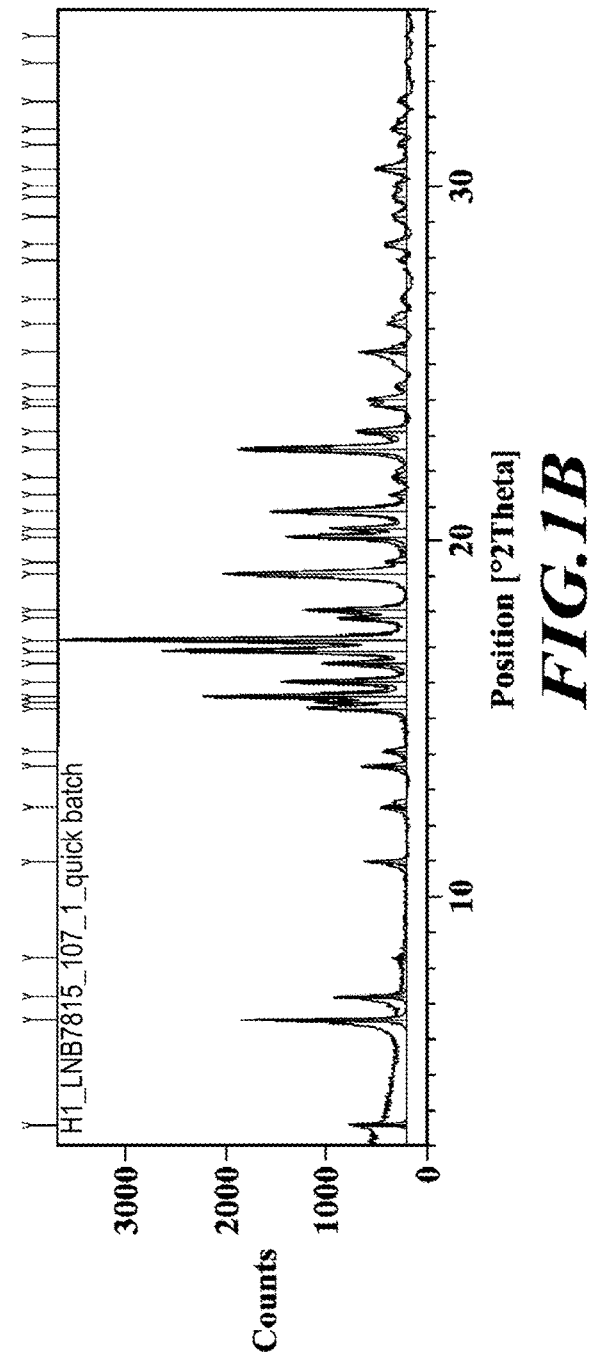

| Pos. [°2Th.] | FWHM [°2Th.] | d-spacing [Å] | Height [cts] | Rel. Int. [%] |
|---|---|---|---|---|
| 3.5749 | 0.0512 | 24.71603 | 525.71 | 15.44 |
| 6.5123 | 0.064 | 13.57276 | 1535.22 | 45.1 |
| 7.1809 | 0.064 | 12.31053 | 705.15 | 20.71 |
| 8.2511 | 0.0768 | 10.71608 | 128.4 | 3.77 |
| 10.9605 | 0.0768 | 8.07243 | 421.83 | 12.39 |
| 12.5108 | 0.064 | 7.0754 | 258.35 | 7.59 |
| 13.6654 | 0.0768 | 6.48004 | 454.7 | 13.36 |
| 14.0801 | 0.1023 | 6.29012 | 220.28 | 6.47 |
| 15.2974 | 0.1023 | 5.79221 | 943.04 | 27.7 |
| 15.4733 | 0.0512 | 5.72675 | 918.88 | 26.99 |
| 15.6291 | 0.0895 | 5.67004 | 2031.74 | 59.68 |
| 16.04 | 0.1023 | 5.52569 | 1209.11 | 35.52 |
| 16.5499 | 0.0768 | 5.35657 | 842.83 | 24.76 |
| 16.9154 | 0.1151 | 5.24165 | 2329.75 | 68.44 |
| 17.2241 | 0.1151 | 5.14838 | 3404.11 | 100 |
| 17.8239 | 0.1023 | 4.97647 | 659.73 | 19.38 |
| 18.0509 | 0.1151 | 4.91439 | 1000.92 | 29.4 |
| 19.0519 | 0.1663 | 4.65839 | 1738.51 | 51.07 |
| 19.3938 | 0.1023 | 4.57704 | 159.94 | 4.7 |
| 20.1216 | 0.0895 | 4.4131 | 1180.32 | 34.67 |
| 20.3544 | 0.0895 | 4.36314 | 727.43 | 21.37 |
| 20.8437 | 0.1535 | 4.26182 | 1313.26 | 38.58 |
| 21.3091 | 0.1023 | 4.16977 | 152.38 | 4.48 |
| 21.7932 | 0.1279 | 4.07823 | 145.32 | 4.27 |
| 22.6012 | 0.1279 | 3.93423 | 1686.5 | 49.54 |
| 23.0898 | 0.1407 | 3.85206 | 484.3 | 14.23 |
| 23.8095 | 0.1023 | 3.73724 | 301.08 | 8.84 |
| 23.9869 | 0.1279 | 3.71 | 384.03 | 11.28 |
| 24.3639 | 0.1279 | 3.65344 | 115.04 | 3.38 |
| 25.3279 | 0.0768 | 3.51653 | 454.54 | 13.35 |
| 26.1168 | 0.1279 | 3.41206 | 186.53 | 5.48 |
| 26.8099 | 0.2558 | 3.32541 | 47.44 | 1.39 |
| 27.916 | 0.1023 | 3.19611 | 67.56 | 1.98 |
| 28.3637 | 0.1791 | 3.14668 | 213.4 | 6.27 |
| 29.1341 | 0.2558 | 3.0652 | 130.45 | 3.83 |
| 29.7 | 0.2047 | 3.00807 | 135.46 | 3.98 |
| 30.0261 | 0.1535 | 2.97615 | 103.54 | 3.04 |
| 30.4801 | 0.2047 | 2.93284 | 287.73 | 8.45 |
| 31.1803 | 0.1535 | 2.86856 | 77.19 | 2.27 |
| 31.6094 | 0.1791 | 2.83059 | 152.04 | 4.47 |
| 32.3889 | 0.1791 | 2.76422 | 80.27 | 2.36 |
| 33.4782 | 0.1535 | 2.67673 | 13.01 | 0.38 |
| 34.2177 | 0.1535 | 2.62056 | 0.19 | 0.01 |

*FIG.1C*

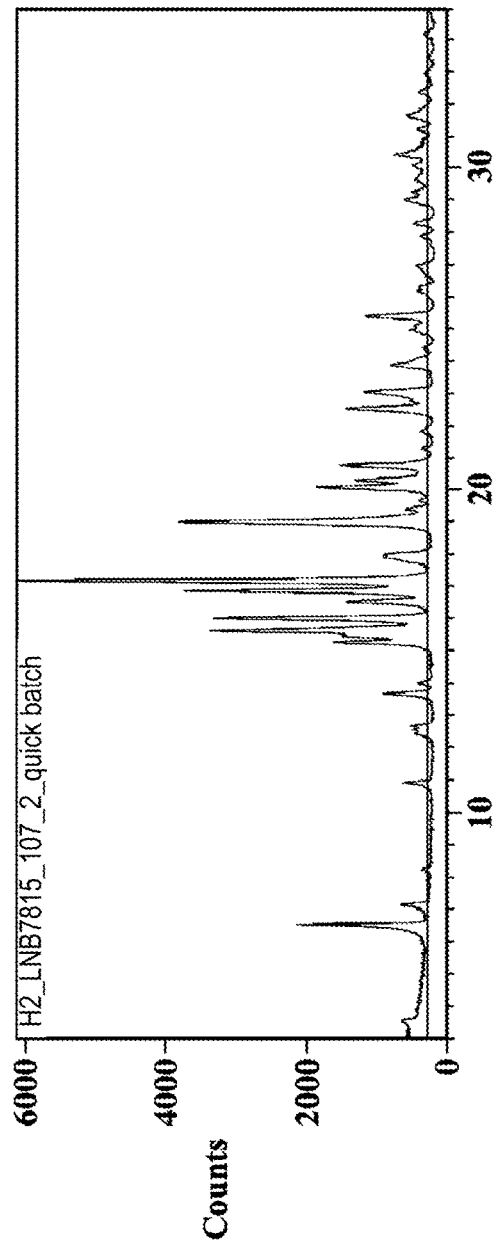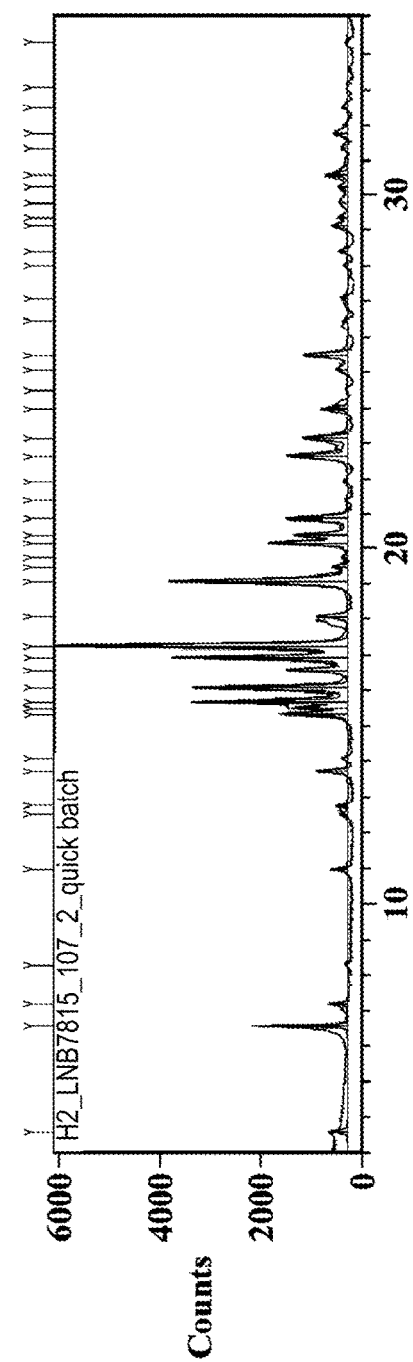

| Pos. [°2Th.] | FWHM [°2Th.] | d-spacing [Å] | Height [cts] | Rel. Int. [%] |
|---|---|---|---|---|
| 3.5656 | 0.1023 | 24.78075 | 354.91 | 6.05 |
| 6.5287 | 0.0512 | 13.53878 | 1846.95 | 31.47 |
| 7.1558 | 0.064 | 12.35371 | 391.36 | 6.67 |
| 8.262 | 0.0768 | 10.70192 | 53.41 | 0.91 |
| 10.9491 | 0.0768 | 8.08081 | 329.06 | 5.61 |
| 12.4831 | 0.0768 | 7.09103 | 173.82 | 2.96 |
| 12.7151 | 0.064 | 6.96216 | 235.21 | 4.01 |
| 13.6959 | 0.0895 | 6.46569 | 633.82 | 10.8 |
| 14.0491 | 0.0768 | 6.30393 | 132.89 | 2.26 |
| 15.2957 | 0.0895 | 5.79285 | 1329.25 | 22.65 |
| 15.4732 | 0.0512 | 5.72681 | 1147.77 | 19.56 |
| 15.6448 | 0.0768 | 5.66438 | 3114.44 | 53.07 |
| 16.048 | 0.1023 | 5.52293 | 3050.99 | 51.99 |
| 16.5551 | 0.1151 | 5.35491 | 1152.79 | 19.64 |
| 16.9087 | 0.0895 | 5.24371 | 3504.98 | 59.72 |
| 17.2236 | 0.1023 | 5.14853 | 5868.83 | 100 |
| 18.0339 | 0.1023 | 4.91899 | 627.33 | 10.69 |
| 19.031 | 0.1151 | 4.66345 | 3574.93 | 60.91 |
| 19.4428 | 0.1151 | 4.5656 | 286.21 | 4.88 |
| 19.6964 | 0.1023 | 4.50738 | 115.64 | 1.97 |
| 20.1139 | 0.1151 | 4.41476 | 1578.41 | 26.89 |
| 20.3307 | 0.1023 | 4.36817 | 1034.28 | 17.62 |
| 20.8018 | 0.1151 | 4.27031 | 1237.7 | 21.09 |
| 21.3068 | 0.1023 | 4.17023 | 61.29 | 1.04 |
| 21.8343 | 0.1023 | 4.07064 | 99.2 | 1.69 |
| 22.553 | 0.1663 | 3.94252 | 1163.3 | 19.82 |
| 23.0552 | 0.1279 | 3.85777 | 897 | 15.28 |
| 23.8981 | 0.064 | 3.72359 | 492.25 | 8.39 |
| 24.4343 | 0.1279 | 3.64307 | 44.74 | 0.76 |
| 24.9846 | 0.1535 | 3.56406 | 213.45 | 3.64 |
| 25.4052 | 0.1407 | 3.50601 | 870.69 | 14.84 |
| 26.3663 | 0.0768 | 3.38034 | 107.38 | 1.83 |
| 26.9839 | 0.1279 | 3.30437 | 131.44 | 2.24 |
| 27.9212 | 0.1279 | 3.19554 | 84.67 | 1.44 |
| 28.3176 | 0.0895 | 3.15169 | 196.1 | 3.34 |
| 29.0353 | 0.1279 | 3.0754 | 316.66 | 5.4 |
| 29.2749 | 0.0768 | 3.05078 | 212.73 | 3.62 |
| 29.6879 | 0.2303 | 3.00927 | 172.04 | 2.93 |
| 30.1121 | 0.1279 | 2.96784 | 202.17 | 3.44 |
| 30.4486 | 0.0768 | 2.9358 | 429.53 | 7.32 |
| 31.2219 | 0.1535 | 2.86483 | 130.27 | 2.22 |
| 31.6355 | 0.1279 | 2.82832 | 278.06 | 4.74 |
| 32.38 | 0.1023 | 2.76497 | 120.19 | 2.05 |
| 32.943 | 0.2558 | 2.71898 | 11.87 | 0.2 |
| 34.1866 | 0.1791 | 2.62287 | 34.72 | 0.59 |

*FIG.2C*

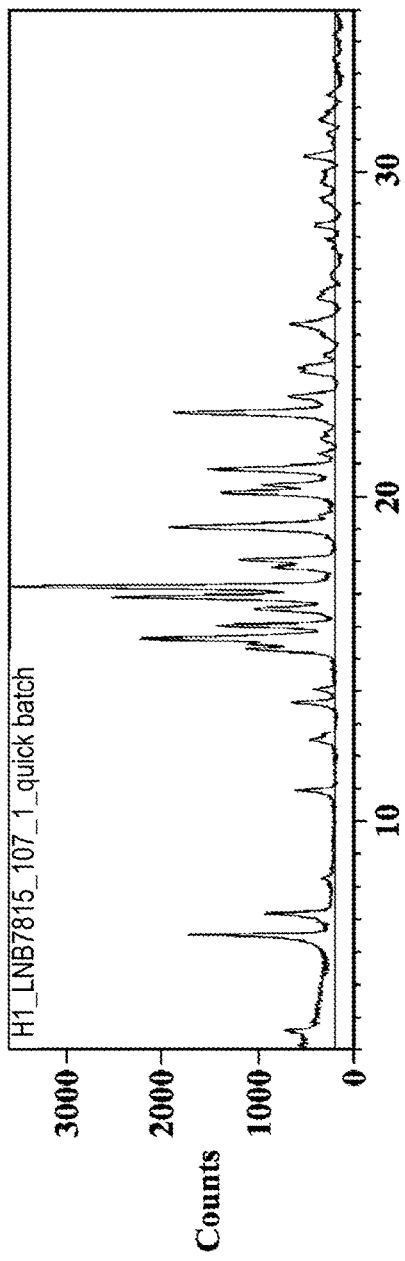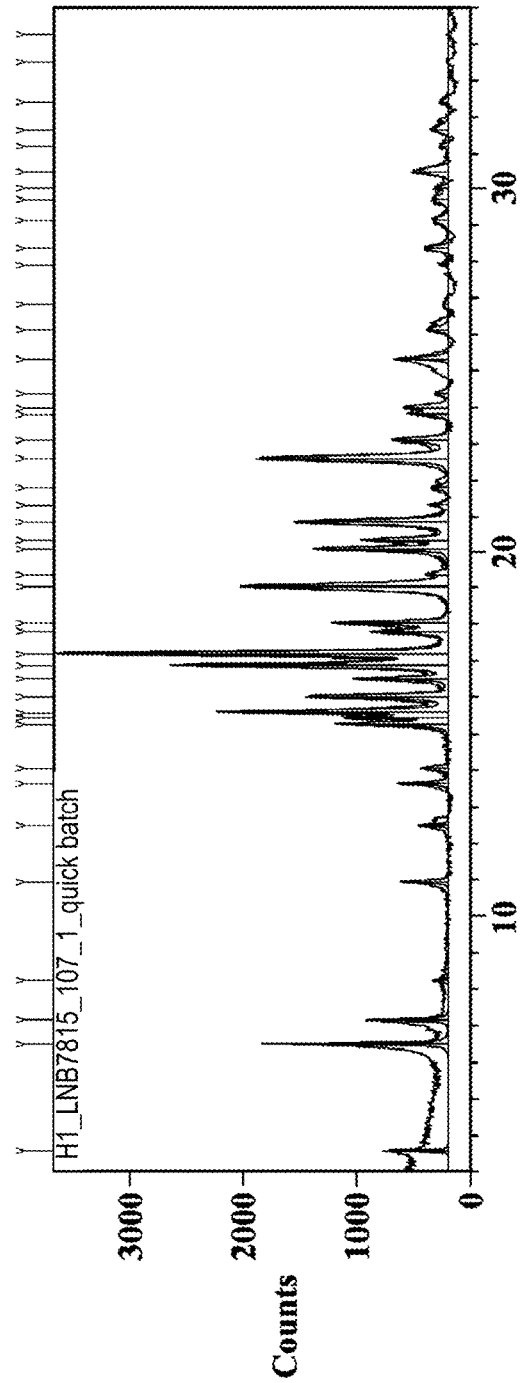

| Pos. [°2Th.] | FWHM [°2Th.] | d-spacing [Å] | Height [cts] | Rel. Int. [%] |
|---|---|---|---|---|
| 3.5749 | 0.0512 | 24.71603 | 525.71 | 15.44 |
| 6.5123 | 0.064 | 13.57276 | 1535.22 | 45.1 |
| 7.1809 | 0.064 | 12.31053 | 705.15 | 20.71 |
| 8.2511 | 0.0768 | 10.71608 | 128.4 | 3.77 |
| 10.9605 | 0.0768 | 8.07243 | 421.83 | 12.39 |
| 12.5108 | 0.064 | 7.0754 | 258.35 | 7.59 |
| 13.6654 | 0.0768 | 6.48004 | 454.7 | 13.36 |
| 14.0801 | 0.1023 | 6.29012 | 220.28 | 6.47 |
| 15.2974 | 0.1023 | 5.79221 | 943.04 | 27.7 |
| 15.4733 | 0.0512 | 5.72675 | 918.88 | 26.99 |
| 15.6291 | 0.0895 | 5.67004 | 2031.74 | 59.68 |
| 16.04 | 0.1023 | 5.52569 | 1209.11 | 35.52 |
| 16.5499 | 0.0768 | 5.35657 | 842.83 | 24.76 |
| 16.9154 | 0.1151 | 5.24165 | 2329.75 | 68.44 |
| 17.2241 | 0.1151 | 5.14838 | 3404.11 | 100 |
| 17.8239 | 0.1023 | 4.97647 | 659.73 | 19.38 |
| 18.0509 | 0.1151 | 4.91439 | 1000.92 | 29.4 |
| 19.0519 | 0.1663 | 4.65839 | 1738.51 | 51.07 |
| 19.3938 | 0.1023 | 4.57704 | 159.94 | 4.7 |
| 20.1216 | 0.0895 | 4.4131 | 1180.32 | 34.67 |
| 20.3544 | 0.0895 | 4.36314 | 727.43 | 21.37 |
| 20.8437 | 0.1535 | 4.26182 | 1313.26 | 38.58 |
| 21.3091 | 0.1023 | 4.16977 | 152.38 | 4.48 |
| 21.7932 | 0.1279 | 4.07823 | 145.32 | 4.27 |
| 22.6012 | 0.1279 | 3.93423 | 1686.5 | 49.54 |
| 23.0898 | 0.1407 | 3.85206 | 484.3 | 14.23 |
| 23.8095 | 0.1023 | 3.73724 | 301.08 | 8.84 |
| 23.9869 | 0.1279 | 3.71 | 384.03 | 11.28 |
| 24.3639 | 0.1279 | 3.65344 | 115.04 | 3.38 |
| 25.3279 | 0.0768 | 3.51653 | 454.54 | 13.35 |
| 26.1168 | 0.1279 | 3.41206 | 186.53 | 5.48 |
| 26.8099 | 0.2558 | 3.32541 | 47.44 | 1.39 |
| 27.916 | 0.1023 | 3.19611 | 67.56 | 1.98 |
| 28.3637 | 0.1791 | 3.14668 | 213.4 | 6.27 |
| 29.1341 | 0.2558 | 3.0652 | 130.45 | 3.83 |
| 29.7 | 0.2047 | 3.00807 | 135.46 | 3.98 |
| 30.0261 | 0.1535 | 2.97615 | 103.54 | 3.04 |
| 30.4801 | 0.2047 | 2.93284 | 287.73 | 8.45 |
| 31.1803 | 0.1535 | 2.86856 | 77.19 | 2.27 |
| 31.6094 | 0.1791 | 2.83059 | 152.04 | 4.47 |
| 32.3889 | 0.1791 | 2.76422 | 80.27 | 2.36 |
| 33.4782 | 0.1535 | 2.67673 | 13.01 | 0.38 |
| 34.2177 | 0.1535 | 2.62056 | 0.19 | 0.01 |

*FIG.3C*

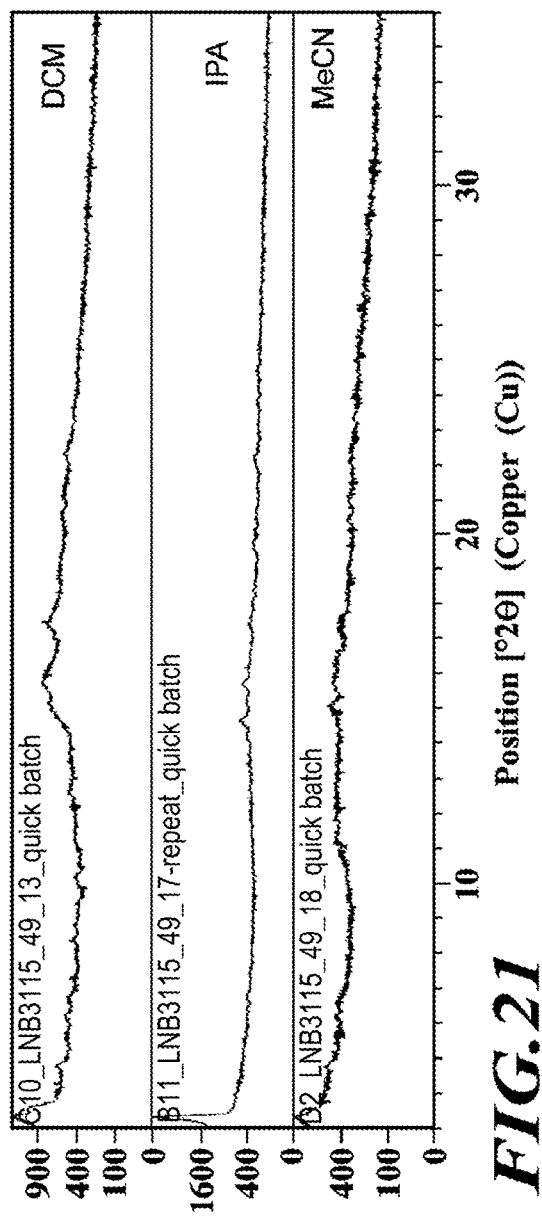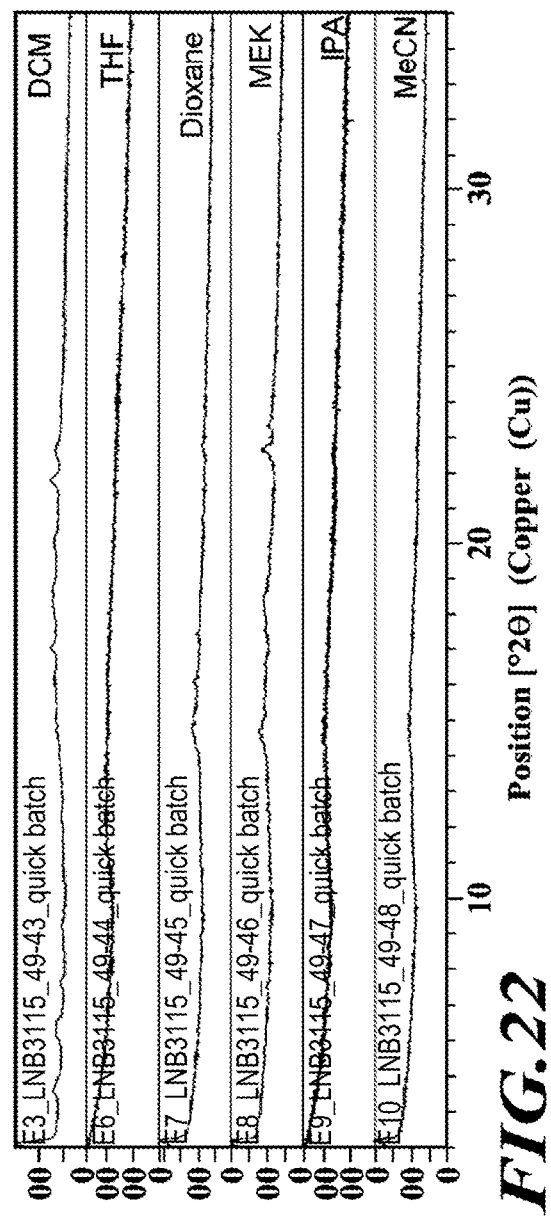
FIG.21
FIG.22

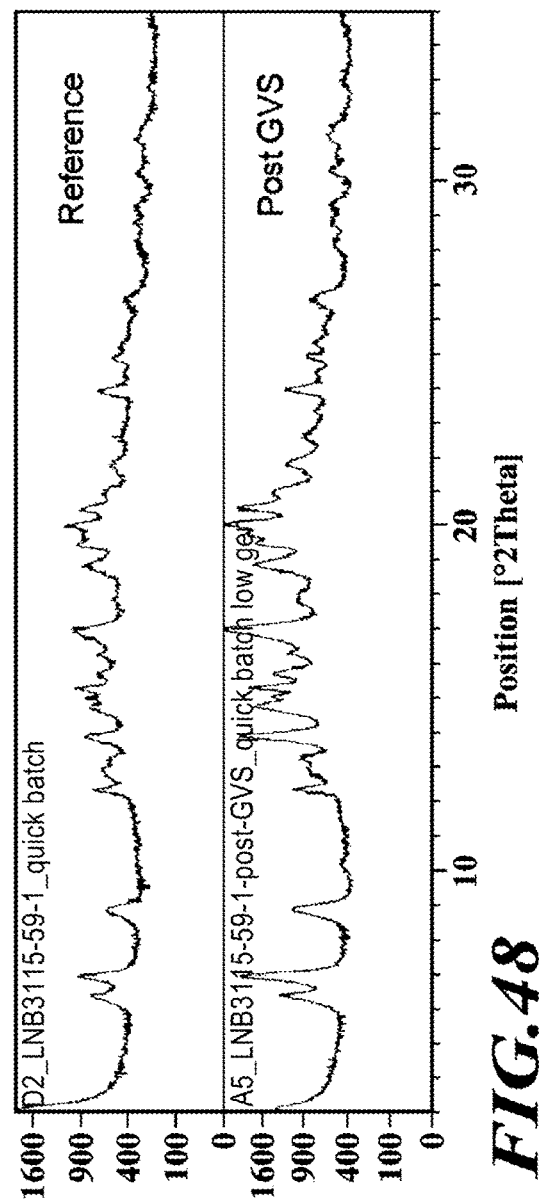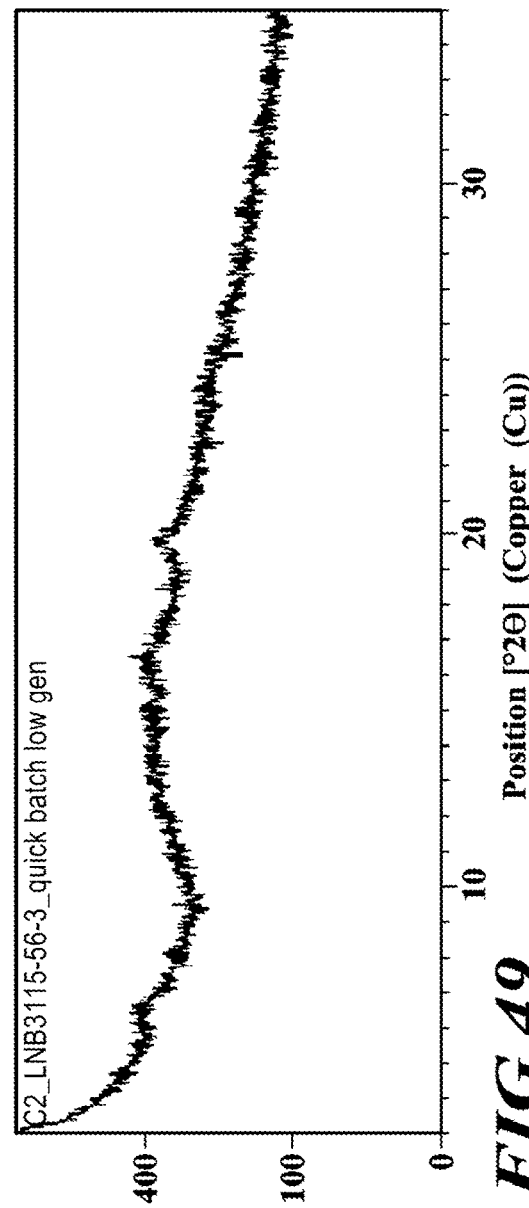
FIG. 48
FIG. 49

DIMETHYLAMINOETHANOL SALT OF A GLP-1 RECEPTOR MODULATOR

FIELD OF THE INVENTION

The invention relates to a dimethylaminoethanol (deanol) salt of a compound that binds the glucagon-like peptide 1 (GLP-1) receptor, as well as to methods of its synthesis and therapeutic use of the same.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain. The initial actions of GLP-1 observed were on the insulin-producing cells of the islets, where it stimulates glucose-dependent insulin secretion. Subsequently, multiple additional antidiabetogenic actions of GLP-1 were discovered including the stimulation of the growth and inhibition of the apoptosis of pancreatic beta cells.

On activation, GLP-1 receptors couple to the α-subunit of G protein, with subsequent activation of adenylate cyclase and increase of cAMP levels, thereby potentiating glucose-stimulated insulin secretion. Therefore, GLP-1 is an attractive therapeutic target to lower blood glucose and preserve the f-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

Globally, it is estimated that 382 million people have diabetes, with type 2 diabetes (T2D) accounting for about 95% of all cases. Absence adequate treatment, T2D increases the risk of heart attacks and strokes, kidney failure, blindness, and amputations. Although many treatment options exist, achieving adequate glycemic control remains challenging. For example, beta-cell function progressively declines, often necessitating treatment intensification over time to maintain glycemic control. Current diabetes treatment guidelines recommend a patient-specific approach to treatment with a goal of achieving glycemic control while minimizing adverse effects, particularly weight gain and hypoglycemia. While lifestyle modifications, weight loss, and metformin are typically considered first-line options, several medication classes are available for use as add-on therapy. To this end, GLP-1 receptor agonists are attractive options for the treatment of T2D because they effectively lower glycated hemoglobin (A1C test) and weight while having a low risk of hypoglycemia.

As a result, the number of GLP-1 receptor agonist has grown over the last decade, with several currently approved for use in use in the US and/or Europe, and with more in development. One promising class of GLP-1 receptor antagonists includes these disclosed in Published PCT WO2016/015014, in particularly Compound No. 76, the structure of which is set forth below:

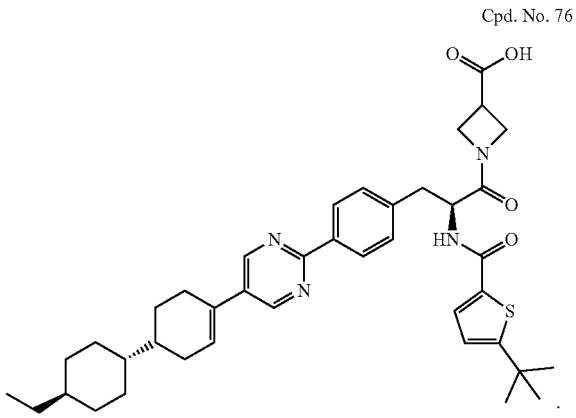 [SMILES: CC[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)CC2)CC1]

Cpd. No. 76

While advances have been made in this field, there remains a need for improved GLP-1 receptor agonists, particularly improved forms of Cpd. No. 76 that exhibit desired crystallinity, solubility and/or thermal behavior, and which overcome challenges to formulation, storage and delivery of the same.

SUMMARY OF THE INVENTION

The present disclosure provides a novel dimethylaminoethanol (deanol) salt of Cpd. No. 76 or an isomer thereof. It has been discovered that the deanol salt of this compound exhibits unexpected and surprising crystallinity, solubility and/or thermal behavior properties.

Cpd. No. 76 contains two chiral centers, and may exist in different isomeric forms (e.g., enantiomers and diastereomers). For purpose of this disclosure, Cpd. No. 76 as the free acid (i.e., 1-(2-(5-(tert-butyl)thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylic acid), absent isomeric designation of chiral centers, will hereinafter be referred to as "RP-101" and has the following structure:

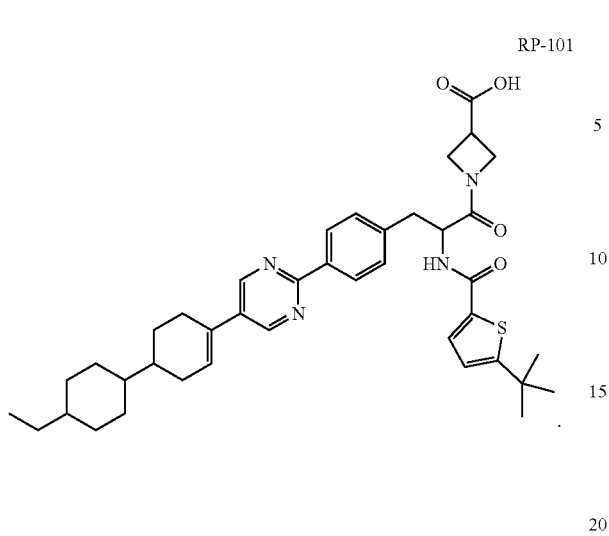

RP-101

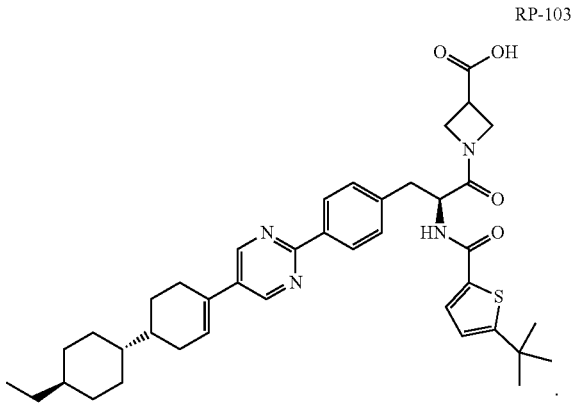 [SMILES: CC[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)CC2)CC1]

RP-103

Unless indicated to the contrary, reference to RP-101 throughout this disclosure is intended to encompass all isomeric forms of the above compound.

In a more specific embodiment of RP-101, the compound is 1-((2S)-2-(5-(tert-butyl)thiophene-2-carboxamido)-3-(4-(5-(4'-ethyl-[1,1'-bi(cyclohexan)]-3-en-4-yl)-pyrimidin-2-yl)phenyl)-propanoyl)azetidine-3-carboxylic acid and has the following structure RP-102:

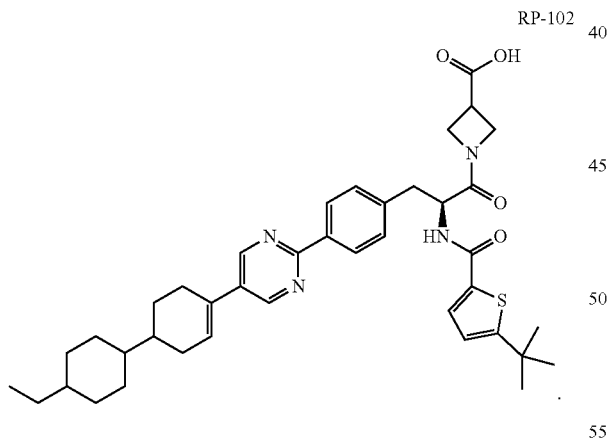

RP-102

In a more specific embodiment, the compound is a substantially diastereomerically pure form of RP-102 and has one of the following structures RP-103 (i.e., 1-((S)-2-(5-(tert-butyl)thiophene-2-carboxamido)-3-(4-(5-((1 S,1'r,4'S)-4'-ethyl-[1,1'-bi(cyclohexan)]-3-en-4-yl)pyrimidin-2-yl) phenyl)propanoyl)azetidine-3-carboxylic acid) and RP-104 (i.e., 1-((S)-2-(5-(tert-butyl)thiophene-2-carboxamido)-3-(4-(5-((1R,1'r,4'R)-4'-ethyl-[1,1'-bi(cyclohexan)]-3-en-4-yl) pyrimidin-2-yl)phenyl)propanoyl)azetidine-3-carboxylic acid), or is a racemic (diastereomeric) mixture of RP-103 and RP-104:

RP-104

Due to the carboxylic acid group, salt forms of RP-101 may be generated upon combination with a counterion (cation). In the context of this disclosure, dimethylaminoethanol (also referred to as "deanol") serves as the counterion ion to RP-101 to provide a deanol salt of RP-101 (i.e., 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)-pyrimidin-2-yl)phenyl)propanoyl)azetidine-3-carboxylate salt), referred to herein as "deanol-RP-101" and having the following structure:

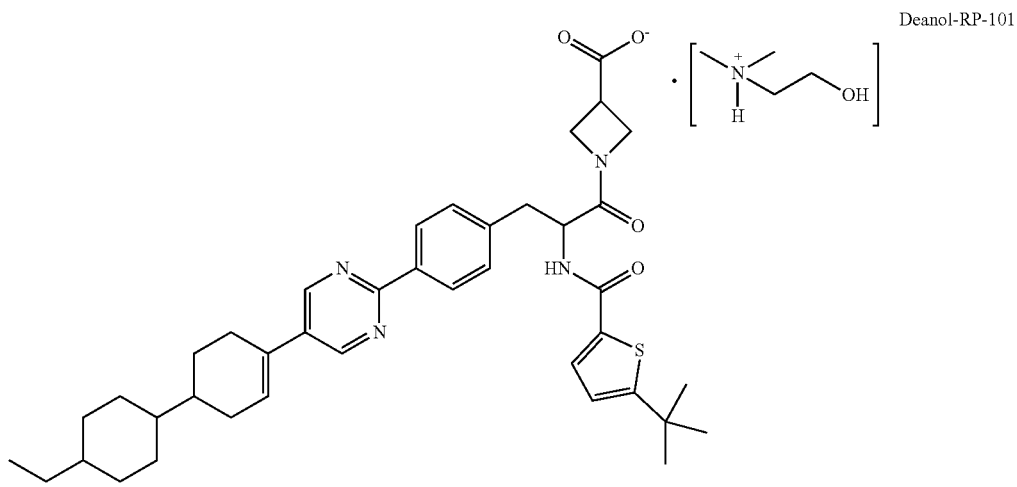

Deanol-RP-101

In a more specific embodiment of deanol-RP-101, the compound is 2-hydroxy-N,N-dimethylethanaminium 1-((2S)-2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)-azetidine-3-carboxylate salt (referred to as "deanol-RP-102") and has the following structure:

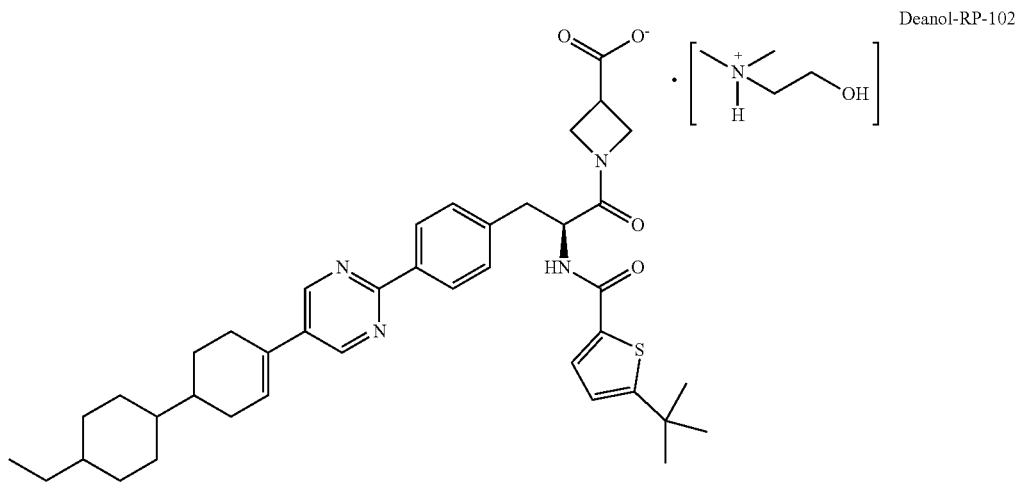

Deanol-RP-102

In more specific embodiments, the compound is a substantially diastereomerically pure form deanol-RP-102 and has one of the following isomeric forms, referred to herein as "deanol-RP-103" (i.e., 2-hydroxy-N,N-dimethylethanaminium 1-((S)-2-(5-(tert-butyl)thiophene-2-carboxamido)-3-(4-(5-((1 S,1'r,4'S)-4'-ethyl-[1,1'-bi(cyclohexan)]-3-en-4-yl)pyrimidin-2-yl)phenyl)propanoyl)-azetidine-3-carboxylate) and "deanol-RP-104" (i.e., 2-hydroxy-N,N-dimethylethanaminium 1-((S)-2-(5-(tert-butyl)thiophene-2-carboxamido)-3-(4-(5-((1R,1'r,4'R)-4'-ethyl-[1,1'-bi(cyclohexan)]-3-en-4-yl)pyrimidin-2-yl)phenyl)-propanoyl)-azetidine-3-carboxylate), or is a racemic (diastereomeric) mixture of deanol-RP-103 and deanol-RP-104:

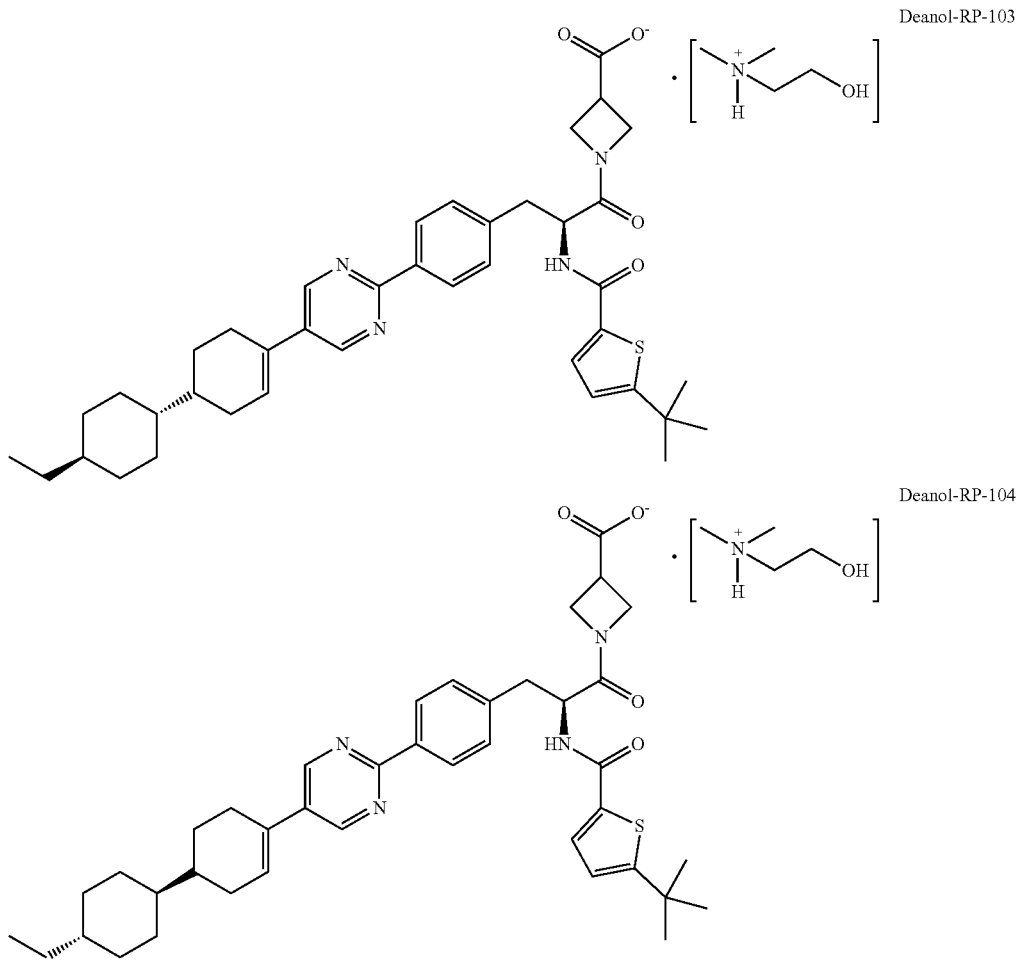

Accordingly, in one embodiment, a crystalline form of deanol-RP-101, deanol-RP-102, deanol-RP-103 or deanol-RP-104 is provided.

In one embodiment, a crystalline form of deanol-RP-101, deanol-RP-102, deanol-RP-103 or deanol-RP-104 may be characterized by x-ray powder defraction (XRPD) wherein distances (d-spacing) and 2θ angles of significant peaks are as set forth in the following detailed description.

In another embodiment, deanol-RP-101, deanol-RP-102, deanol-RP-103 or deanol-RP-104 has a purity in excess of 95% by weight.

In another embodiment, deanol-RP-101, deanol-RP-102, deanol-RP-103 or deanol-RP-104 has a purity in excess of 98% by weight.

In another embodiment, deanol-RP-101 is substantially diastereomerically pure deanol-RP-103, or is substantially diastereomerically pure deanol-RP-104.

In another embodiment, deanol-RP-101 is a diastereomeric mixture of deanol-RP-103 and deanol-RP-104.

In certain embodiments, use of deanol-RP-101, deanol-RP-102, deanol-RP-103 or deanol-RP-104 for the preparation of a medicament is provided.

In certain embodiments, a pharmaceutical composition is provided comprising deanol-RP-101, deanol-RP-102, deanol-RP-103, deanol-RP-104, or a mixture thereof, together with at least one pharmaceutically acceptable carrier, diluent or excipient.

In certain embodiments, a method of activation, potentiation or agonism of a GLP-1 receptor is provided, comprising contacting the receptor with deanol-RP-101, deanol-RP-102, deanol-RP-103, deanol-RP-104, or a mixture thereof, or a pharmaceutical composition as disclosed herein.

In certain embodiments, a method is provided for treatment of a malcondition in a subject for which activation, potentiation or agonism of a GLP-1 receptor is medically indicated, wherein such method comprises administering an effective amount of deanol-RP-101, deanol-RP-102, deanol-RP-103, deanol-RP-104 or a mixture thereof, or a pharmaceutical composition as disclosed herein, to the subject.

In one embodiment the malcondition is type I diabetes, type II diabetes, gestational diabetes, obesity, excessive appetite, insufficient satiety, or metabolic disorder.

In another embodiment, the malcondition is non-alcoholic fatty liver disease (NAFLD) or non-alcoholic steatohepatitis (NASH).

In certain embodiments, methods for synthesis of deanol-RP-101, deanol-RP-102, deanol-RP-103 or deanol-RP-104 are provided, including certain intermediate compounds associated with such methods.

These and other aspects of the present invention will be evident upon reference to the following detailed description and attached drawings.

BRIEF DESCRIPTION OF THE DRAWING

FIG. 1A is an XRPD diffractogram of a diastereomeric mixture of deanol-RP-103 and deanol-RP-104, while FIGS. 1B and 1C identify peaks assignments.

FIG. 2A is an XRPD diffractogram of a substantially diastereomerically pure form of deanol-RP-103, while FIGS. 2B and 2C identify peaks assignments.

FIG. 3A is an XRPD diffractogram of a substantially diastereomerically pure form of deanol-RP-104, while FIGS. 3B and 3C identify peaks assignments.

FIG. 21 shows XRPD diffractograms of the magnesium salt.

FIG. 22 shows XRPD diffractograms of the piperazine salt.

FIG. 48 shows XRPD diffractograms of the dimethylaminoethanol salt pre- and post-GVS profiling.

FIG. 49 shows an XRPD diffractogram of the N-methylglucamine salt.

DETAILED DESCRIPTION OF THE INVENTION

Figure 4:
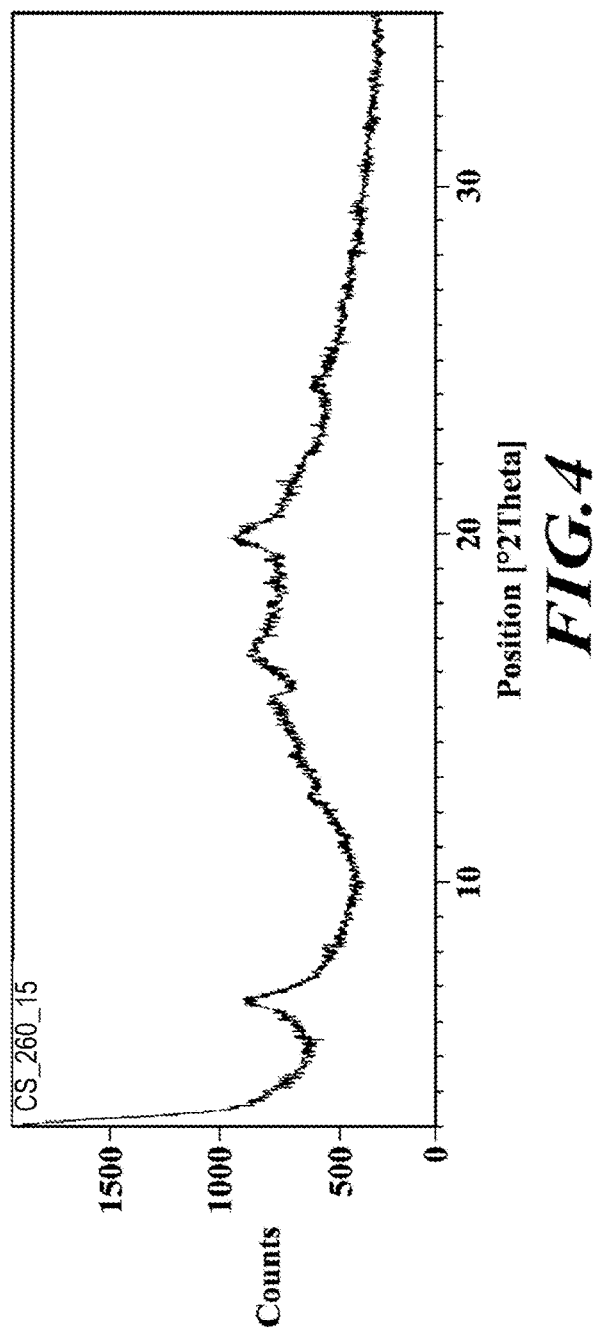
FIG. 4 shows an XRPD diffractogram of meglumine-RP-101.

As used in the specification and appended claims, the singular forms "a," "an" and "the" include plural referents unless the context clearly dictates otherwise.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

As used herein, "individual" (as in the subject of the treatment) means both mammals and non-mammals. Mammals include, for example, humans; non-human primates, e.g., apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist." Certain molecules bind to receptors at locations other than the binding sites of their natural ligands and such allosteric binding molecules may potentiate, activate or agonize the receptor and may enhance the effect of a natural ligand or a co-administered ligand.

A "GLP-1 agonist" or "GLP-1 activator" or "GLP-1 inhibitor" or "GLP-1 antagonist" or "GLP-1 potentiator" or "GLP-1 modulator" as the terms are used herein refer to compounds that interact in some way with the GLP-1 receptor. They can be agonists, potentiators, or activators, or they can be antagonists or inhibitors.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Substantially enantiomerically or diastereomerically" pure means a level of enantiomeric or diastereomeric enrichment of one enantiomer with respect to the other enantiomer or diastereomer of at least about 80%, and more preferably in excess of 80%, 85%, 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by GLP-1 refers to the amount of a compound of the invention that is effective to bind to a GLP-1 receptor in the individual's tissues, wherein the GLP-1 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of GLP-1 activity. A therapeutically effective amount is also one in which any toxic or detrimental effects of the compound of the invention are outweighed by the therapeutically beneficial effects. For example, in the context of treating a malcondition mediated by activation of a GLP-1 receptor, a therapeutically effective amount of a GLP-1 receptor agonist of the invention is an amount sufficient to control the malcondition, to mitigate the progress of the malcondition, or to relieve the symptoms of the malcondition.

As mentioned above, the present disclosure provides a crystalline deanol salt of RP-101 which compound is referred to herein as "deanol-RP-101" (i.e., 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt) and has the structure as identified above.

In more specific embodiments, deanol-RP-101 is a substantially diastereomerically pure form of deanol-RP-103 or deanol-RP-104 as identified above, or a racemic mixture of the same.

In one embodiment, deanol-RP-101, deanol-RP-102, deanol-RP-103 or deanol-RP-104 has a purity in excess of 95% by weight, and on another embodiment has a purity in excess of 98% by weight.

In one embodiment, a racemic mixture of deanol-RP-103 and deanol-RP-104 is provided, wherein the mixture contains a weight ratio of deanol-RP-103 to deanol-RP-104 of about 40:60, 45:55, 48:52, 49:51 or 50:50.

In one embodiment, deanol-RP-101 (as a diastereomeric mixture of deanol-RP-103 and deanol-RP-104) exhibits an X-ray powder diffraction (XRPD) pattern as shown in FIG. 1A, while FIGS. 1B and 1C identify peak assignments for the same.

In one embodiment, deanol-RP-101 (as a diastereomeric mixture of deanol-RP-103 and deanol-RP-104) exhibits an X-ray powder diffraction (XRPD) pattern having characteristic peaks expressed in distances (d-spacing) in degrees 2θ (+/−0.2°) as noted in Table 1A.

TABLE 1A

Characteristic XRPD Peaks

| Pos. [°2Th.] | d-spacing [Å] |
|---|---|
| 6.51 | 13.57 |
| 16.04 | 5.53 |
| 16.92 | 5.24 |
| 17.22 | 5.15 |
| 19.05 | 4.66 |
| 20.12 | 4.41 |
| 20.84 | 4.26 |
| 22.60 | 3.93 |

In one embodiment, deanol-RP-101 is a substantially diastereomerically pure form of deanol-RP-103, and exhibits an X-ray powder diffraction (XRPD) pattern as shown in FIG. 2A, while FIGS. 2B and 2C identify peak assignments for the same.

In one embodiment, deanol-RP-101 is a substantially diastereomerically pure form of deanol-RP-103, and exhibits an X-ray powder diffraction (XRPD) pattern having characteristic peaks expressed in distances (d-spacing) and degrees 2θ (+/−0.2°) as noted in Table 1B.

TABLE 1B

Characteristic XRPD Peaks

| Pos. [°2Th.] | d-spacing [Å] |
|---|---|
| 6.53 | 13.54 |
| 13.70 | 6.47 |
| 16.05 | 5.52 |
| 16.91 | 5.24 |
| 17.22 | 5.15 |
| 19.03 | 4.66 |
| 20.11 | 4.42 |
| 20.80 | 4.27 |
| 22.55 | 3.94 |
| 23.06 | 3.86 |
| 25.41 | 3.51 |

In one embodiment, deanol-RP-101 is a substantially diastereomerically pure form of deanol-RP-104, and exhibits an X-ray powder diffraction (XRPD) pattern as shown in FIG. 3A, while FIGS. 3B and 3C identify peak assignments for the same.

In one embodiment, deanol-RP-101 is a substantially diastereomerically pure form of deanol-RP-104, and exhibits an X-ray powder diffraction (XRPD) pattern having characteristic peaks expressed in distances (d-spacing) and degrees 2θ (+/−0.20) as noted in Table 1C.

TABLE 1C

Characteristic XRPD Peaks

| Pos. [°2Th.] | d-spacing [Å] |
| --- | --- |
| 3.58 | 24.72 |
| 6.51 | 13.57 |
| 7.18 | 12.31 |
| 16.04 | 5.53 |
| 16.92 | 5.24 |
| 17.22 | 5.15 |
| 19.05 | 4.66 |
| 20.12 | 4.41 |
| 20.84 | 4.26 |
| 22.60 | 3.93 |

As mentioned above, deanol-RP-101 contains two chiral centers, and may exist in various isomeric forms (e.g., enantiomers and diastereomers), and thus all chiral, diastereomeric, enantiomeric and racemic forms are intended, including mixtures thereof, unless a particular isomeric form is specifically indicated. For example, deanol-RP-102, as well as deanol-RP-103 and deanol-RP-104, are more specific isomeric forms of deanol-RP-101, which forms may exist in isolation or as a diastereomeric mixture. Accordingly, deanol-RP-101 includes enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

To this end, an "isolated optical isomer" means an isomeric form, such as deanol-RP-103 or deanol-RP-104, which has been substantially purified from the corresponding optical isomer(s). Preferably, the isolated isomer is at least about 80%, and preferably at least 80% or even at least 85% pure, by weight. In other embodiments, the isolated isomer is at least 90% pure, or at least 98% pure, or at least 99% pure, by weight.

"Isotopes" are well known in the art and refer to atoms with the same number of protons but different number of neutrons. For example, carbon 13 ($^{13}C$) is a stable isotope of carbon. Similarly, deuterium ($^{2}H$) is a stable isotope of hydrogen, while tritium ($^{3}H$) is a radioactive isotope of hydrogen. Deanol-RP-101 containing one or more isotopes is specifically within the scope of this disclosure.

Deanol-RP-101 may be combined with a pharmaceutically acceptable carrier to provide pharmaceutical compositions useful for treating the biological conditions or disorders noted herein in mammalian species, including humans. The particular carrier employed in these pharmaceutical compositions may vary depending upon the type of administration desired (e.g., intravenous, oral, topical, suppository, or parenteral). Accordingly, in one embodiment, a pharmaceutical composition is provided comprising deanol-RP-101 together with at least one pharmaceutically acceptable carrier, diluent or excipient.

In certain embodiments, a method is provided for activation, potentiation or agonism of a glucagon-like peptide 1 comprising contacting the receptor with an effective amount of deanol-RP-101, or a pharmaceutical composition as disclosed above.

In further embodiments, a method is provided for activation or agonism of a GLP-1 receptor by contacting the receptor with an effective amount of deanol-RP-101 in combination on conjunction with the GLP-1 peptides GLP-1(9-36) and/or GLP-1(7-36).

In certain embodiments, a method is provided for treatment of a disease or malcondition in a subject for which activation, potentiation or agonism of a GLP-1 receptor is medically indicated, by administering an effective amount of deanol-RP-101 to the subject at a frequency and for a duration of time sufficient to provide a beneficial effect to the subject.

In certain embodiment the subject is a human being.

In certain embodiments, methods are provided for use of deanol-RP-101 for preparation of a medicament adapted for treatment of a disorder or a malcondition wherein activation or inhibition of a GLP-1 receptor is medically indicated.

In certain embodiments, methods are provided activating, potentiating, or agonizing (i.e., to have an agonic effect, to act as an agonist) a GLP-1 receptor with deanol-RP-101. The method involves contacting the receptor with a suitable concentration of deanol-RP-101 to bring about activation of the receptor. The contacting can take place in vitro, for example in carrying out an assay to determine the GLP-1 receptor activation activity. In certain embodiments, the method for activating a GLP-1 receptor is carried out in vivo; that is, within the living body of a mammal, such as a human or a test animal. Deanol-RP-101 can be supplied to the living organism via a suitable routes (e.g., orally), or can be provided locally within the body tissues. In the presence of deanol-RP-101, activation of the receptor takes place, and the effect thereof can be studied.

In certain embodiments, a method is provided for the treatment of a disease or malcondition in a patient for which activation of a GLP-1 receptor is medically indicated, wherein the patient is administered deanol-RP-101 in a dosage, at a frequency, and for a duration to produce a beneficial effect on the patient. Deanol-RP-101 can be administered by any suitable means.

In certain embodiments, the disease or malcondition is type I diabetes, type II diabetes, gestational diabetes, obesity, excessive appetite, insufficient satiety, and metabolic disorder.

In other embodiments, the malcondition is non-alcoholic fatty liver disease (NAFLD) and/or non-alcoholic steatohepatitis (NASH). NAFLD is believed to be caused by the disruption of hepatic lipid homeostasis and, at least in a portion of patients, can progress to NASH. NAFLD is associated with insulin resistance in type 2 diabetes mellitus, and GLP1 increases insulin sensitivity and aids glucose metabolism. Deanol-RP-101 is beneficial in this context by serving to increase fatty acid oxidation, decrease lipogenesis, and/or improve hepatic glucose metabolism.

In certain embodiments, methods for synthesis of deanol-RP-101 are provided as more fully illustrated herein below. In certain other embodiments, the invention provides intermediate compounds associated with such methods of synthesis.

EXAMPLES

Reaction Conditions and Abbreviations

Pyridine, dichloromethane (DCM), tetrahydrofuran (THF), and toluene used in the procedures were from Aldrich Sure-Seal bottles or Acros AcroSeal dry solvent and kept under nitrogen ($N_2$). All reactions were stirred magnetically and temperatures are external reaction temperatures. The following abbreviations are used: ethyl acetate (EA), 1-methy-2-pyrrolidinone (NMP), triethylamine (TEA), N-hydroxybenzotriazole (HOBt), 1-ethyl-3-(3-dimethylaminopropyl) carbodiimide hydrochloride (EDC), N,N-dimethylformamide (DMF), dimethyl acetamide (DMA), Di-tert-butyl dicarbonate ($Boc_2O$), N,N-Diisopropylethylamine (DIEA), acetic acid (AcOH), hydrochloric acid (HCl), O-(7-azabenzotriazol-1-yl)-N,N,N',N'-tetramethyluronium hexafluorophosphate (HATU), 4-dimethylaminopyridine (DMAP), tert-butanol (t-BuOH), sodium hydride (NaH), sodium triacetoxyborohydride ($Na(OAc)_3BH$), ethanol (EtOH), methanol (MeOH), acetonitrile (ACN).

NMR Spectra $^1H$ NMR (400 MHz) and $^{13}C$ NMR (100 MHz) were obtained in solution of deuteriochloroform ($CDCl_3$) or dimethyl sulfoxide ($d_6$-DMSO). NMR spectra were processed using MestReNova 6.0.3-5604.

X-Ray Powder Diffraction (XRPD)

XRPD analysis was carried out on a Panalytical X'pert pro, scanning the samples between 3 and 35° 2θ. The material was gently ground and loaded onto a multi well plate with Kapton or mylar polymer film to support the sample. The multi well plate was then loaded into a Panalytical diffractometer running in transmission mode and analyzed, using the following experimental conditions.

| Raw Data Origin: | XRD measurement |
|---|---|
| (*.XRDML) | |
| Scan Axis: | Gonio |
| Start Position [°2θ]: | 3.0066 |
| End Position [°2θ]: | 34.9866 |
| Step Size [°2θ]: | 0.0130 |
| Scan Step Time [s]: | 18.8700 |
| Scan Type: | Continuous |
| PSD Mode: | Scanning |
| PSD Length [°2θ]: | 3.35 |
| Offset [°2θ]: | 0.0000 |
| Divergence Slit Type: | Fixed |
| Divergence Slit Size [°]: | 1.0000 |
| Measurement Temperature [° C.]: | 25.00 |
| Anode Material: | Cu |
| K-Alpha1 [Å]: | 1.54060 |
| K-Alpha2 [Å]: | 1.54443 |
| K-Beta [Å]: | 1.39225 |
| K-A2/K-A1 Ratio: | 0.50000 |
| Generator Settings: | 40 mA, 40 kV |
| Goniometer Radius [mm]: | 240.00 |
| Dist. Focus-Diverg. Slit [mm]: | 91.00 |
| Incident Beam | |
| Monochromater: | No |
| Spinning: | No |

Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective, unless otherwise stated.

Thermogravimetric Analysis (TGA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm3/min.

Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 250° C. at scan rate of 10° C./min and the resulting heat flow response monitored.

$^1H$ Nuclear Magnetic Resonance ($^1H$ NMR)

$^1H$-NMR experiments were performed on a Bruker AVA500 (frequency: 500 MHz). Experiments were performed in deuterated DMSO and each sample was prepared to 10 mM concentration.

High Performance Liquid Chromatography-Ultraviolet Detection (HPLC-UV)

Instrument: Dionex Ultimate 3000
Column: ACE Ultracore C18, 4.6×50 mm, 2.5 μm
Column Temp: 40° C.
Autosampler Temp: 25° C.
UV wavelength: 260 nm
Injection Volume: 5 μL
Flow Rate: 2 mL/min
Mobile Phase A: Water, 0.1% trifluoroacetic acid
Mobile Phase B: Acetonitrile, 0.1% trifluoroacetic acid
Standard: Meglumine-RP-101 in DMSO to 1.00 mg/mL.
Gradient program:

| Time (minutes) | Solvent B [%] |
|---|---|
| 0.00 | 45 |
| 1.00 | 45 |
| 2.00 | 100 |
| 2.50 | 100 |
| 2.51 | 45 |
| 4.00 | 45 |

Example 1

Synthesis of Deanol-RP-101

Synthetic Scheme for Intermediate 6

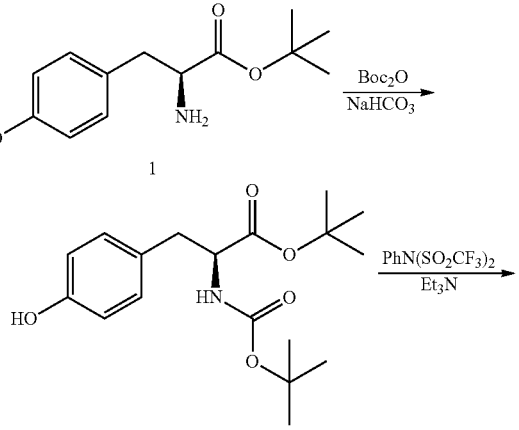

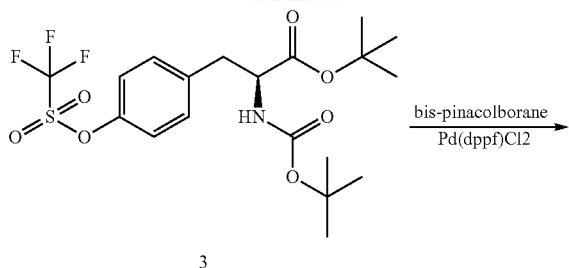

3

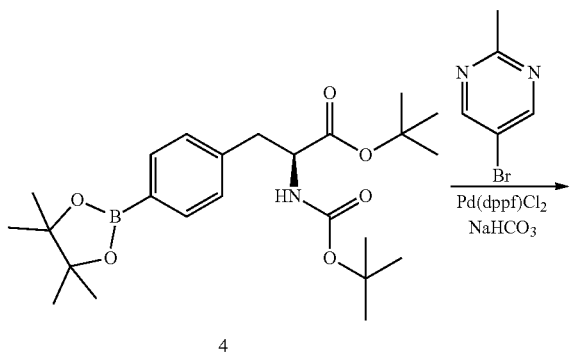

4

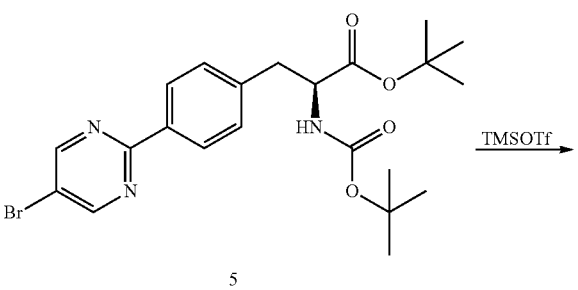

5

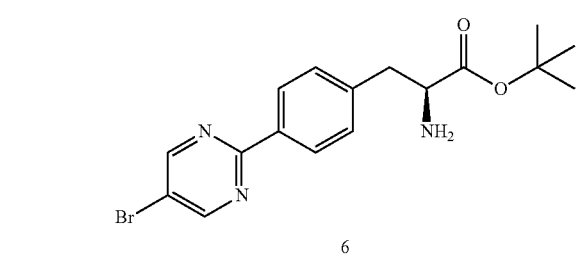

6

Step 1

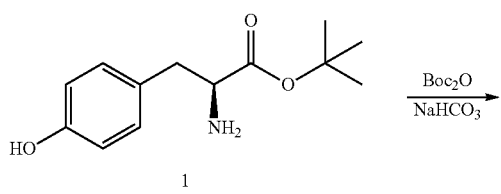

1

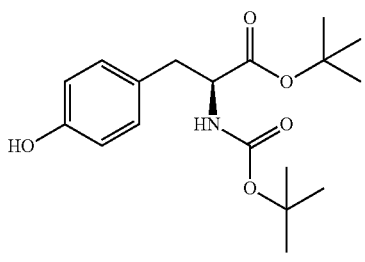

2

A 100 L stirred reactor was charged with water (52.5 kg), sodium bicarbonate (4.0 kg, 46.0 moles), L-tyrosine-t-butyl ester HCl (1) (10.0 kg, 42.2 moles) and acetone (36 kg). The mixture was stirred at 20-25° C.

In a separate vessel, di-tert-butyl dicarbonate (10.0 kg, 45.8 moles) and acetone (10 kg) were charged and the mixture stirred until a solution is formed. The $Boc_2O$/acetone solution was charged to the reactor over a period of 1 h while controlling the addition so that the temperature did not exceed 25° C. The mixture was stirred for 2 h at 20-25° C. then sampled for completion by HPLC analysis. Upon completion, the reaction mixture was concentrated under ambient pressure to remove approximately 80% of volume (~40 L). The resulting mixture was cooled to 20-25° C.

MTBE (37 kg) and acetic acid (2 kg) were charged to the reactor and the mixture stirred for 10-20 minutes after which stirring was stopped and the phases allowed to separate. The organic layer was collected and the aqueous layer returned to the reactor. MTBE (38 kg) was charged to the reactor and the mixture stirred for 10-20 minutes. Stirring was stopped and the phases allowed to separate. The aqueous layer was drained form the reactor and the first organic extract recharged to the reactor. Water (71 kg) was charged to the reactor and the mixture stirred for 10-20 minutes. Stirring was stopped to allow the phases to separate. The aqueous phase was drained from the reactor. The remaining organic phase was concentrated under ambient pressure to remove approximately 90% of volume. The mixture was cooled to 0-5° C. over a period of 2-3 h. Petroleum ether (32 kg) was added and the mixture stirred for 3 h at 0-5° C. The resulting slurry was filtered then dried in an oven under reduced pressure at 35-40° C. for 16 h to obtain N-tert-butoxycarbonyl-L-tyrosine-t-butyl ester (2) (12.6 kg, 37.3 moles, 88.5% yield, HPLC purity: 99%).

Step 2

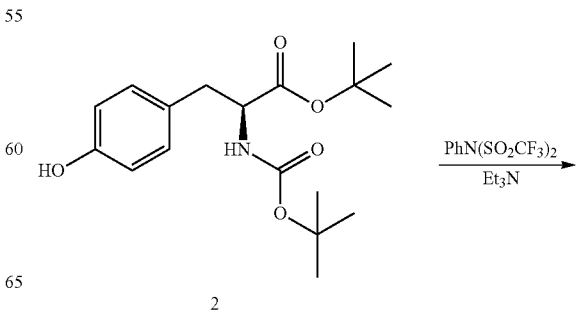

2

-continued

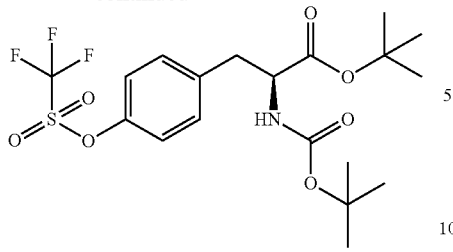

3

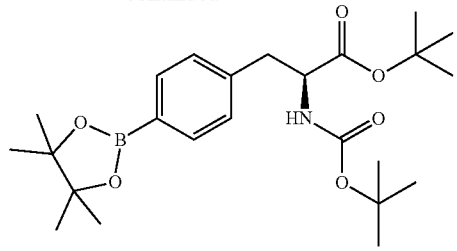

4

To a 100 L stirred reactor was charged with dichloromethane (94.3 kg). The contents was cooled to 5±3° C. N-tert-butoxycarbonyl-L-tyrosine-t-butyl ester (12.5 kg, 37.0 moles) (2) and N-phenyl-bis(trifluoromethane sulfonimide (13.5 kg, 37.8 moles) were charged to the reactor. Triethylamine (5.5 kg, 54.5 moles) was slowly added to the reactor while keeping the temperature below 10° C. The mixture was heated to 25±5° C. and the mixture stirred at this temperature for 20 h. The mixture was sampled for completion of reaction by HPLC analysis. The mixture was concentrated by distillation to minimum stir volume at 40±5° C. Petroleum ether (65 kg) and water (37 kg) were charged to the reactor, consecutively and the mixture stirred. Saturated sodium carbonate solution (15 kg) was charged to the reactor. Methanol (8.1 kg) was charged to the reactor. The mixture was stirred for 10-15 minutes then the stirring was stopped to allow for the phases to separate. The phases were separated and the aqueous phase returned to the reactor. Petroleum ether (22 kg) was added to the reactor and the mixture stirred for 10-15 mins. The stirring was stopped to allow the phases to separate. The aqueous phase was drained from the reactor and the first organic extract was combined with the organic phase in the reactor. Brine (50 kg) was charged to the reactor and the mixture stirred for 10-15 minutes. Stirring was stopped to allow the phases to separate. The aqueous phase was drained and discarded. The organic phase was drained to a drum. To this drum was added sodium sulfate (5 kg) and the mixture stirred. The mixture was transferred to a rotary evaporator vessel through a filter remove the solid sodium sulfate. The solution was concentrated by rotary evaporation to dryness to afford tert-butyl (S)-2-((tert-butoxycarbonyl)amino)-3-(4-(((trifluoromethyl)sulfonyl)oxy)phenyl)propanoate (3) (17.3 kg, 36.8 moles, 99.6% yield, purity: 98.8%).

Step 3

A 100 L stirred reactor was charged with dimethylsulfoxide (77 kg). Potassium acetate (10.8 kg) and (S)-tert-butyl 2-((tert-butoxycarbonyl)amino)-3-(4-(((trifluoromethyl)sulfonyl)oxy)phenyl)propanoate (3) (17.3 kg, 36.8 moles) were charged. The mixture was stirred at 20-25° C. 4,4,4',4',5,5,5',5'-octamethyl-2,2'-bi(1,3,2-dioxaborolane) (9.4 kg) was charged to the reactor. The mixture was degassed with nitrogen for 10 min. Pd(dppf)Cl2 (0.27 kg) was charged to the reactor and the mixture degassed again for 10 min. The reaction mixture was stirred at 90-95° C. for 20 h after which a sample was taken for HPLC analysis to determine completion of reaction. The reaction mixture was cooled to 20-25° C. t-Butyl methylether (26 kg) was charged to the reactor and the mixture was stirred for 10 minutes. The mixture was allowed to stand for 40 minutes to allow the phases to separate. The t-butyl methylether phase was separated and the DMSO phase was returned to the reactor. t-Butyl methylether (26 kg) was charged to the reactor. The mixture was stirred for 10-20 minutes then allowed to stand for 40 min for the phases to separate. The phases were separated and the DMSO phase was returned to the reactor. t-Butyl methylether was charged to the reactor and the mixture stirred for 10-20 min then allowed to stand for 40 min for the phases to separate. The phases were separated and combined with the previous two organic extracts and recharged to the reactor. Water (30 kg) was charged to the reactor and mixture stirred for 10-20 min. Stirring was stopped to allow the phases to separate. The aqueous phase was drained from the reactor. Water (30 kg) was charged to the reactor and mixture stirred for 10-20 min. Stirring was stopped to allow the phases to separate. The aqueous phase was drained from the reactor. The organic extract was drained into a vessel. Sodium sulfate (5 kg) was charged to the vessel and stirred. The solution was filtered into a rotary evaporator flask and concentrated to dryness to obtain tert-butyl (S)-2-((tert-butoxycarbonyl)amino)-3-(4-(4,4,5,5-tetramethyl-1,3,2-dioxaborolan-2-yl)phenyl)propanoate (4) (15.9 kg, 35.5 moles, 96.5% yield, purity: 91.6%).

Step 4

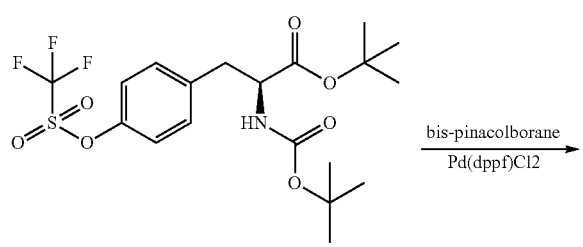

3

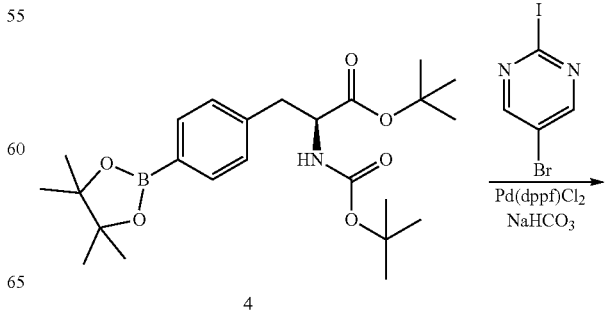

4

21
-continued

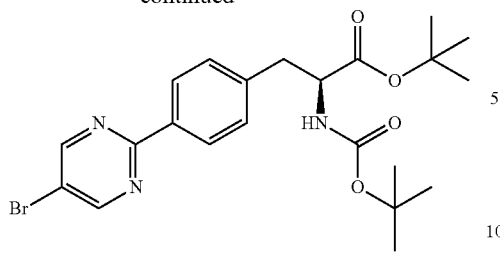

5

A 100 L reactor was charged with water (23 kg). The temperature was adjusted to 25-30° C. Sodium bicarbonate (2.77 kg) was charged to the reactor. After a solution was formed, 1,4-dioxane (45 kg) was charged to the reactor. 5-Bromo-2-iodopyrimidine (3.14 kg) and (S)-tert-butyl 3-(4-(5-bromopyrimidin-2-yl)phenyl)-2-((tert-butoxycarbonyl)amino)propanoate (4) (4.92 kg, 11.0 moles) were charged to the reactor. The mixture was degassed with nitrogen for 15-20 min. Pd(dppf)Cl$_2$ (160 g) was charged to the reactor. The reaction was degassed for 15-20 min with nitrogen. The mixture was heated at 75-85° C. for 20 h. The reaction mixture was sampled for HPLC analysis to determine the completion of reaction. Once the reaction was determined to be complete, the mixture was cooled to 40-45° C. Water (44 kg) was charged to the reactor. The mixture was then cooled to 0-5° C. and stirred for 30 min at this temperature. The resulting slurry was filtered and the filter cake washed with water (16 kg). The solids are dried in an oven at 45-50° C. under vacuum (~0.1 mPa) until LOD is NMT 1%.

Methanol (30 kg) was charged to the reactor. The dried crude product was charged to the reactor and the mixture was heated at 65-70° C. Activated charcoal (1 kg) was charged to the reactor. The mixture was further heated at 65-70° C. for 90 min. The hot mixture was filtered to remove the charcoal and the filtrate was concentrated to approximately 50-60 L. The mixture was cooled to 0-5° C. The resulting slurry was filtered and washed with cold methanol (2 kg). The solids were dried in an oven under ~0.1 mPa at 40-45° C. for 16 h or until LOD≤1% to afford tert-butyl (S)-3-(4-(5-bromopyrimidin-2-yl)phenyl)-2-((tert-butoxycarbonyl)amino)-propanoate (5) (3.1 kg, 6.5 moles, 59% yield, purity: 92%).

Step 5

22
-continued

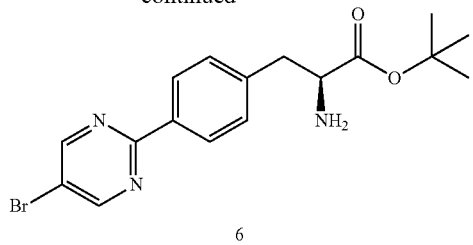

A 500 L reactor was charged with MTBE (210 kg). The reactor was set to 0-5° C. tert-Butyl (S)-3-(4-(5-bromopyrimidin-2-yl)phenyl)-2-((tert-butoxycarbonyl)-amino)-propanoate (5) (18.88 kg, 39.5 moles) was charged to the reactor and the mixture stirred. Trimethylsilyl trifluoromethanesulfonate (14 kg, 63 moles) was charged and the mixture stirred at 0-5° C. for 24 h. The reaction mixture was sampled for completion of reaction by HPLC analysis. Once the reaction was determined to be complete, petroleum ether (155 kg) was charged to the reactor and stirred for 50 min. The mixture was filtered and the filter cake was washed with petroleum ether (15 kg) to yield the crude product tert-butyl (S)-2-amino-3-(4-(5-bromopyrimidin-2-yl)phenyl)propanoate (6).

Water (190 kg) was charged to the reactor and the temperature was adjusted to 25-30° C. Sodium bicarbonate (16.5 kg) was charged the reactor and stirred for a minimum of 20-30 min to ensure complete dissolution. Once a solution was formed, the temperature of the solution was adjusted to 10-20° C. The crude product 6 was charged to the reactor and the resulting mixture stirred for 3 h at 10-20° C. The mixture was transferred to a centrifuge filter and the resulting filter cake was washed with water (50 kg). The solids are dried in an oven at 45-50° C. for 16 h (approximately 0.1 mPa).

Methanol (50 kg) was charged to the reactor. The dried crude product 6 was charged back to the reactor and the mixture stirred and heated at 50-55° C. Water (25 kg) was slowly added to the reaction mixture and the mixture was cooled to 36-38° C. for a period of approximately 1 h. Crystalline tert-butyl (S)-2-amino-3-(4-(5-bromopyrimidin-2-yl)phenyl)propanoate (6) (50 g) was charged to the reactor as seeds. The mixture was cooled to 15-20° C. and stirred for 90 min. The resulting slurry was transferred to a centrifuge filter. The solid mass was washed with water (10 kg) and dried in an oven at 40-45° for 16 h (0.1 mPa) to afford tert-butyl (S)-2-amino-3-(4-(5-bromopyrimidin-2-yl)phenyl)propanoate (6) (10.1 kg, 26.7 moles, 67.6% yield, HPLC purity: 98.9%).

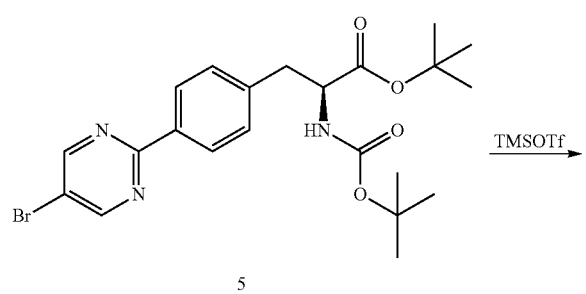

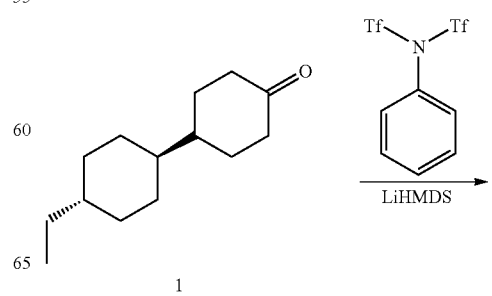

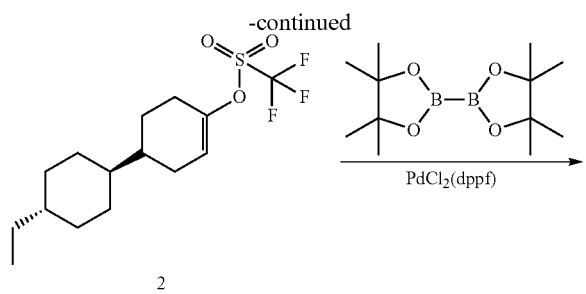

Step 1

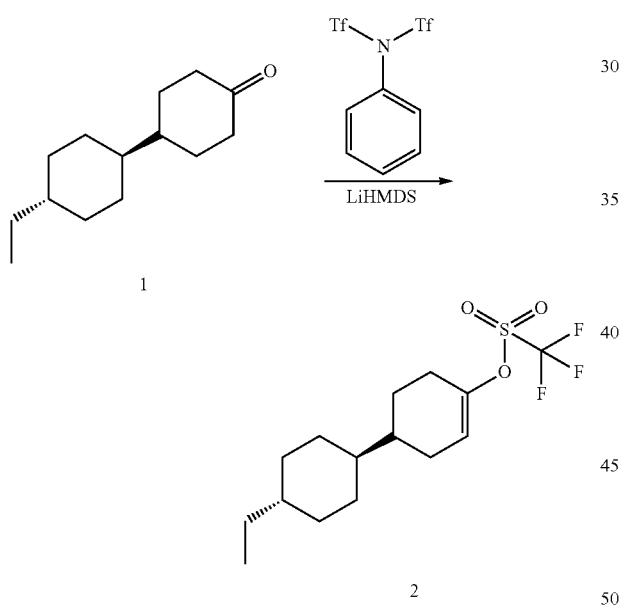

To a reactor was charged THF (10 L) and (1'r, 4'r)-4'-ethyl-[1,1'-bi(cyclohexan)]-4-one (1) (2.0 kg, 9.6 mol). The mixture was stirred and cooled to −78° C. Lithium bis(trimethylsilyl)amide (1 M in THF, 11 L, 10.6 mol) was charged to the reactor over a period of 2 h. The reaction mixture was stirred for 1 h. 1,1,1-trifluoro-N-phenyl-N-((trifluoromethyl)sulfonyl) methanesulfonamide (3.8 kg, 10.6 mol) was charged to the reactor and the mixture was stirred for 1.5 h. The reaction mixture was sampled for completion of reaction by GC analysis (acceptance criteria: ≤1.0%). The reaction mixture was concentrated to approximately 12 L, then Hexane (10 L) was added to the mixture. Saturated sodium carbonate (10 L) and water (10 L) was charged to the reactor. The mixture was stirred for 30 min then allowed to stand for phase separation. The layers were separated and the aqueous layer was returned to the reactor. Hexane (10 L) was charged to the reactor and the mixture stirred for 30 min then allowed to stand for phase separation. The aqueous layer was drained and the first organic extract was recharged to the reactor. Water (10 L) was charged to the reactor and the mixture stirred for 30 min. The mixture was then allowed to stand for phase separation. The aqueous layer was drained and set aside as waste. Sodium sulfate (0.5 kg) was charged to the reactor. The mixture was stirred for 30 min then drained and filtered. The filtrate was transferred to a rotary evaporator vessel and concentrated to afford racemic (1RS,1'r,4'RS)-4'-ethyl-[1,1'-bi(cyclohexan)]-3-en-4-yl trifluoromethanesulfonate (2). The concentrate was sampled for GC analysis and carried forward to the next step without further purification (3.3 kg, 9.7 mol, Purity: 94%).

Step 2

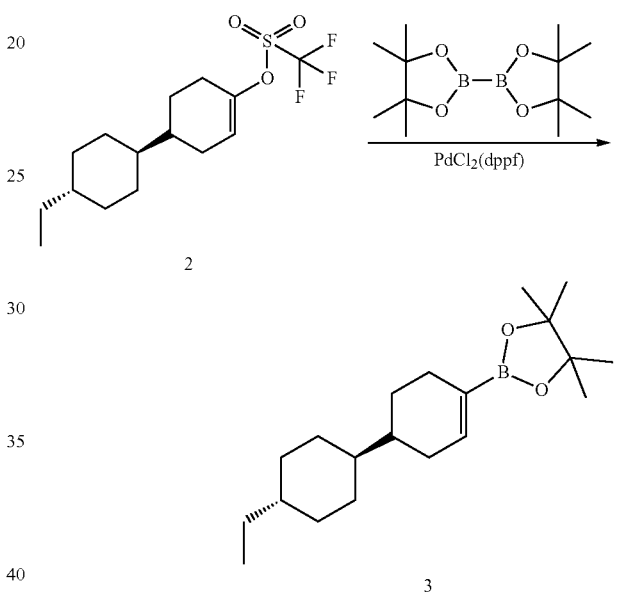

To a reactor was charged dioxane (20 L), racemic (1RS, 1'r,4'RS)-4'-ethyl-[1,1'-bi(cyclohexan)]-3-en-4-yl trifluoromethanesulfonate (2) (crude product from previous step, 3.3 kg, ~9.72 mol), 4,4,4',4',5,5,5',5'-octamethyl-2,2'-bi(1,3,2-dioxaborolane) (2.1 kg, 8.26 mol) and potassium acetate (2.9 kg, 29.15 mol). The mixture was stirred and heated at 40° C. The mixture was degassed by streaming nitrogen through the reactor. PdCl$_2$(dppf) (142 g, 0.19 mol) was added and the mixture degassed. The mixture was heated at 100° C. for 4 h. A sample was taken to determine the completion of reaction by gas chromatography (acceptance criteria: ≤1.0% starting material vs. product). Once determined complete, the mixture was cooled to 25-30° C. Ethyl acetate (18 L) and water (22.5 L) were charged to the reactor and stirred for 30 min. The mixture was allowed to stand for phase separation. The phases were separated and the aqueous phase was returned to the reactor. Ethyl acetate (10 L) was charged to the reactor and the mixture stirred for 30 min. The mixture was then allowed to stand for phase separation. The aqueous phase was drained and the first organic extract was recharged to the reactor. Magnesium sulfate (0.5 kg) was charged to the reactor and stirred. The mixture was filtered and the filtrate transferred to a rotary evaporator vessel. The filtrate was concentrated to dryness crude product (3.5 kg, GC purity: 82%).

Another batch of intermediate 2 was subjected to the same process and the product (5.6 kg) was combined with the first batch. The combined crude material (9.1 kg, purity 82%) was purified by column chromatography to give racemic 2-((1RS,1'r,4'RS)-4'-ethyl-[1,1'-bi(cyclohexan)]-3-en-4-yl)-4,4,5,5-tetramethyl-1,3,2-dioxaborolane (3) as a light brown liquid (4.1 kg, 12.9 moles, 49% yield for two steps, purity: 90%).

Synthetic Scheme for Deanol-RP-101

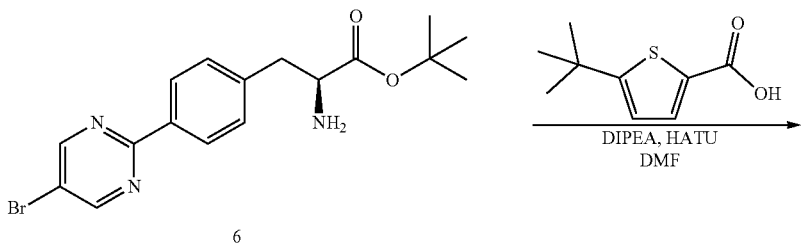

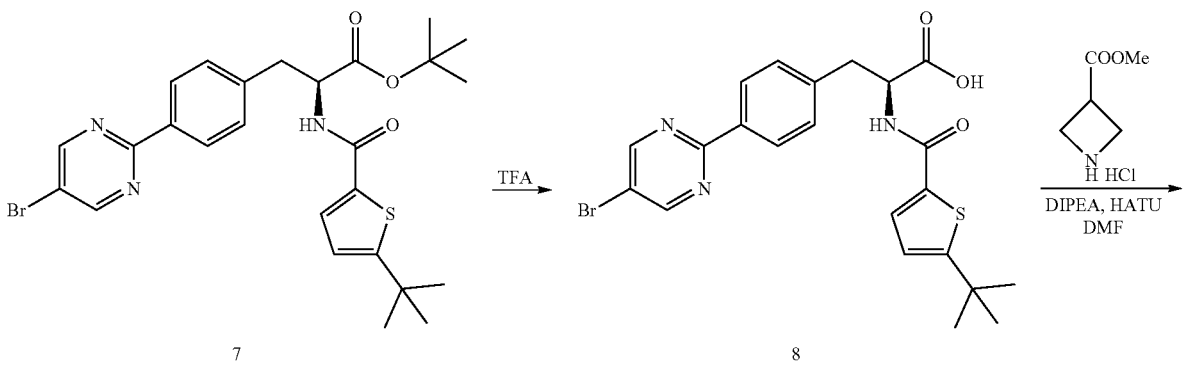

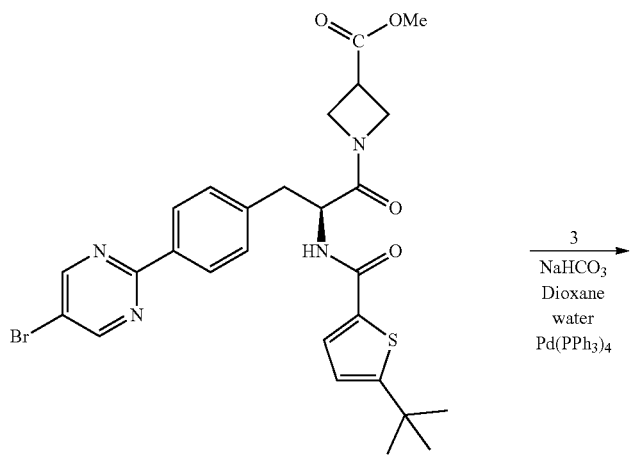

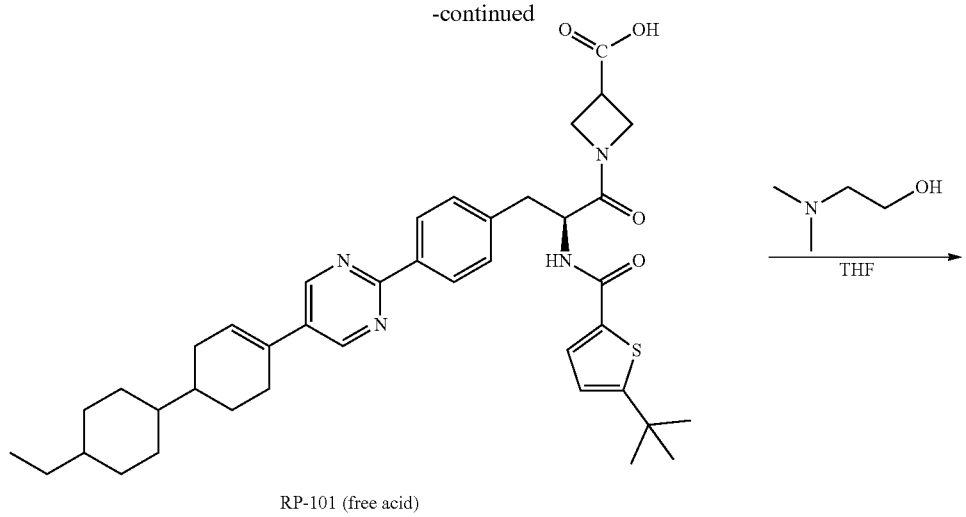
RP-101 (free acid)
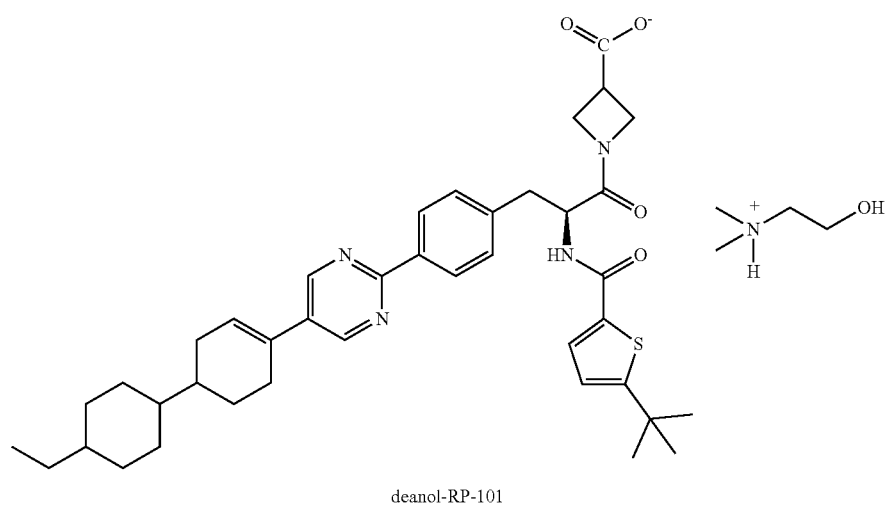
deanol-RP-101
Step 1
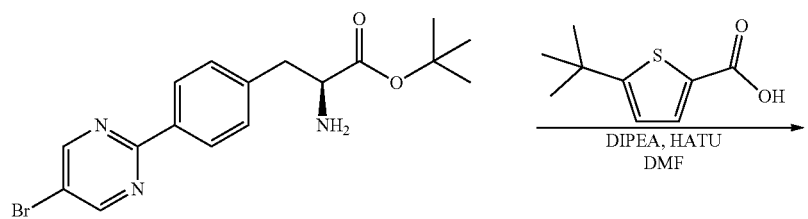

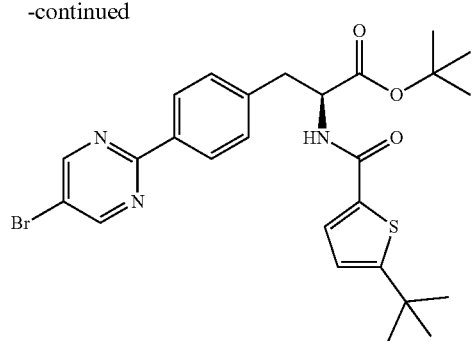

7

(S)-tert-Butyl 2-amino-3-(4-(5-bromopyrimidin-2-yl)phenyl)propanoate (6) (4.00 kg, 10.57 moles) was charge in a 100 L reactor. DMF (41.60 kg) was charged to the reactor. The mixture was stirred at 20-25o until a solution is formed. The mixture was cooled to −5 to 0° C. Diisopropylethylamine (2.74 kg, 21.24 moles) was charged to the reactor. 5-(tert-Butyl)thiophene-2-carboxylic acid (1.93 kg, 10.47 moles) was charged to the reactor and the mixture stirred fir 30 min at −5 to 0° C. HATU (4.22 kg, 11.1 moles) was charged to the reactor and the mixture was stirred for 30 min at −5 to 0° C. The mixture was sampled for completion of reaction by HPLC (criterion: NMT 1.0%). Once the reaction was determined to be complete, water (precooled to 0-5° C.) was charged to the reactor. The mixture was stirred at 0-5° C. for 2 h. The mixture was filtered in a Buchner-type funnel then washed with water (12 kg). The filter cake was blown with nitrogen until the liquid stopped draining. The wet cake was transferred into the 100 L reactor. Dichloromethane (26.5 kg) was charged to the reactor and stirred. Water (20 kg) was charged to the reactor. The mixture was stirred for 30 min. The mixture was allowed to stand for 30 min for phase separation. The organic phase (lower layer) was drained from the reactor and transferred to a rotary evaporation vessel. The solution was concentrated by rotary evaporation under reduced pressure at a bath temperature of 25-30° C. to afford crude (S)-tert-butyl 3-(4-(5-bromopyrimidin-2-yl)phenyl)-2-(5-(tert-butyl)thiophene-2-carboxamido)propanoate (7) (6.250 kg, quantitative yield, 98.3 purity).

Step 2

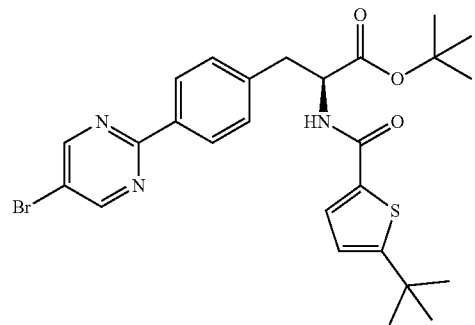

7

→ TFA

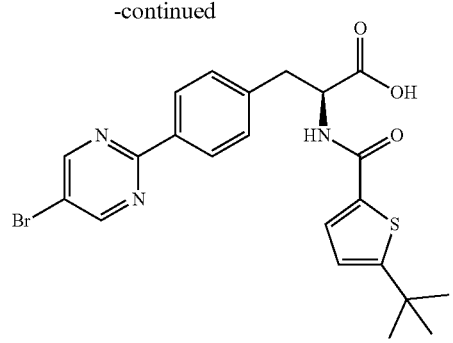

8

Trifluoroacetic acid (25.7 kg, 22.54 moles) was charge to a 100 L reactor A and cooled to 0-5° C. (S)-tert-Butyl 3-(4-(5-bromopyrimidin-2-yl)phenyl)-2-(5-(tert-butyl)thiophene-2-carboxamido)propanoate (7) (5.70 kg, 10.47 moles) was charged to the reactor. The mixture was stirred and the reaction temperature adjusted to 10-15° C. The reaction mixture was stirred at 10-15° C. for 25 h.

Acetone (18.7 kg) and water (35.91 kg) were charged to a 100 L reactor B. The solution was cooled to 0-5° C. The reaction mixture from Reactor A was transferred to Reactor B. The resulting mixture was stirred for 2 h at 0-5° C. The mixture was filtered through a Buchner type filter. The filter cake was washed with water (170 kg) until the pH of the filtrate is between pH 6 and 7. The filter cake was washed hexane (5.7 kg). The filter cake was transferred to drying trays and dried under reduced pressure at 30-40° C. for 48 h. The dried solids was charged to a 100 L reactor. Dichloromethane (57 kg) was charged to the reactor and the mixture stirred at 20-25° C. for 30 min then allowed to stand for phase separation. The organic (bottom) layer was drained into a rotary evaporator vessel and concentrated to dryness to provide crude (S)-3-(4-(5-Bromopyrimidin-2-yl)phenyl)-2-(5-(tert-butyl)thiophene-2-carboxamido)propanoic acid (8) (4.23 kg, 83% yield, purity: 98.5%).

Step 3

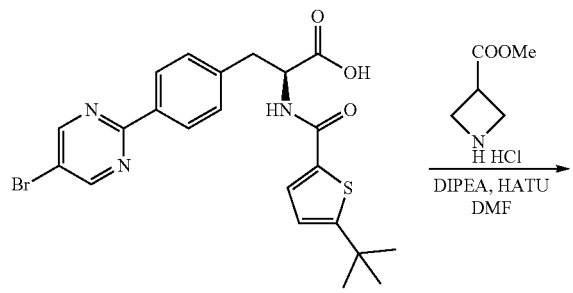

8

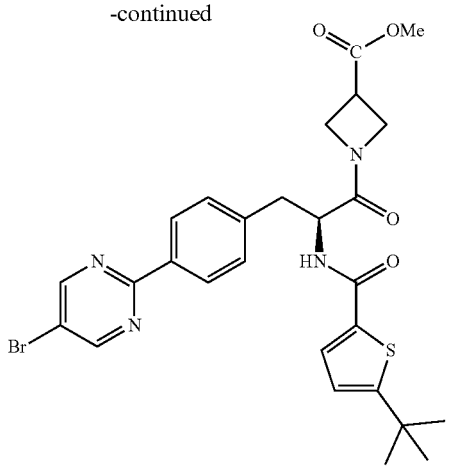

9

(S)-3-(4-(5-Bromopyrimidin-2-yl)phenyl)-2-(5-(tert-butyl)thiophene-2-carboxamido)propanoic acid (8) (4.00 kg, 8.19 moles) was charged to a 100 L reactor. Dimethyl formamide (37.80 kg) was charged to the reactor and the mixture stirred until a solution is formed. The mixture was cooled to −10 to −5° C. Diisopropylethylamine amine (5.32 kg, 41.16 moles) was charged to the reactor. Methyl azetidine-3-carboxylate HCl (3.72 kg, 24.61 moles) was charged to the reactor slowly while maintaining the temperature of the mixture at −10 to −5° C. After complete addition, the mixture was stirred for 30 min. HATU (9.36 kg, 24.62 moles) was charged to the reactor in small portions to maintain the temperature of the mixture at −10 to −5° C. The mixture was stirred for 1 h. A sample was taken to determine the completion of reaction by HPLC analysis. (criterion: NMT 1.0%). Once the reaction was determined to be complete, water (40.0 kg, prechilled in another reactor to 0-5° C.) was slowly charged to the reaction mixture. The resulting suspension was stirred at 0-5° C. for 2 h then filtered in a centrifuge filter. The filter cake was washed with water (40 kg). The wet filter cake was charged back to the reactor. Dichloromethane (32.0 kg) was charged to the reactor and the mixture stirred for 30 min. The mixture was filtered to remove insoluble solids and the filtrate was recharged to the reactor. The solution was allowed to stand for NLT 30 min to allow for phase separation. The organic phase (bottom layer) was drained into a rotary evaporator vessel and concentrated to dryness to yield crude (S)-methyl 1-(3-(4-(5-bromopyrimidin-2-yl)phenyl)-2-(5-(tert-butyl)thiophene-2-carboxamido)propanoyl)azetidine-3-carboxylate (9) (5.33 kg, purity: 90.5%).

Step 4

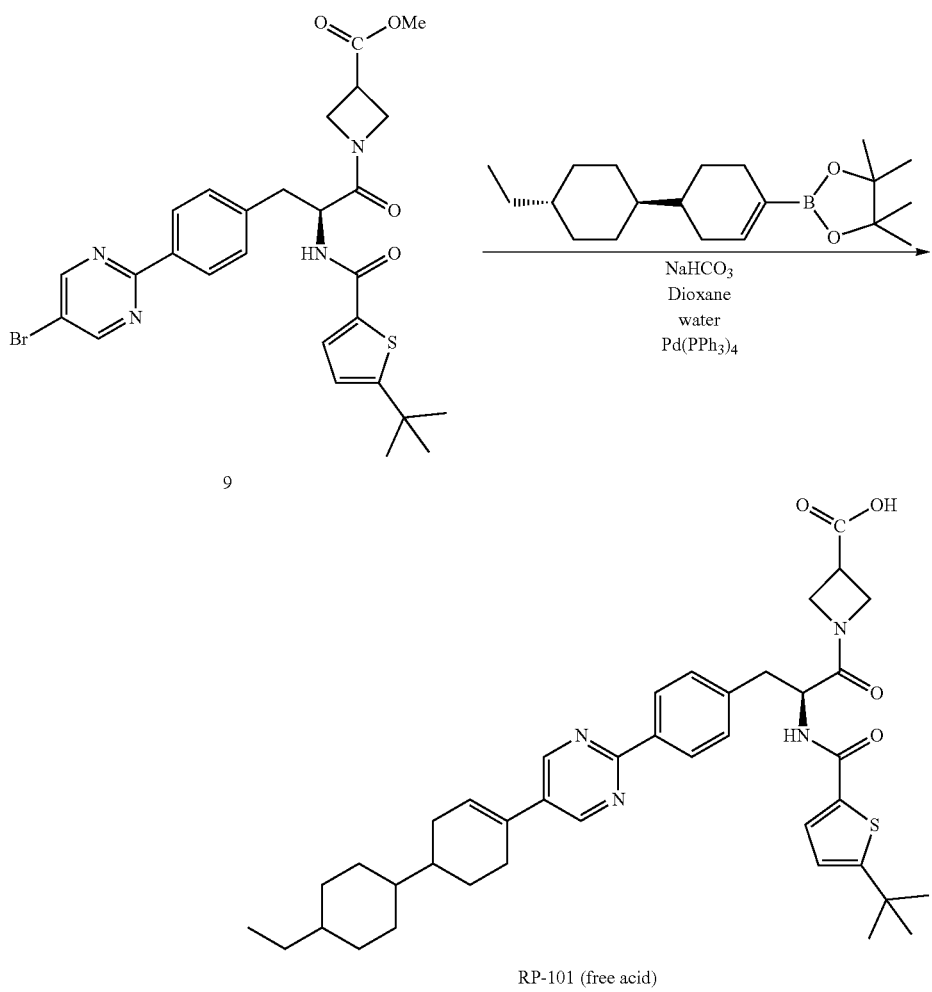

RP-101 (free acid)

1,4-Dioxane (35.10 kg) and water (15.3 kg) were charged to a 100 L reactor. (S)-methyl 1-(3-(4-(5-bromopyrimidin-2-yl)phenyl)-2-(5-(tert-butyl)-thiophene-2-carboxamido) propanoyl)azetidine-3-carboxylate (9) (4.50 kg, 7.69 moles) was charged to the reactor and the mixture stirred at 20-25° C. (2.60 kg, 8.17 moles). Racemic 2-((1RS,1'r,4'RS)-4'-ethyl-[1,1'-bi(cyclohexan)]-3-en-4-yl)-4,4,5,5-tetramethyl-1,3,2-dioxaborolane (3) and sodium bicarbonate (1.95 kg, 23.21 moles) were charged to the reactor. The mixture was stirred and then sparged with nitrogen through a dip tube to displace oxygen. Pd(PPh$_3$)$_4$ (0.190 kg, 0.164 moles) was charged to the reactor. The mixture was stirred and sparged with nitrogen through a dip tube. The mixture was heated at 80-85° C. for 17 h. A sample was taken to determine the completion of reaction by HPLC analysis (criterion: NMT 1.0%). Once the reaction was determined to be complete, the reaction mixture was cooled to 50-60° C. The mixture was filtered to remove insoluble material. The filtrate was transferred to a clean reactor and cooled to 5-15° C. Acetic acid (1.0 kg) was charged to the reactor. The resulting slurry was cooled to 0-5° C. and stirred at this temperature for 2 h. The mixture was filtered through the centrifuge filter and washed with water (22 kg). The wet cake was transferred to a clean 100 L reactor. Tetrahydrofuran (47.25 kg) was charged to the reactor and the mixture was stirred at 20-25° C. until a solution was formed. Activated carbon (2.25 kg) was charged to the reactor. The mixture was heated at 60-65° C. for 7 h. The mixture was filtered hot into a clean reactor. The filter cake was washed with THF (19.8 kg) and the filtrate charged into the reactor. Thiourea (0.90 kg) was charged to the reactor. The mixture was stirred at 60-65° C. for 4 h. The mixture was distilled to minimum stir volume in the reactor. The concentrate was charged to another reactor with water (90 kg). The resulting slurry was filtered through a centrifuge filter. The wet cake was charged to a reactor. Methanol (22.5 kg) was charged to the reactor and the mixture stirred at 40-45° C. for 2 h. The slurry was filtered through the centrifuge filter and the filter cake was washed with methanol (4.5 kg). The filter cake was charged to a clean and dry reactor. Silica gel (31 kg) was charged to the reactor. Tetrahydrofuran (19.8 kg) was charged to the reactor and stirred. The slurry was transferred to rotary evaporator vessel and concentrated by rotary evaporation. The mixture was loaded into a silica gel column. The column was eluted consecutively with THF/Hexane (6:4), THF/hexane (8:2) and THF. The fractions collected were analyzed for the product and the fractions containing the product was combined and concentrated. The concentrate was poured into water (45 kg). The resulting suspension was filtered through the centrifuge filter. The filter cake washed with water (9.0 kg) then was dried under vacuum at 40-50° C. for 36 h to afford a mixture of diastereomers 1-((S)-2-(5-(tert-butyl) thiophene-2-carboxamido)-3-(4-(5-((1RS,1'r,4'RS)-4'-ethyl-[1,1'-bi(cyclohexan)]-3-en-4-yl)pyrimidin-2-yl)phenyl)-propanoyl)azetidine-3-carboxylic acid (RP-101 free acid) (as a diastereomeric mixture of RP-103 free acid and RP-104 free acid) (2.8 kg; chemical purity: 95.3% purity, de: 97.2%; 53.3% yield).

The diastereomerically pure RP-103 and RP-104 (free acids) were synthesized in a manner similar to RP-101 free acid using the respective chirally pure boronate esters, 2-((1 S,1'r,4'S)-4'-ethyl-[1,1'-bi(cyclohexan)]-3-en-4-yl)-4,4,5,5-tetramethyl-1,3,2-dioxaborolane and 2-((1R,1'r,4'R)-4'-ethyl-[1,1'-bi(cyclohexan)]-3-en-4-yl)-4,4,5,5-tetramethyl-1,3,2-dioxaborolane that were isolated from preparative chiral chromatography (Chiralcel® OJ-H; methanol/hexane 95/5; ambient temperature; UV detection at 225 nm; peak 1 RT=7.68 min (R, >99% ee), peak 2 RT=8.66 min (S, >97% ee).

Step 5 solution was added to the vessel at a rate of 9.8 mL/minute until a total of 2.6 L had been added. After 60 minutes, the vessel was cooled to 5° C. at a rate of 0.2° C./min and the slurry temperature cycled as follows: 5 to 35 to 5 to 30 to 5° C.; 2.5 hour ramps and 1 hour holds; final cool over 2 hours followed by a hold up to total 24 hours. Filtration of the slurry was done in two lots using a Buchner funnel and 140 and 120 mm diameter and 11 μm filter paper. The filter cake was re-slurried in 3 L heptane before being re-isolated.

Filtration took place over 57 minutes for the two cakes. The cake was washed with 450 mL and 350 mL neat heptane, wash time was 50 minutes for both cakes. Filtration of re-slurred material took place over 20 minutes. The isolated, dried solids of deanol-RP-101 (as a diastereomeric mixture of deanol-RP-103 and deanol-RP-104) had a mass of 319 g, corresponding to a yield (based on expected mass of salt) of 74.44%. The mother liquor concentration was measured to be 23.3 mg/mL, corresponding to a yield of 83.11% (3,100 mL mother liquor recovered). Purity of the mother liquor was found to be 77.4%, and purity of the

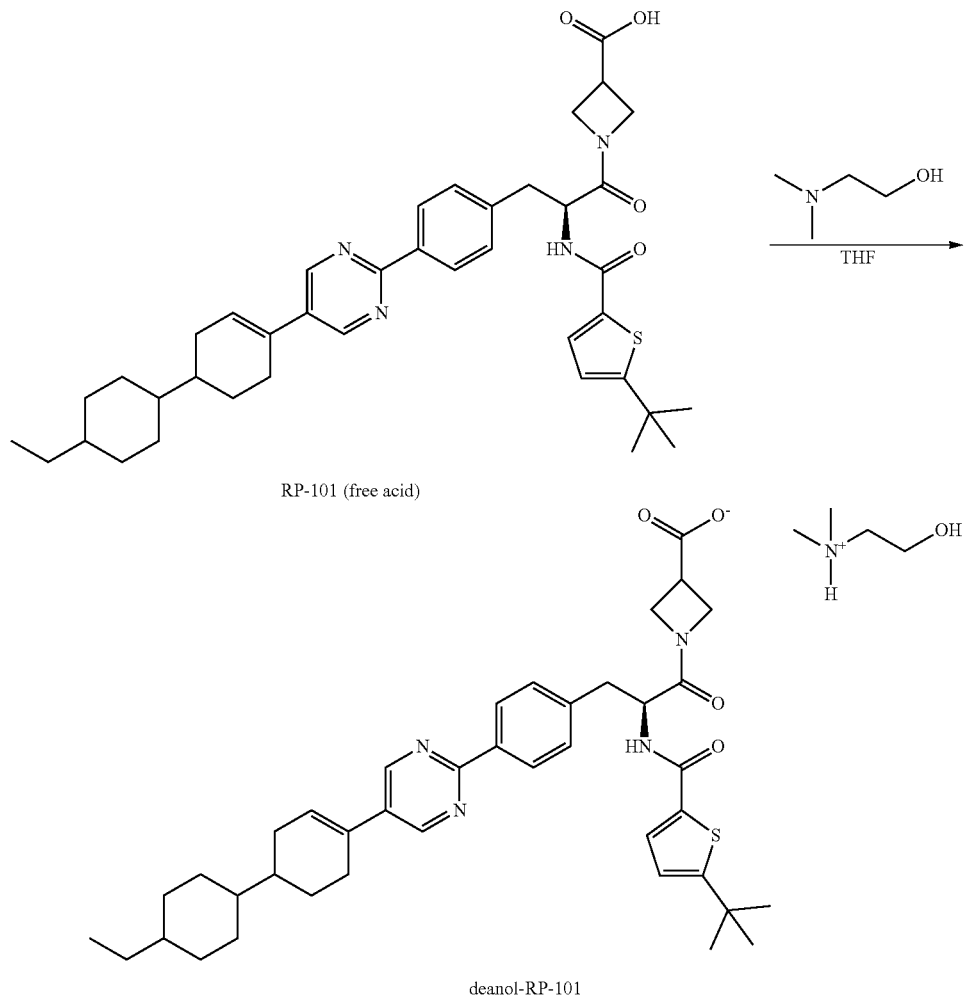

To a 5 L crystallization vessel, 400 g amorphous RP-101 (free acid) was added. RP-101 dissolved readily in 1.8 L THF at 40° C. and stirring at 200 RPM. To this solution was added 261 mL of a deanol solution (25 mg/mL deanol in THF). 4 g of seed material (finally ground deanol-RP-101) was added to this solution. After 10 minute hold, deanol solids was found to be 98.3%. $^1$H NMR (400 MHz, DMSO-$d_6$) δ 8.88 (app d, J=1.8 Hz, 2H), 8.70 (app dd, J=8.3, 2.9 Hz, 1H), 8.27-8.24 (m, 2H), 7.69-7.68 (d, J=3.9 Hz, 1H), 7.41 (d, J=8.0 Hz, 2H), 6.90 (app dd, J=3.9, 1.5 Hz, 1H), 6.42-6.37 (m, 1H), 4.64 (tt, J=9.4, 4.5 Hz, 1H), 4.39 (t, J=8.0 Hz, 0.5H), 4.23 (dd, J=8.7, 6.1 Hz, 0.5H), 4.15-4.10 (m, 1H), 4.07-3.98 (m, 1H), 3.94-3.85 (m, 1H), 3.53 (t, J=8.0 Hz, 2H), 3.29 (ddd, J=15.2, 9.2, 6.0 Hz, 0.5H), 3.16-3.01 (m, 2.5H), 2.57 (t, J=8.0 Hz, 2H), 2.58-2.21 (m, 4H), 2.33 (s, 6H), 1.95-1.90 (m, 2H), 1.79-1.69 (m, 4H), 1.36-1.29 (m, 10H), 1.17-0.81 (m, 12H).

The diastereomerically pure deanol-RP-103 and deanol-RP-104 salts were synthesized from the respective free acids. To a 250 mL crystallization vessel, 5 g amorphous RP-103 or RP-104 (free acid) was added. The free acids dissolved readily in 22.5 mL THF at 40° C. and stirring at 200 RPM. To this solution was added 1.25 equivalents total for RP-103 and 2.0 equivalents total for RP-104 mL of a deanol solution (25 mg/mL deanol in THF). 50 mg of seed material (finally ground deanol-RP-103 or deanol-RP-104 from pilot experiments) was added to this solution. After a 10 minute hold, deanol solution was added to the vessel at a rate of 9.8 mL/hour until the remaining solution had been added. At this point, 20% v/v heptane was added over 1 hour. The vessel was cooled to 5° C. at a rate of 0.2° C./min and the slurry temperature cycled as follows: 5 to 35 to 5 to 30 to 5° C.; 2.5 hour ramps and 1 hour holds; final cool over 2 hours followed by a hold up for 1 hour. Filtration of the slurry was done using a Buchner funnel (80 mm diameter) with 11 μm filter paper. Isolated yields after drying were 5.24 g (93%) for deanol-RP-103 and 4.93 g (92%) for deanol-RP-104.

FIGS. 1A, 2A and 3A are XRPD diffractograms of a deanol-RP-101 (as a diastereomeric mixture of deanol-RP-103 and deanol-RP-104), deanol-RP-103 and deanol-RP-104, respectively, as prepared according to the methods noted above. Similarly, and again as prepared by the methods noted above, FIGS. 1B and 1C identify XRPD peak assignments for deanol-RP-101, FIGS. 2B and 2C identify XRPD peak assignments for deanol-RP-103, and FIGS. 3B and 3C identify XRPD peak assignments for deanol-RP-104.

Example 2

Preparation of Meglumine-RP-101 (Meglumine Salt Form)

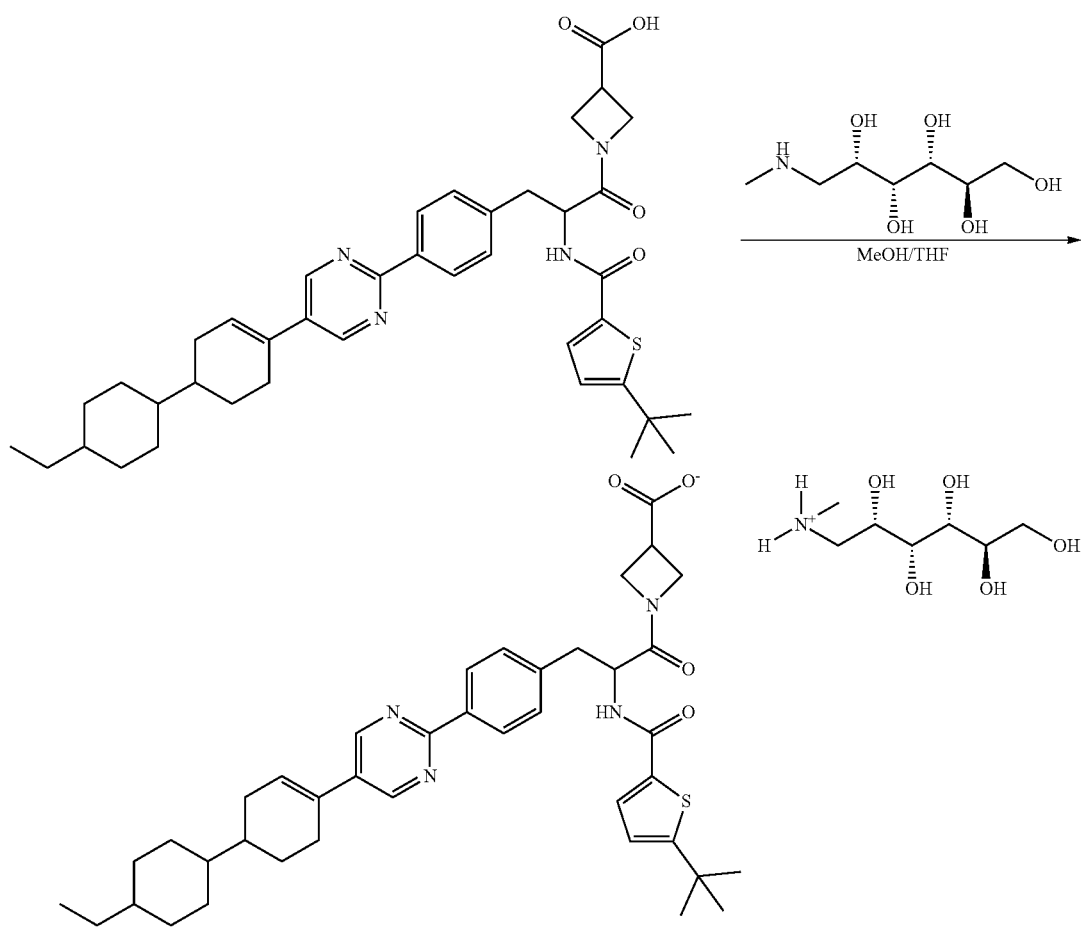

RP-101 (free acid), as a diastereomeric mixture of RP-103 (free acid) and RP-104 (free acid), was prepared according to the synthesis disclosed in Example 1 above. This starting material (16.33 g, 23.85 mmol) and (2R,3R,4R,5S)-6-(methylamino)hexane-1,2,3,4,5-pentaol (4.66 g, 23.85 mmol) were suspended on MeOH (750 ml) and then heated at 55° C. (internal temperature). Solid was still present so more MeOH (1 L) was progressively added until most of the solid went in solution. Because the resulting mixture was still cloudy, THF (inhibitor free, 300 mL) was added and the mixture stirred at the same temperature for 20 min. After cooling, the solution was transferred into a 2 L round bottom flask (in batches) and the solvents evaporated. The solid so obtained was scraped out from the flask and transferred into a beaker to be dried overnight to afford meglumine-RP-101 (18.430 g, 19.94 mmol, 84% yield) as an off white solid.

The product was analyzed by LCMS (Agilent, X-Select, Waters X-Select C18, 2.5 µm, 4.6×30 mm, Acidic (0.1% Formic acid) 15 min method, 5-95% MeCN/water): 1304-48, m/z 683.4 (M+H)$^+$ (ES$^+$) (mass obtained from LCMS lab4) at 10.83 min, 99.8% purity @ 254 nm. The product was analyzed by Chiral HPLC (Diacel Chiralpak IA, 5 um, 4.6×250 mm, 45 min method, 1.0 ml/min, 2-10% EtOH (0.1% TFA) in isohexane/DCM (78.5%/19.5%): RT=20.25 min, 97.7% ee @ 254 nm. $^1$HNMR was consistent with meglumine-RP-101, as a diastereomeric mixture of meglumine-RP-103 and meglumine-RP-104.

This material was then utilized as the starting material for the preparation of the free acid as described in Example 3 below.

Example 3

Preparation of RP-101 (Free Acid Form)

Batch 1: 240 mg of meglumine-RP-101 from Example 2 was added to 25 mL deionised water and stirred for 30 minutes to give a solution with some residual haziness. Formation of a small amount of gel was observed. 1 equivalent of 0.1 M hydrochloric acid (2.7 mL) was added dropwise until pH 5 was obtained. Immediate precipitation of a frothy solid was observed, which resulted in a gel. RP-101 (free acid) was extracted using 20 mL DCM. A change in consistency was observed upon addition of the DCM, resulting in a fine dispersion rather than a gel. The organic layer was evaporated to dryness using a rotary evaporator and the resultant small amount of solid was analyzed by XRPD and $^1$H NMR. The RP-101 (free acid) remaining in the aqueous layer was extracted a second time using 50 mL methylethyl ketone (MEK). The organic layer was dried using magnesium sulfate, filtered, evaporated using a rotary evaporator and the resultant solid was analyzed by $^1$H NMR (ca. 25% yield).

Batch 2: 240 mg meglumine-RP-101 from Example 2 was added to 20 mL deionised water and stirred for 30 minutes to give a solution with some residual haziness. Formation of a small amount of gel was observed. 1.5 equivalents of 0.1 M hydrochloric acid (4.0 mL) were added dropwise to the API until pH 3 was obtained. Immediate precipitation of a frothy solid was observed, which resulted in a gel. RP-101 (free acid) was extracted using 20 mL DCM and 50 mL MEK. A change in consistency was observed upon addition of the DCM, resulting in a fine dispersion rather than a gel. The organic layer was dried using magnesium sulfate, filtered, evaporated to dryness using a rotary evaporator and the resultant solid was analyzed by XRPD and $^1$H NMR (44% yield).

Batch 3: 1.2 g meglumine-RP-101 from Example 2 was added to 100 mL deionised water and stirred for 30 minutes to give a solution with some residual haziness. Formation of a small amount of gel was observed. 1.35 equivalents of 0.1 M hydrochloric acid (18.0 mL) were added dropwise until pH 3 was obtained. Immediate precipitation of a frothy solid was observed, which resulted in a gel. 50 mL DCM were added and the sample stirred for 20 minutes resulting in a clear aqueous layer and a turbid, yellow organic layer. Formation of some gel was observed. RP-101 (free acid) was extracted using 250 mL MEK. The organic layer was dried using magnesium sulfate, filtered, evaporated to dryness using a rotary evaporator and the resultant solid was analyzed by $^1$H NMR.

The following methods of analysis were employed in this and the following examples.

Example 4

Solvent Solubility 20 mg of RP-101 (Batch 2 of Example 3) was placed in each of 12 vials and 5 volume aliquots of the appropriate solvent systems were added to the appropriate vial (see Table 2). Between each addition, the mixture was checked for dissolution and, if no dissolution was apparent, the next aliquot of solvent was added. This procedure was continued until dissolution was observed or until 100 volumes of solvent had been added.

TABLE 2

| | Solvent |
|---|---|
| 1 | Acetone |
| 2 | Acetonitrile |
| 3 | Dichloromethane |
| 4 | Diisopropyl ether |
| 5 | 1,4-Dioxane |
| 6 | Ethanol |
| 7 | Ethyl acetate |
| 8 | Methanol |
| 9 | Methylethyl |
| 10 | tert -Butylmethyl |
| 11 | Tetrahydrofuran |
| 12 | Toluene |

Example 5

Salt Screen 40 mg of RP-101 (Batch 3 of Example 3) was dissolved or suspended in 200 µL to 1 mL solvent (see Table 3). Counterions (see Table 4) were added at room temperature and the samples observed for precipitation.

Liquid counterion (choline hydroxide, 46% solution by weight in water) was added as an aqueous stock solution.

Solid counterions were suspended in 200 µL or 300 µL solvent and the resultant slurry was added.

One blank sample (RP-101 only, no counterion) was carried out in each solvent.

These resultant suspensions were temperature cycled between ambient temperature (22° C.) and 40° C. in 4 hour cycles for 72 hours. Samples were analyzed by XRPD and any remaining solid was isolated by filtration using a centrifuge and tubes with a 0.45 m filter insert. Isolated solids were allowed to dry at ambient condition and analyzed by $^1$H NMR. Any resultants salts were stored at 40° C./75% relative humidity (RH) for 7 days and re-analyzed by XRPD.

TABLE 3

| | Solvent |
|---|---|
| 1 | Dichloromethane |
| 2 | 1,4-Dioxane |
| 3 | Methyl ethyl ketone |

TABLE 4

| No. | Base | pKa 1 | pKa 2 | pKa 3 | LogP | MW [g/mol] |
|---|---|---|---|---|---|---|
| 1 | Sodium hydroxide | 14.00 | — | — | | 40.00 |
| 2 | Choline hydroxide | 11.00 | — | — | −3.70 | 121.18 |
| 3 | L-Lysine | 10.79 | 9.18 | 2.16* | −1.04 | 146.19 |
| 4 | N-Methylglucamine | 8.03 | — | — | −3.37 | 195.22 |

Example 6

Thermodynamic Solubility Testing pH 6.8 phosphate buffer was prepared by adding 11.2 mL 0.2 M potassium phosphate monobasic to 25 mL 0.2 M sodium hydroxide and diluting the resulting solution to 100 mL. 0.5 mL of that buffer is then added to 5-10 mg of each crystalline salt hit. The pH of the resultant slurries are measured after 10 minutes and, if needed, adjusted back to pH 6.8 using the individual buffer component. Samples were stirred at room temperature for 24 hours, filtered, and analyzed for concentration by HPLC.

Example 7

Characterization of Meglumine-RP-101

Figure 5:
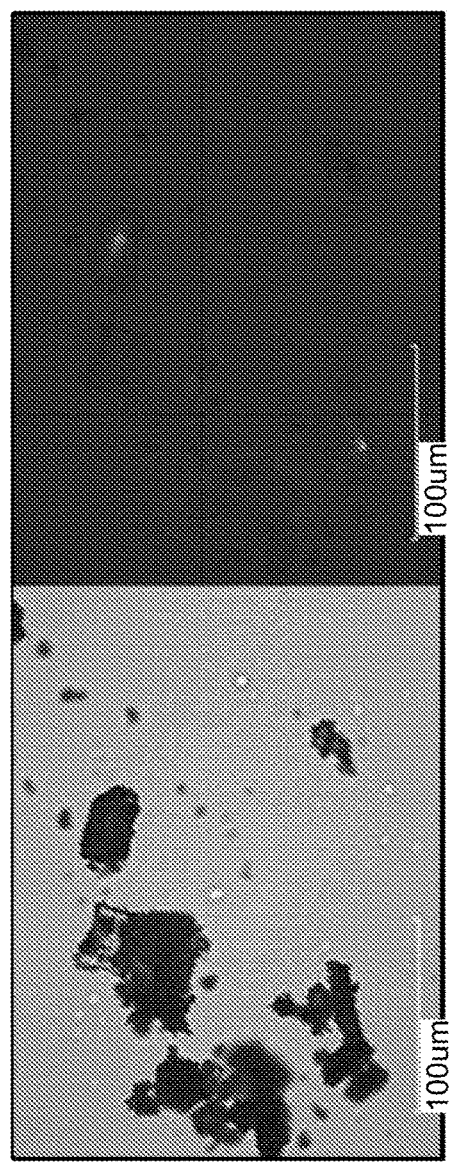
FIG. 5 shows PLM images of meglumine-RP-101.
Figure 6:
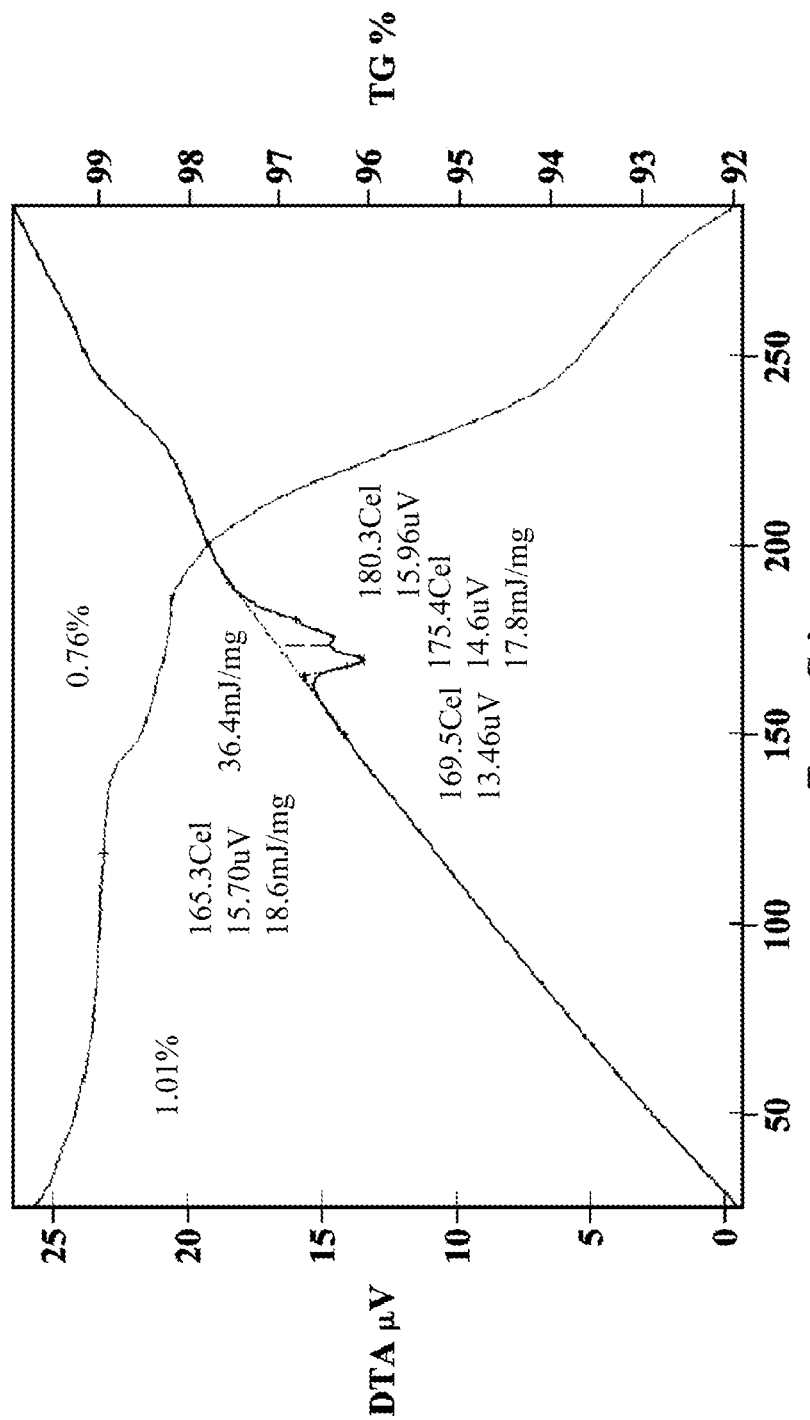
FIG. 6 shows a TGA thermogram of meglumine-RP-101.
Figure 7:
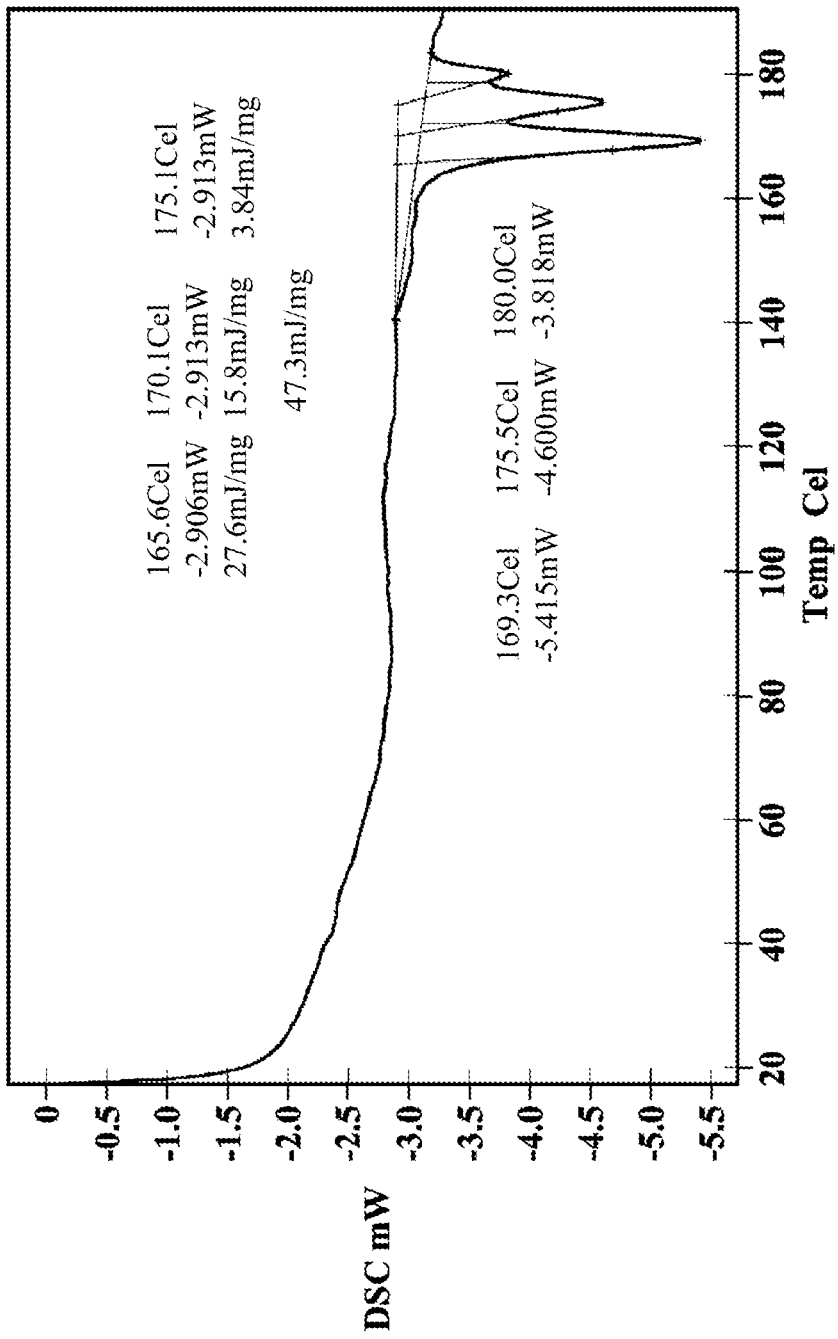
FIG. 7 shows a DSC diffractogram of meglumine-RP-101.

Meglumine-RP-101 of Example 2 appeared amorphous by XRPD (FIG. 4) and PLM (FIG. 5), slightly "wet" by TGA (FIG. 6), and showed no significant thermal events below about 150° C. by DSC (FIG. 7). A $^1$H-NMR spectrum was obtained for reference. In summary, meglumine-RP-101 was found to be:
  Predominately amorphous with a few broad peaks and an amorphous halo around 18° 20 observed by XRPD.
  Mixture of glass-like particles and opaque agglomerates observed by PLM (only a few particles exhibited partial birefringence).
  TGA showed an initial weight loss of 1.0% up to 115° C. 0.8% weight loss was observed from 115° C. to 190° C., coinciding with a series of weakly overlapping endothermic events at 169.5° C., 175.4° C. and 180.3° C. (peak temperatures). Only the onset temperature of the first endothermic event at 165.3° C. could be determined accurately due to the overlap. The sample decomposed thereafter.
  DSC confirmed the presence of 3 endothermic events at 165.6° C. (peak 169.3° C.), 170.1° C. (peak 175.5° C.) and 175.1° C. (peak 180.0° C.).

Example 8

Characterization of RP-101 (Free Acid Form)

A comparison of $^1$H NMR spectra for meglumine-RP-101 of Example 2 and all 3 batches of RP-101 of Example 3 showed prominent shift in signal position between 3.8 ppm to 4.8 ppm. Absence of meglumine signals at 3.4 ppm to 3.7 ppm confirms successful removal of the counterion.

Example 9

Salt Screen

RP-101 formed salts with all four bases (sodium hydroxide, choline hydroxide, L-lysine and meglumine) from three different solvents (dichloromethane (DCM), 1,4-dioxane and methyethyl ketone (MEK)) as summarized below:

Sodium Salt

Figure 8:
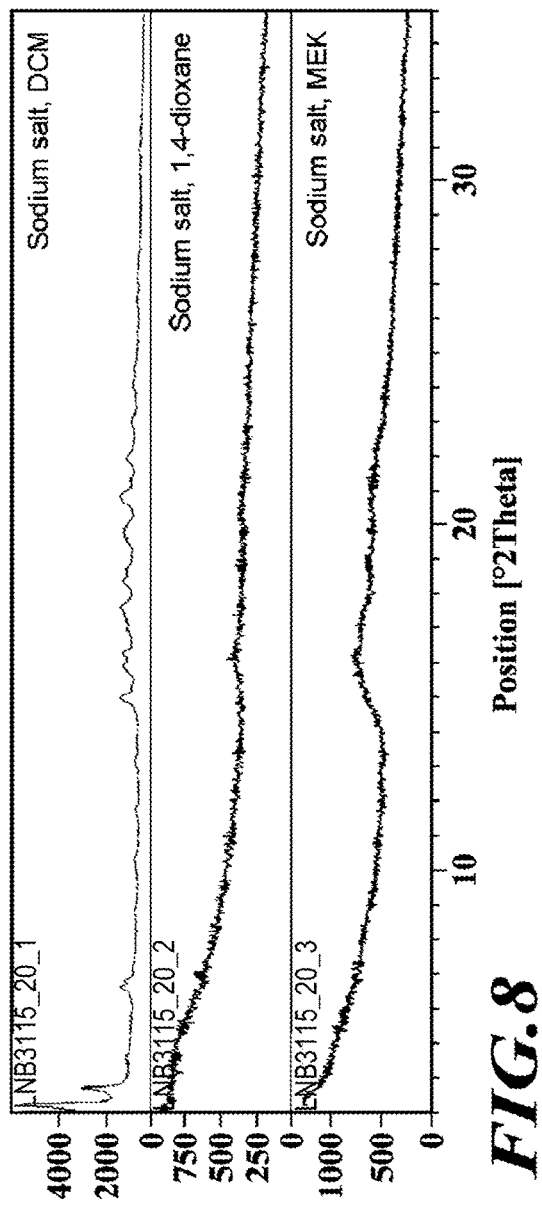
FIG. 8 shows XRPD diffractograms of the sodium salt.
Figure 9:
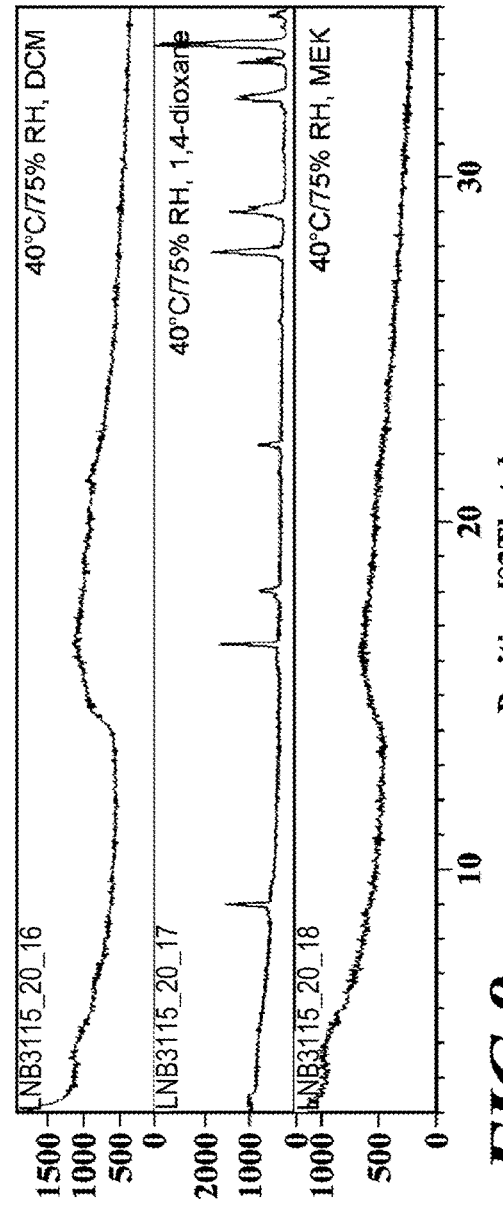
FIG. 9 shows XRPD diffractograms of the sodium salt after 7 days.

A significantly amorphous (partially crystalline) sodium salt was obtained from DCM, and amorphous sodium salts were obtained from 1,4-dioxane and MEK (FIG. 8), as summarized below:
  $^1$H NMR confirmed the salt formation from all 3 solvents.
  The sodium salt obtained from DCM showed a slight increase in crystallinity compared to the amorphous salts obtained from 1,4-dioxane and MEK.
  The sodium salt did not appear stable at 40° C./75% RH, the sample from DCM turned amorphous after 7 days, and a crystalline species (other than sodium-RP-101) appeared after storage of the amorphous salt from 1,4-dioxane (FIG. 9).
  The sodium salt obtained from DCM did not show defined morphology by PLM and had only weak birefringence.
  The sodium salt obtained from DCM turned completely amorphous after 7 days at 40° C. and 75% RH.
  Solubility at pH 6.8 was measure to as 0.255 mg/mL for the material from DCM, and 0.144 mg/mL from the material from MEK (see Table 5 below).

Choline Salt

Figure 10:
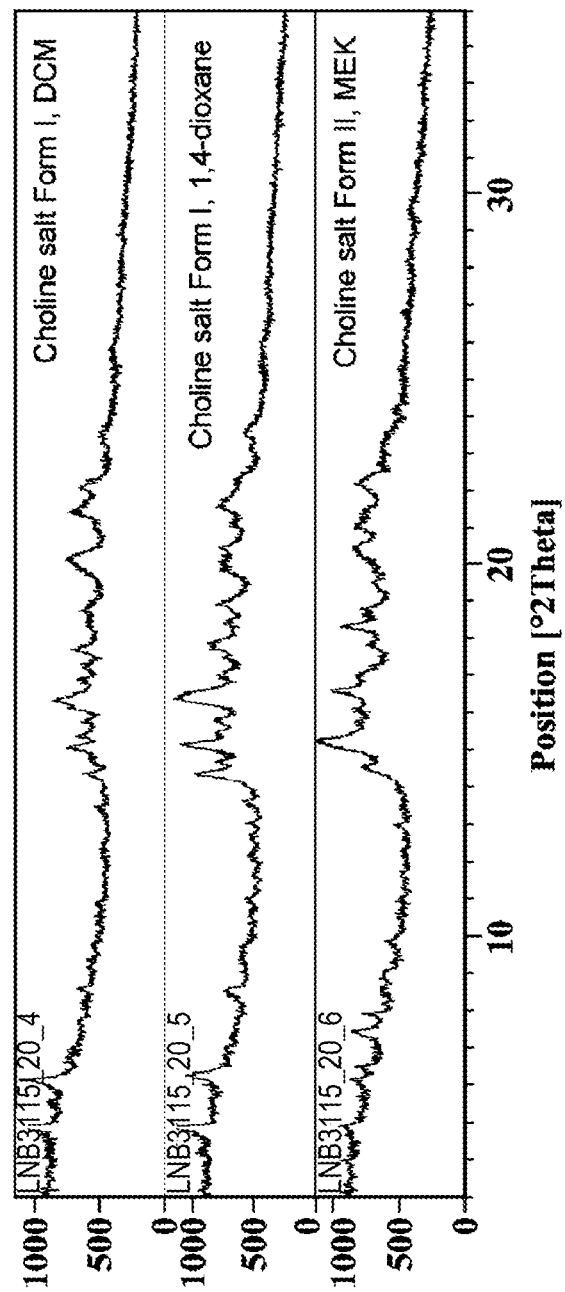
FIG. 10 shows XRPD diffractograms of the choline salt.
Figure 11:
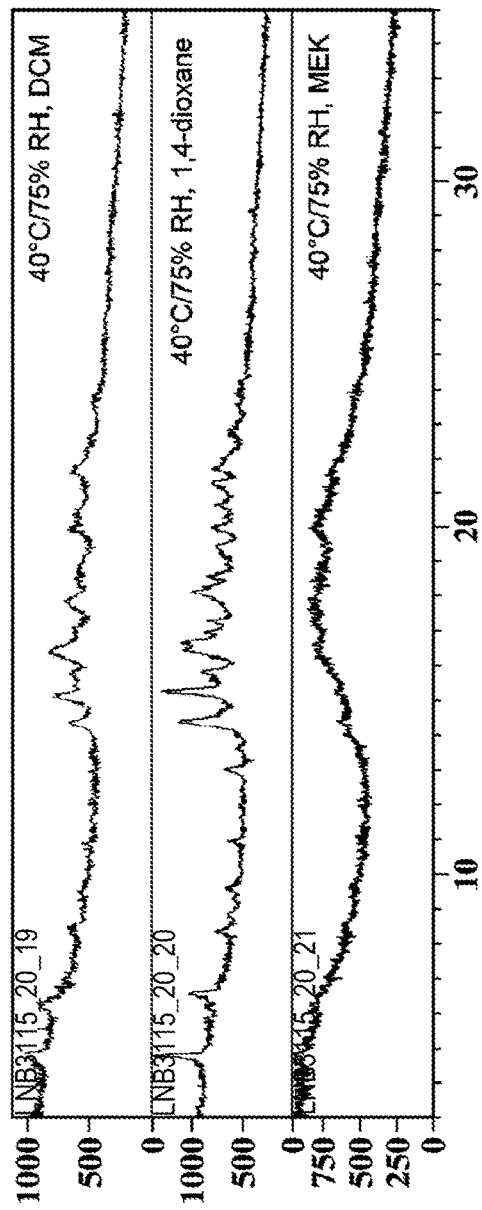
FIG. 11 shows XRPD diffractograms of the choline salt after 7 days.

Two weakly crystalline choline salts were obtained, one form (Form I) from DCM and 1,4-dioxane, and another form (Form II) from MEK (FIG. 10), as summarized below:
  $^1$H NMR confirmed salt formation for both forms based on the shift in signal positions from 4.5 ppm to 3.8 ppm compared to the free acid of RP-101.
  Opaque agglomerates without distinct crystalline morphology and no birefringence were observed in both forms.
  Form I had 7.3% weight loss up to 80° C. followed by a further 3.0% loss up to 160° C. Two weak endothermic events were observed at 200° C. and 214° C., coinciding with a 10.0% weight loss.
  Form II had 2.9% weight loss up to 90° C. and no significant further loss up to 140° C. Two weak endothermic events were observed at 213° C. and 235° C., coinciding with a 12.3% loss
  Form I appeared more stable than Form II upon stability stress testing (FIG. 11). Form II turned amorphous after 7 days (40° C./75% RH). No change in crystalline form and no significant decrease in crystallinity were observed for Form I obtained from DCM. A partial conversion of Form I obtained from 1,4-dioxane to Form II was observed.
  Solubility at pH 6.8 was measured as 0.034 mg/mL for Form I, and 0.001 mg/mL for Form II (see Table 5 below).

L-Lysine Salt

Figure 12:
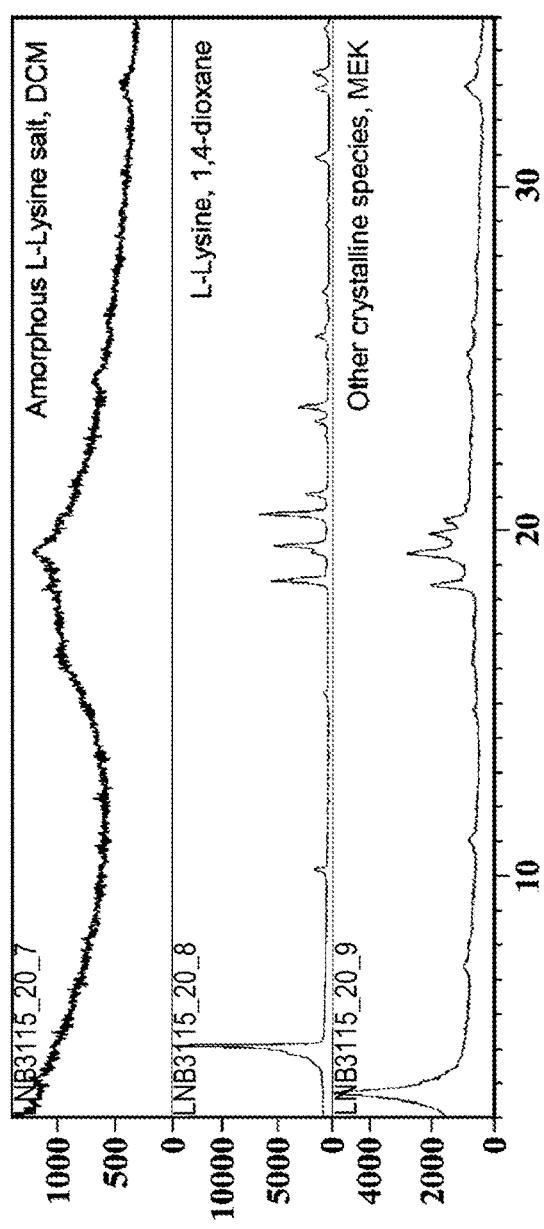
FIG. 12 shows XRPD diffractograms of the L-lysine salt.
Figure 13:
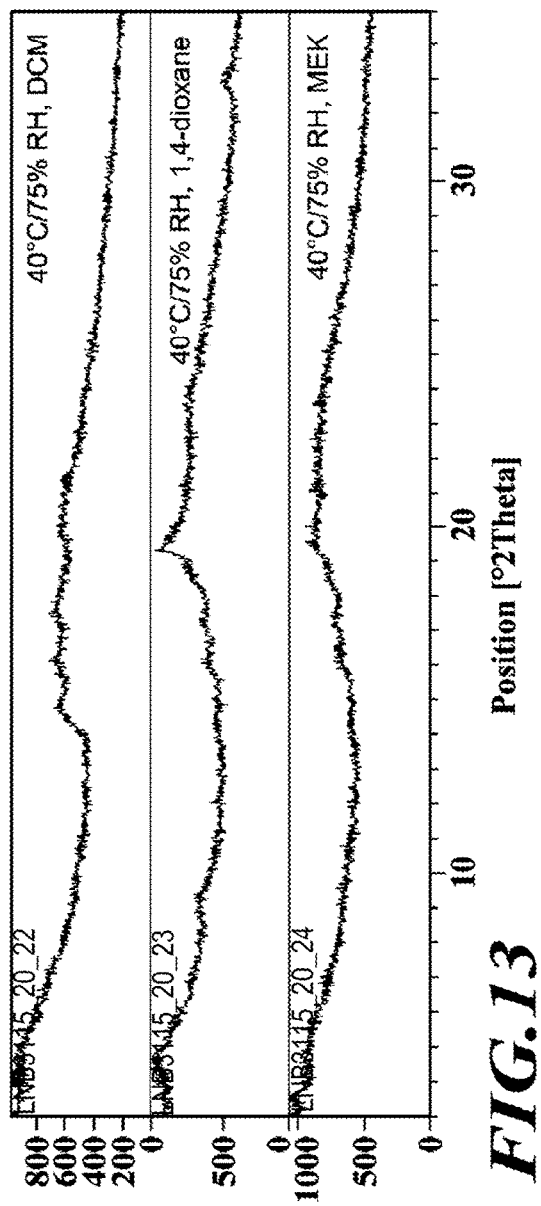
FIG. 13 shows XRPD diffractograms of the L-lysine salt after 7 days.

An amorphous L-lysine salt was obtained from DCM (FIG. 12). 1,4-dioxane did not yield a salt of RP-101. While a crystalline species was observed in MEK, $^1$H NMR indicated the species was not a salt of L-lysine.
  TG/DTA of the amorphous salt from DCM showed a weight loss of 6.8%, starting from ambient temperature, with no thermal events up to 180° C. A further 10.1% loss took place up to ca. 260° C., coinciding with a broad endothermic trough from 180.1° C. to 240.5° C.
  The salt from DCM remained amorphous upon stability stress testing at 40° C./75% RH (FIG. 13).
  Solubility at pH 6.8 was measured as 0.031 mg/mL for the amorphous L-lysine salt obtained from DCM (see Table 5 below).

Meglumine Salt

Figure 14:
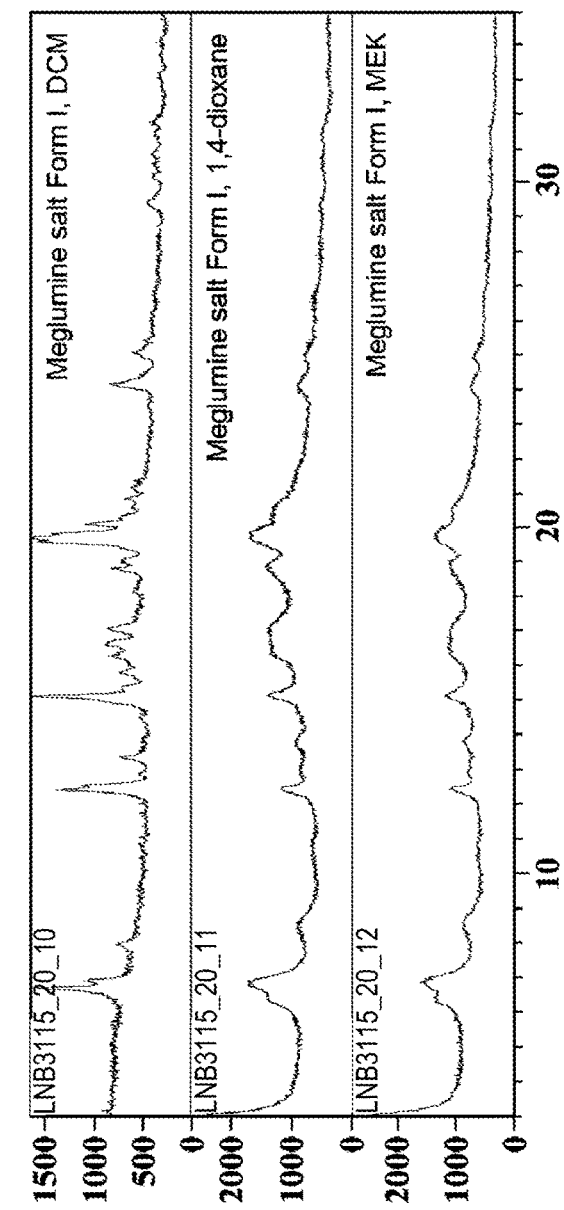
FIG. 14 shows XRPD diffractograms of the meglumine salt.

The same crystalline form of meglumine salt was obtained from all 3 solvents screened, and identical to the crystalline form of the meglumine salt of Example 1. A weakly crystalline material was obtained from DCM, while the material from 1,4-dioxane and MEK appeared predominantly amorphous (FIG. 14).

$^1$H-NMR confirmed salt formation.

Large but poorly defined triangular prisms were observed in the salt obtained from DCM. The prisms exhibited birefringence, while smaller particles attached to the main crystal did not exhibit a great degree of birefringence.

Figure 15:
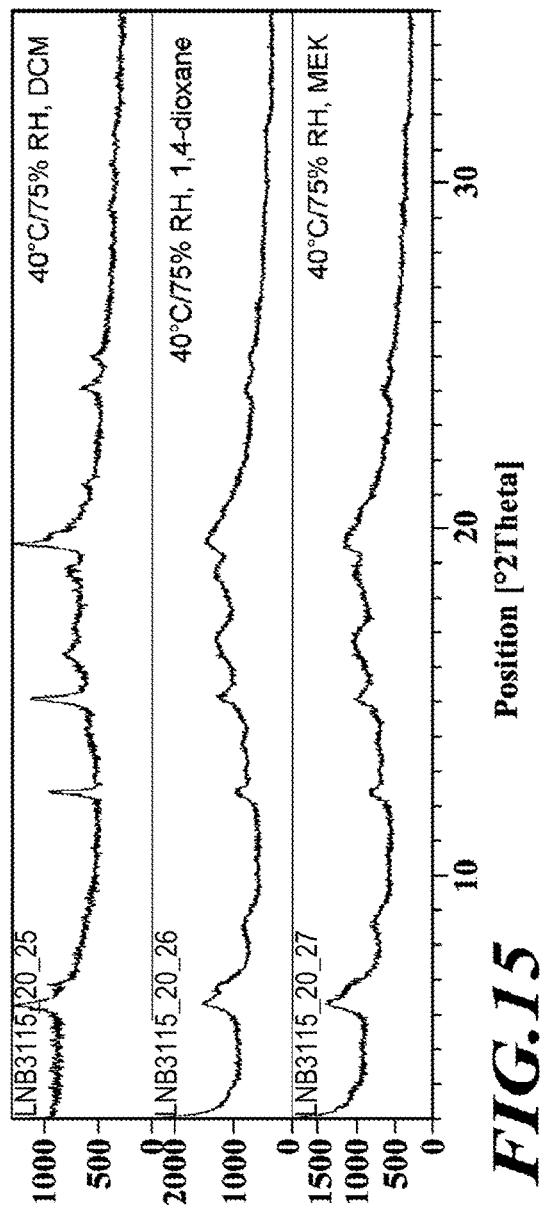
FIG. 15 shows XRPD diffractograms of the meglumine salt after 7 days

A decrease in crystallinity was noted in the weakly crystalline material from DCM after storage at 40° C./75% RH (FIG. 15). Only small changes were noted in the predominantly amorphous material from 1,4-dioxane and MEK.

Solubility at pH 6.8 was measured as 0.160 mg/mL for the weakly crystalline material from DCM, and 0.303 for the material from 1,4-dioxane (see Table 5 below).

Solubility

As reported in Table 5, the aqueous solubility (at pH 6.8, mg/mL) for the salts discussed above were found to be very low.

TABLE 5

| Salt | Solubility (mg/mL) |
| --- | --- |
| Sodium (DCM) | 0.255 |
| Sodium (MEK) | 0.144 |
| Choline (Form I) | 0.034 |
| Choline (Form II) | 0.001 |
| L-Lysine (DCM) | 0.031 |
| Meglumine (DCM) | 0.160 |
| Meglumine (1,4-dioxane) | 0.303 |

Example 10

Salt Screen

Figure 16:
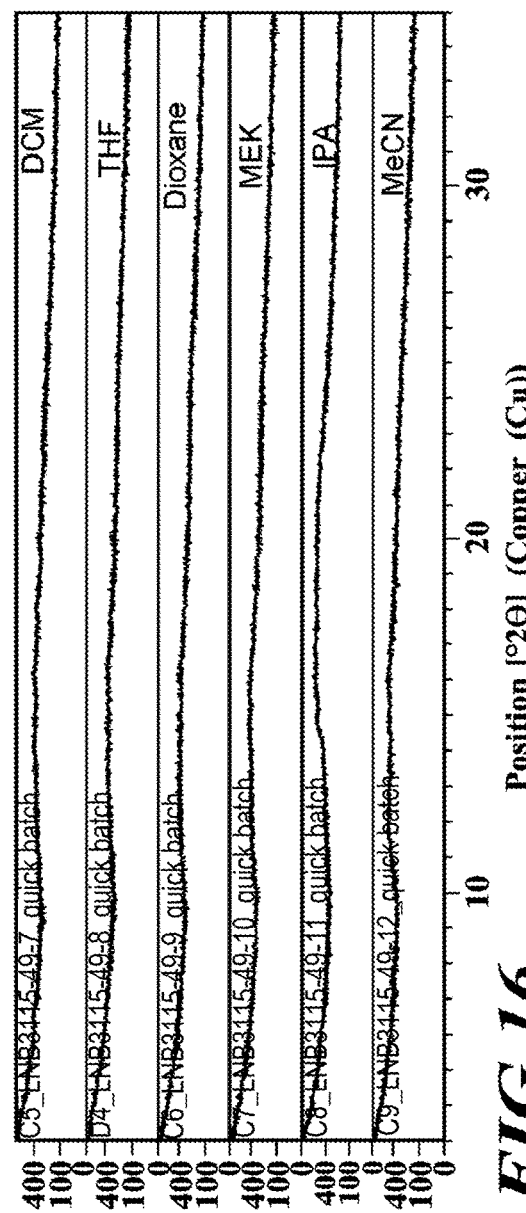
FIG. 16 shows XRPD diffractograms of the arginine salt.

Further salt screening was performed using the optimized parameters identified during the initial experiments as described above; namely, all agitation was performed by way of magnetic flea, salt formation as performed at either 20 or 40 mg scale, and 1 equivalent of counter ion was added. By these methods, the following additional salts were analyzed:

Arginine:

The arginine was pre-dissolved in methanol/water (181 mg in 2 mL) to form a stock solution, which was added (113.8 µL) to RP-101 (40 mgs in 1.5 mL of relevant solvent) which formed solution/slurry depending on solubility of system. The samples were held at 40° C. for 72 hours to maximize the chance of salt formation (increase of kinetics and solubility of system). The resulting solids were analyzed by XRPD to determine crystallinity (FIG. 16), which showed all samples to be amorphous. The samples were re-analyzed after 1 week and no increase in crystallinity was seen.

Figure 17:
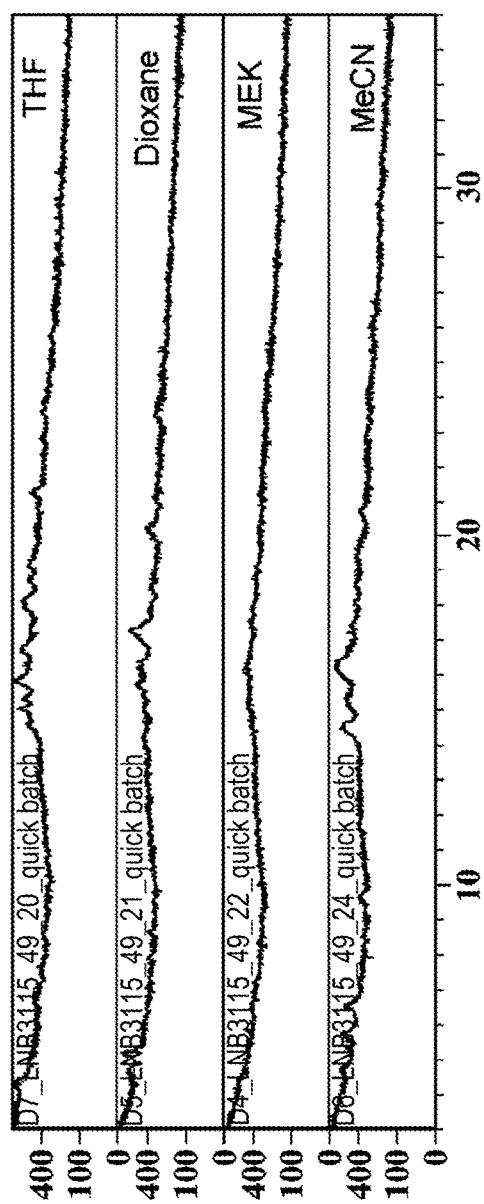
FIG. 17 shows XRPD diffractograms of the benzathine salt.

Benzathine:

The benzathine was pre-dissolved in methanol (450 mg in 2 mL) to form a stock solution, which was added (62.6 µL) to RP-101 (40 mgs in 1.5 mL of relevant solvent) which formed solution/slurry depending on solubility of system. The samples were held at 40° C. for 72 hours to maximize the chance of salt formation (increase of kinetics and solubility of system). The resulting solids were analyzed by XRPD to determine crystallinity (FIG. 17), which showed a number of samples with signs of crystallinity. No further crystal forms were obtained with longer slurrying, with sample from THF being most crystalline. The key solids were analyzed by PLM to help further understanding, which showed birefringence for all three samples. Although birefringence was seen, the particles were very small.

Figure 18:
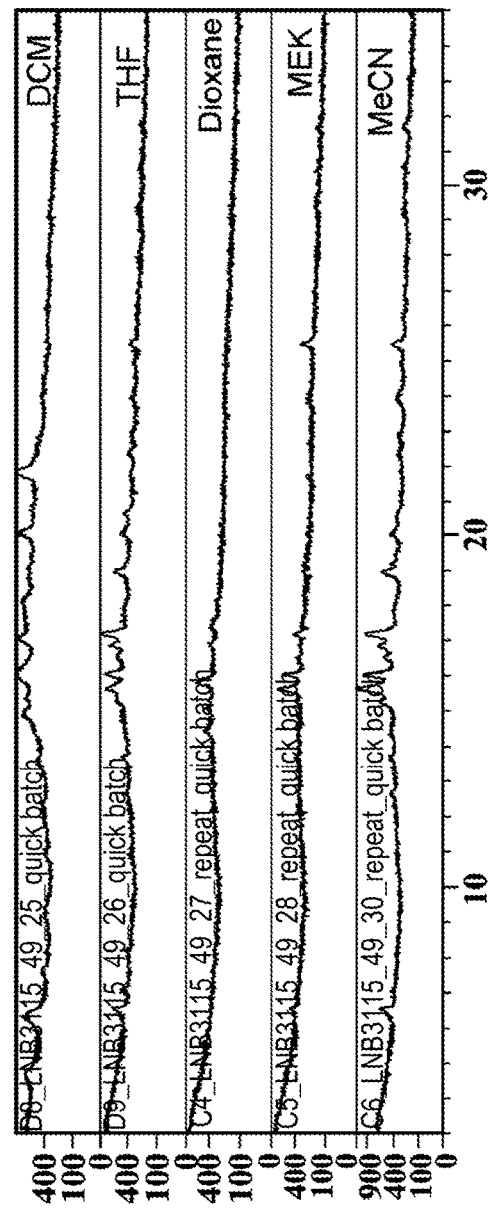
FIG. 18 shows XRPD diffractograms of the dimethylaminoethanol salt.

Dimethylaminoethanol:

The dimethylaminoethanol was pre-dissolved in methanol (445 mg in 2 mL) to form a stock solution, which was added (23.6 µL) to RP-101 (40 mgs in 1.5 mL of relevant solvent) which formed solution/slurry depending on solubility of system. The samples were held at 40° C. for 72 hours to maximize the chance of salt formation (increase of kinetics and solubility of system). The resulting solids were analyzed by XRPD to determine crystallinity and were shown to be amorphous. It was only when they were re-analyzed after 1 week, was crystalline material seen (FIG. 18). For reference both DCM and THF formed clear solutions, where the solvent was allowed to evaporate. This highlights the slow kinetics of the salt formation and crystallization process for this molecule. The solids of interest were analyzed by PLM, where all solids bar from DCM and dioxane showed clear birefringence. There were also some signs of definite morphology being present.

Figure 19:
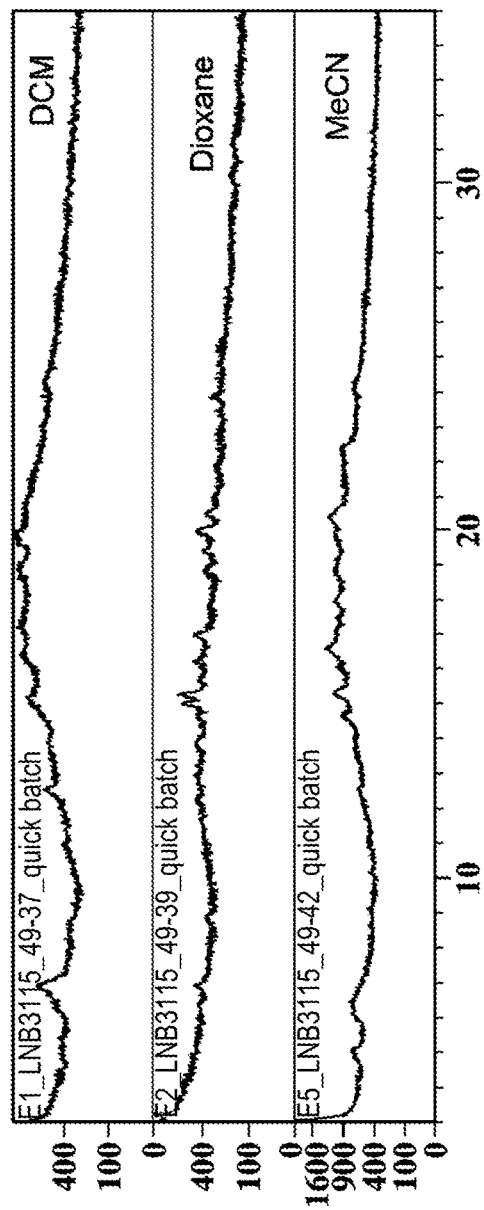
FIG. 19 shows XRPD diffractograms of the N-methylglucamine salt.

N-Methylglucamine:

The N-methylglucamine was pre-dissolved in methanol (183 mg in 2 mL) to form a stock solution, which was added (125.4 µL) to RP-101 (40 mgs in 1.5 mL of relevant solvent) which formed solution/slurry depending on solubility of system. The samples were held at 40° C. for 72 hours to maximize the chance of salt formation (increase of kinetics and solubility of system). The resulting solids were analyzed by XRPD to determine crystallinity and were shown to have signs of crystallinity (FIG. 19). No improvement was seen for longer slurrying. The key solids were characterized by PLM and only the solid from acetonitrile showed any signs of birefringence. The remaining solids showed no obvious birefringence.

Figure 20:
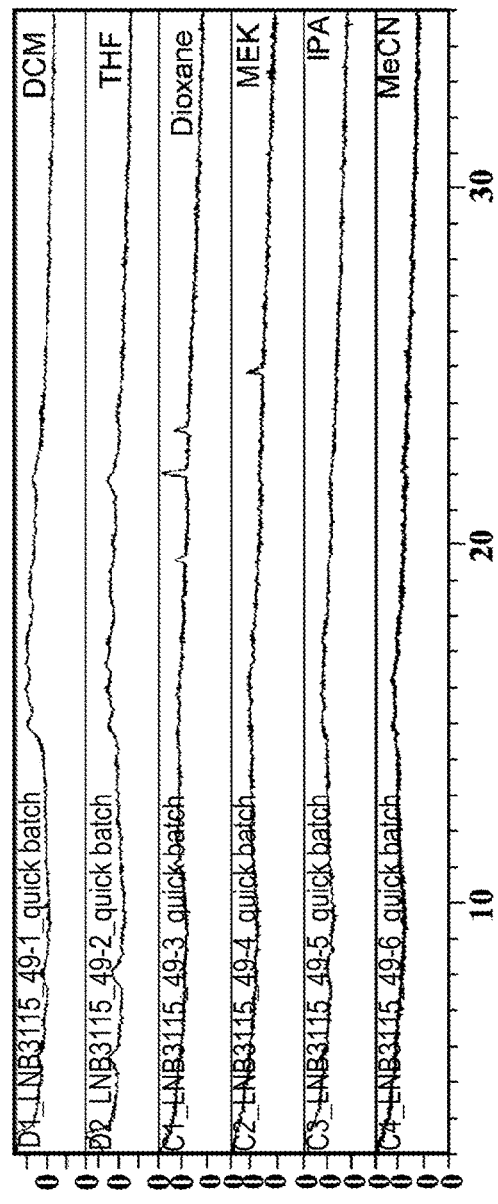
FIG. 20 shows XRPD diffractograms of the potassium hydroxide salt.

Potassium Hydroxide (KOH):

The KOH was pre-dissolved in water (200 mg in 2 mL) to form a stock solution, which was added (33.0 µL) to RP-101 (40 mgs in 1.5 mL of relevant solvent) which was dissolved or suspended, depending on solubility of system. The samples were held at 40° C. for 72 hours to maximize the chance of salt formation (increase of kinetics and solubility of system). The resulting solids were analyzed by XRPD (FIG. 20), which showed all solids exhibited significantly amorphous (partially crystalline) behavior, with minor improvement in crystallinity for longer slurrying. Analysis of the solids by PLM showed differences in particle size and shape, with none exhibiting clear birefringence.

Magnesium:

To see if a suitable magnesium salt could be isolated a salt switch (from potassium) experiment was performed. This was necessary due to the limited solubility of magnesium hydroxide. Potassium hydroxide solution (200 in 2 mL of water) was made up, and added (33.0 µL) to RP-101 (40 mgs in 1.5 mL of solvent). A stock solution of magnesium acetate (156 mgs in 2 mL of methanol/water) was made up and added to the potassium salt. The sample was stirred at 40° C. for 72 hours, at which point the solids were analyzed by XRPD (FIG. 21), with only minor improvements in crystallinity for longer slurrying.

Piperazine:

The piperazine was pre-dissolved in methanol (171 mg in 2 mL) to form a stock solution, which was added (59.2 µL) to RP-101 (40 mgs in 1.5 mL of relevant solvent) which was dissolved or suspended, depending on solubility of system. The samples were held at 40° C. for 72 hours to maximize the chance of salt formation (increase of kinetics and solubility of system). The resulting solids were analyzed by XRPD (FIG. 22), which showed some signs of crystallinity, with only minor improvements in crystallinity with longer slurrying. Both DCM and MEK showed signs of birefringence, with solid from MEK having some potential signs of morphology.

Figure 23:
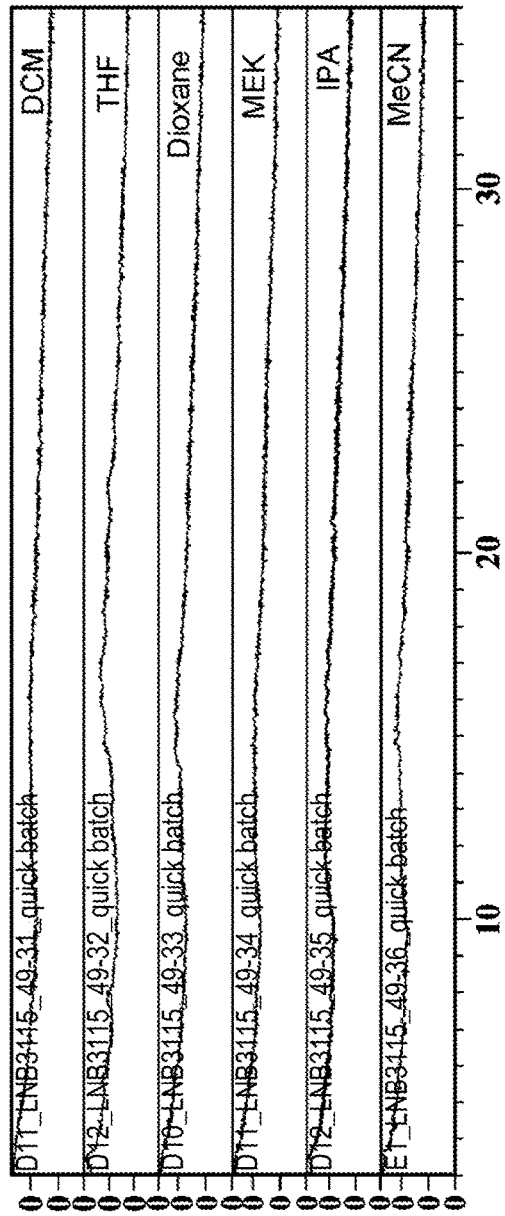
FIG. 23 shows XRPD diffractograms of the tromethamine salt.

Tromethamine:

The tromethamine was pre-dissolved in methanol (133 mg in 2 mL) to form a stock solution, which was added (107.0 µL) to RP-101 (40 mgs in 1.5 mL of relevant solvent) which was dissolved or suspended, depending on solubility of system. The samples were held at 40° C. for 72 hours to maximize the chance of salt formation (increase of kinetics and solubility of system). The resulting solid was analyzed by XRPD (FIG. 23), which showed solids were mainly amorphous, with no improvement with longer slurrying.

Figure 24:
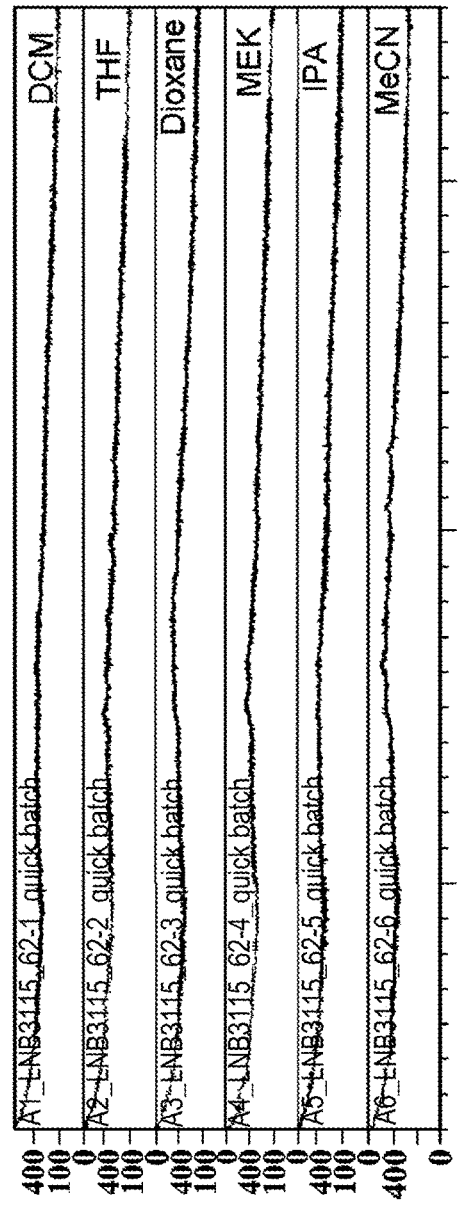
FIG. 24 shows XRPD diffractograms of the sodium hydroxide salt.

Sodium Hydroxide (NaOH):

The NaOH was pre-dissolved in water (188 mg in 1 mL) to form a stock solution, which was added (6.2 µL) to RP-101 (20 mgs in 1 mL of relevant solvent) which dissolved or suspended, depending on solubility of system. The samples were held at 40° C. for 1 week to maximize the chance of salt formation (increase of kinetics and solubility of system). The resulting solids were analyzed by XRPD (FIG. 24), which showed all solids were amorphous. No improvement was seen for longer slurrying with a number of gels seen. This is likely to be related to the presence of water in the system.

Figure 25:
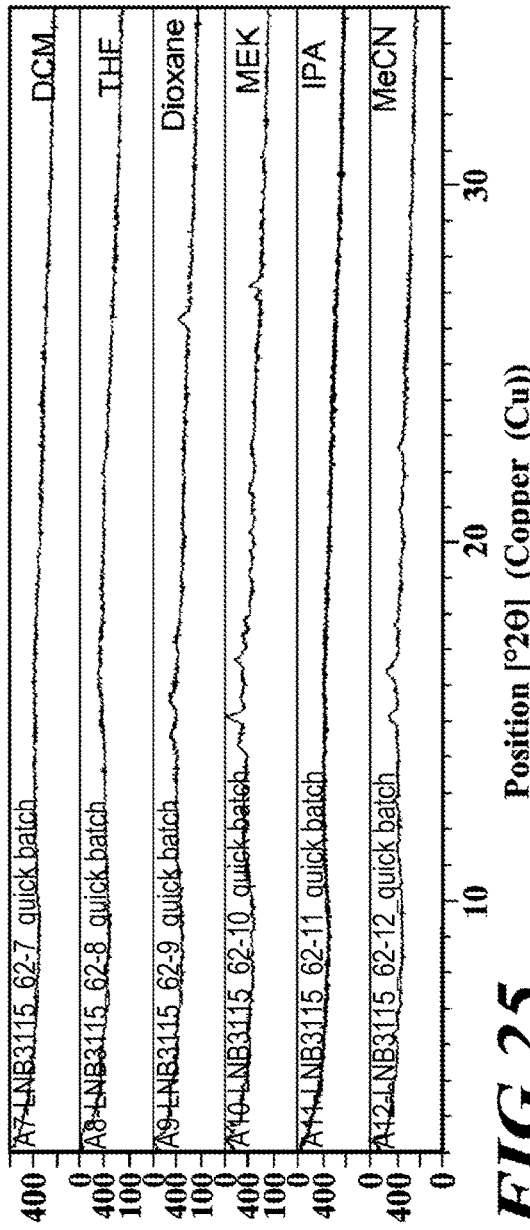
FIG. 25 shows XRPD diffractograms of the calcium salt.

Calcium:

Owing to the limited solubility of calcium hydroxide attempts to make calcium salts were conducted using a more soluble calcium salt input (acetate) and exchange reaction via the sodium salt. Sodium hydroxide solution (188 mg in 1 mL of water) was made up, and added (6.2 µL) to RP-101 (20 mgs in 1 mL of solvent). A stock solution of calcium acetate hydrate (72 mgs in 2 mL of methanol/water) was made up and added to the sodium salt. The sample was stirred at 40° C. for 1 week, at which point the solids were analyzed by XRPD (FIG. 25), with only minor improvements in crystallinity for longer slurrying.

Figure 26:
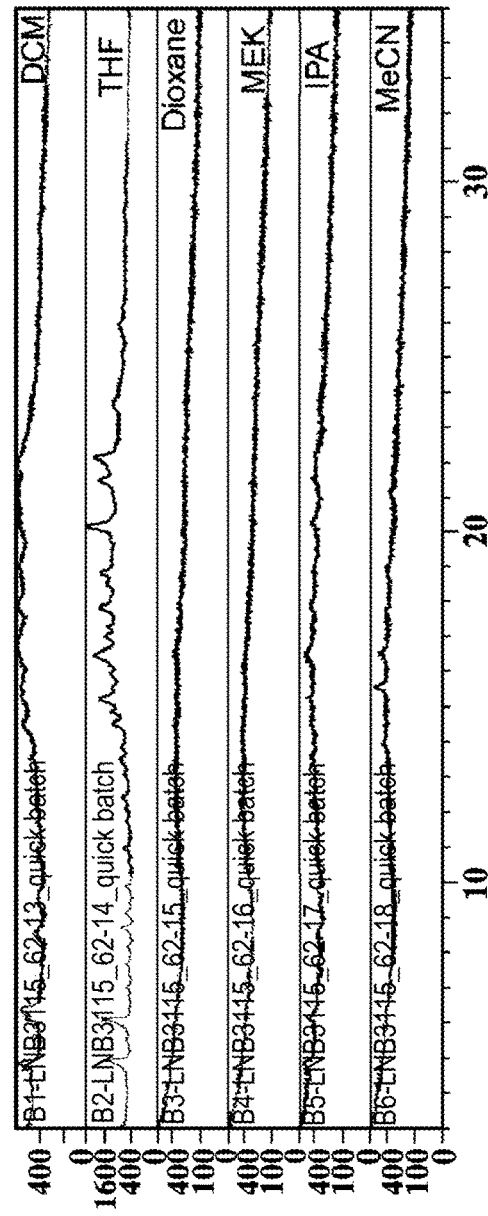
FIG. 26 shows XRPD diffractograms of the choline salt.

Choline:

The choline hydroxide was added neat (8.4 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solids were analyzed by XRPD (FIG. 26), which showed the majority of solids had signs of crystallinity with solid from THF being partially crystalline. Minor improvements were seen for slurrying longer.

Figure 27:
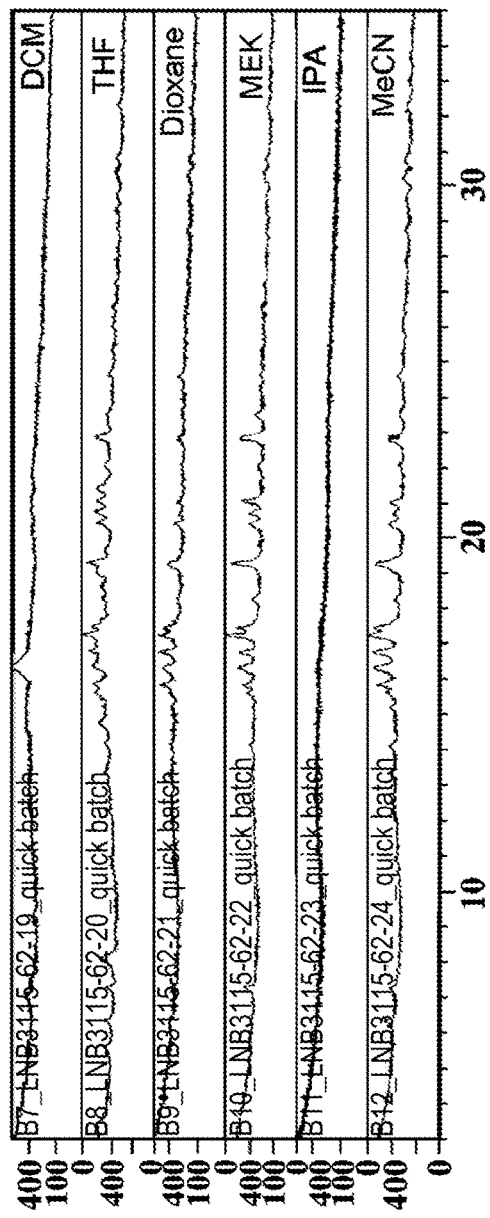
FIG. 27 shows XRPD diffractograms of the diethylamine salt.

Diethylamine:

The diethylamine was pre-dissolved in methanol (307 mg in 1 mL) to form a stock solution, which was added (7.0 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solid was analyzed by XRPD (FIG. 27), which showed a crystalline form, which was improved with longer slurrying.

Figure 28:
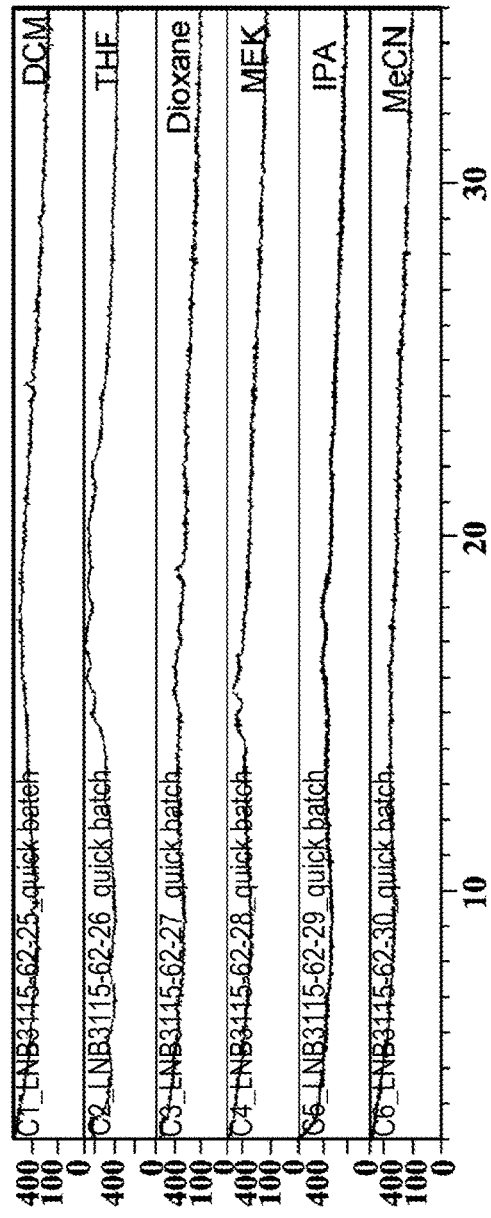
FIG. 28 shows XRPD diffractograms of the L-lysine salt.

L-Lysine:

The L-lysine was pre-dissolved in 50/50 methanol/water mix (56 mg in 1 mL) to form a stock solution, which was added (76.4 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solid was analyzed by XRPD (FIG. 28), which showed that only hints of crystallinity were seen, with no improvement with longer slurrying.

Figure 29:
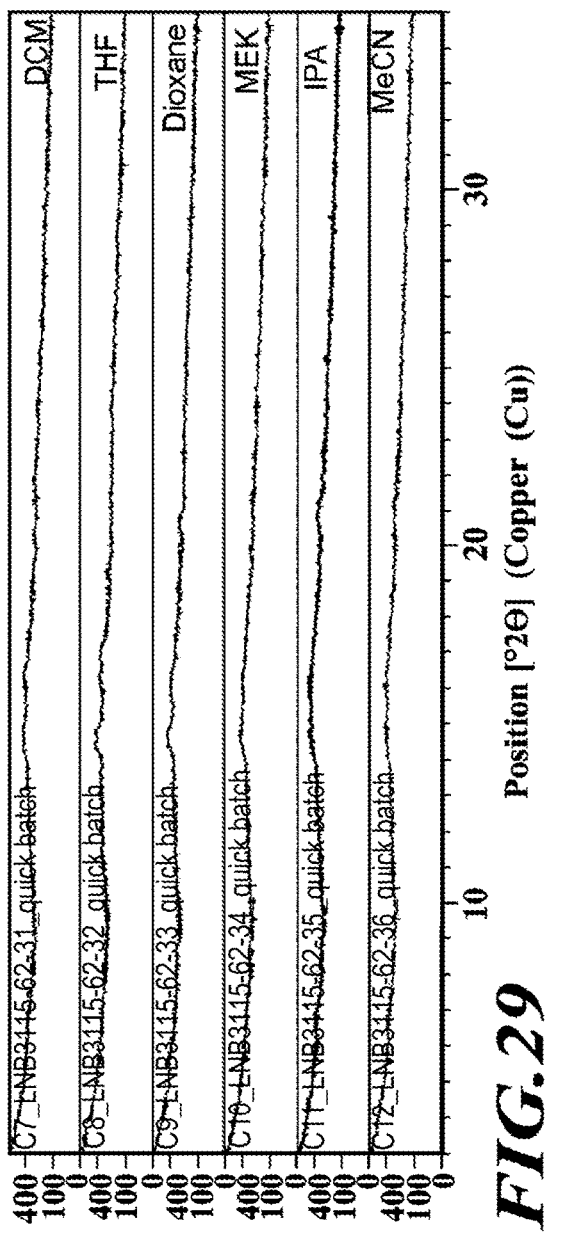
FIG. 29 shows XRPD diffractograms of the tert-butylamine salt.

Tert-Butylamine:

The tert-butylamine was pre-dissolved in methanol (333 mg in 1 mL) to form a stock solution, which was added (6.4 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solid was analyzed by XRPD (FIG. 29), which showed that only hints of crystallinity were seen, with no improvement with longer slurrying.

Figure 30:
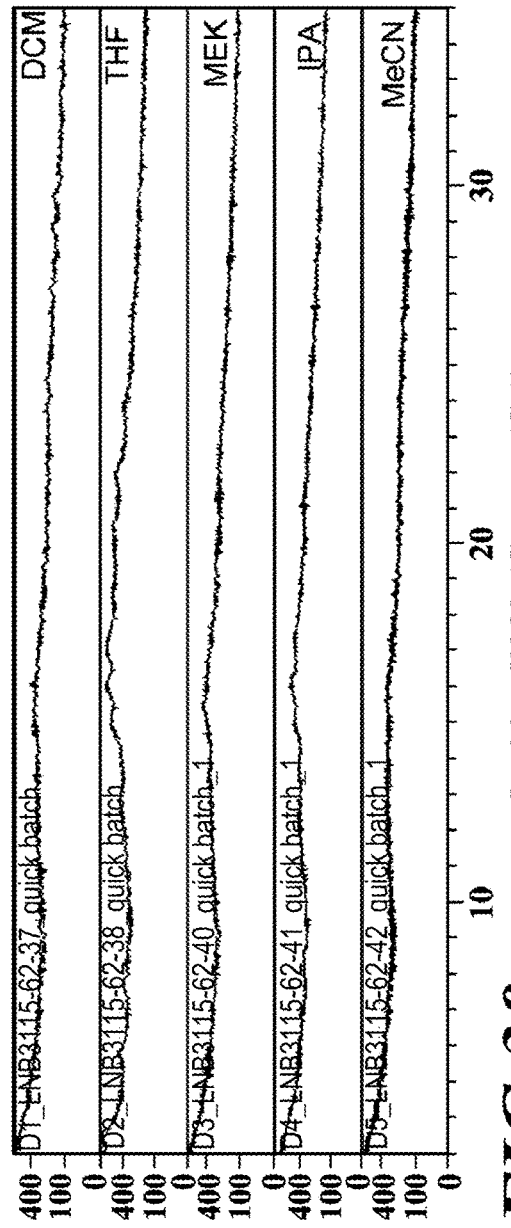
FIG. 30 shows XRPD diffractograms of the ammonium hydroxide salt.

Ammonium Hydroxide:

The ammonium hydroxide was added neat (4.2 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solid was analyzed by XRPD (FIG. 30), which showed that only hints of crystallinity were seen, with no improvement with longer slurrying.

Figure 31:
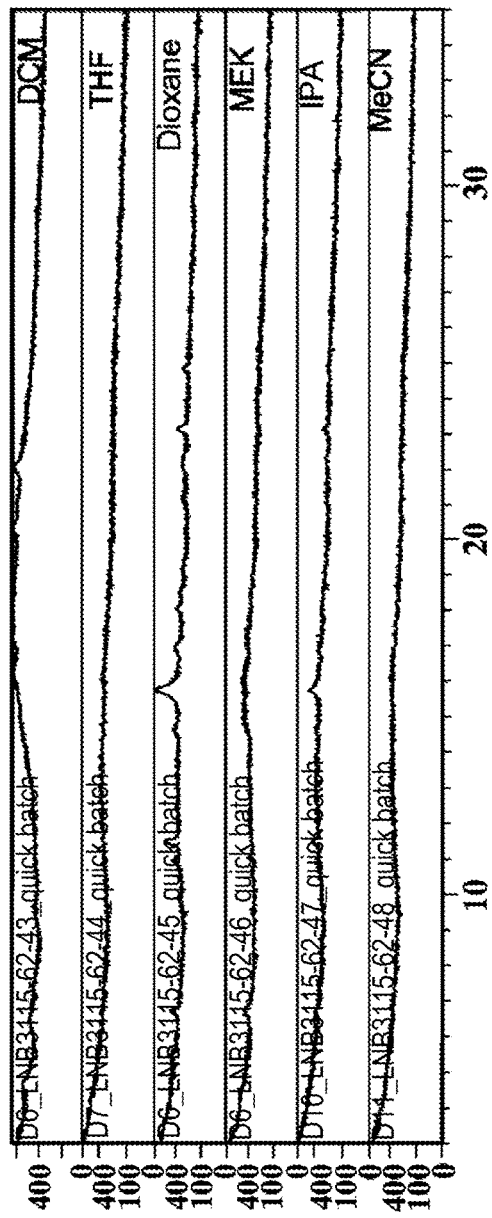
FIG. 31 shows XRPD diffractograms of the ethanolamine salt.

Ethanolamine:

The ethanolamine was pre-dissolved in methanol (512 mg in 1 mL) to form a stock solution, which was added (3.5 µL) to RP-101 (20 mgs in 1 mL of relevant solvent) which was dissolved or suspended, depending on solubility of system. The samples were held at 40° C. for 1 week to maximize the chance of salt formation (increase of kinetics and solubility of system). The resulting solid was analyzed by XRPD (FIG. 31), which showed that only hints of crystallinity were seen, with no improvement with longer slurrying.

Figure 32:
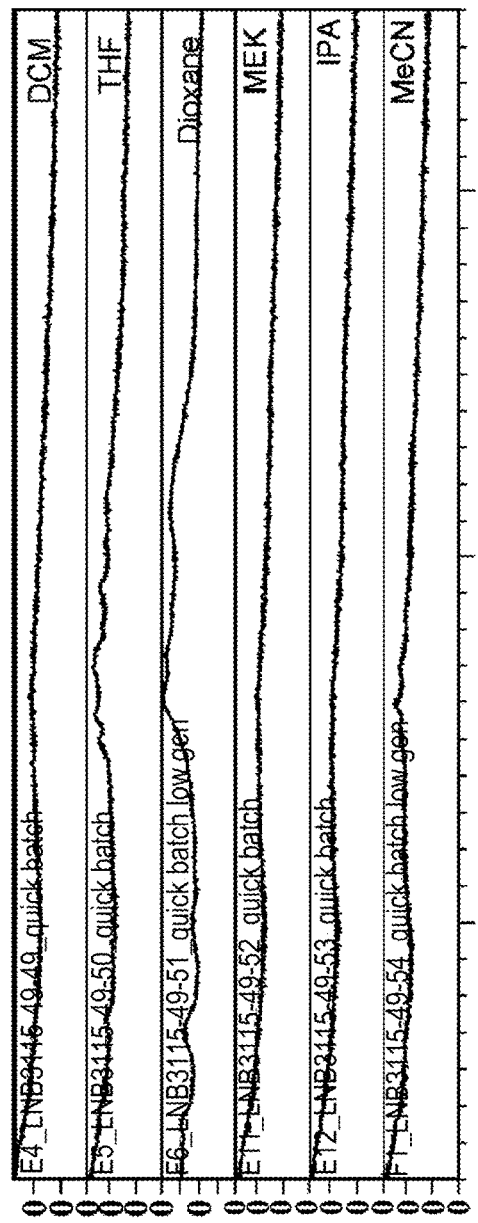
FIG. 32 shows XRPD diffractograms of the free acid.

Free Acid:

The free-acid was run as reference to provide a reference for the salt formation stage to determine if salts were being formed. The same procedure was followed as the salt formation, with the only exception being no counter-ion solution added. Analysis of the solids by XRPD (FIG. 32) showed that majority of the solids were amorphous. There were hints of crystallinity present although nothing that could be considered close to being partially crystalline. No improvement in crystallinity was seen with longer slurrying.

Summary:

Several of the salts tested exhibited some degree of crystallinity, and some with improvement in crystallinity upon longer slurrying times. The degree of crystallinity as assessed by XRPD and/or birefringence via PLM was used to identify potential candidates for further salt formation and crystallization studies. Salts that did not show clear birefringence and/or sharp peak characteristics via XRPD were not considered for further evaluation. In view of these results, additional experiments were performed (see Example 11) on five of the sixteen salt forms tested; namely, the dimethylaminoethanol, choline, diethylamine, benzathine and N-methylglucamine salt forms.

Example 11

Salt Screens

In the following experiments, additional tests were performed on the dimethylaminoethanol, choline, diethylamine, benzathine and N-methylglucamine salt forms of RP-101. As in the prior experiments, RP-101 as used in these experiments was the 1:1 diastereomeric mixture of the RP-103 and RP-104.

Figure 33:
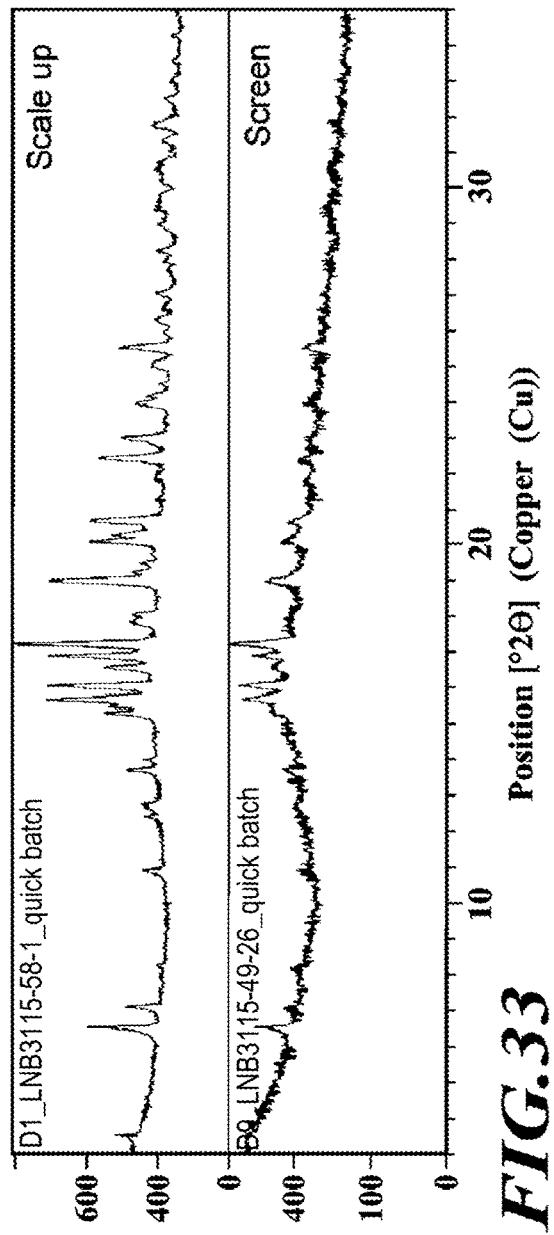
FIGS. 33 and 34 show XRPD diffractograms of the dimethylaminoethanol salt.

Dimethylaminoethanol:

The dimethylaminoethanol was pre-dissolved in methanol (423 mg in 0.5 mL) to form a stock solution, which was added (61.8 µL) to RP-101 (200 mgs in 10 mL of THF) which fully dissolved. The sample was held at 40° C. initially, where it was removed and allowed to stir at ambient temperature, while uncapped to allow THF to evaporate. After the weekend the THF had evaporated to dryness. To the white powder THF (5 mL) was added and a slurry was now formed. The solvent was again allowed to evaporate during the day, with temperature cycling employed overnight (40° C.—ambient—40° C.). The resulting solid was characterized by XRPD (FIG. 33), which clearly showed the presence of a highly crystalline solid.

Figure 34:
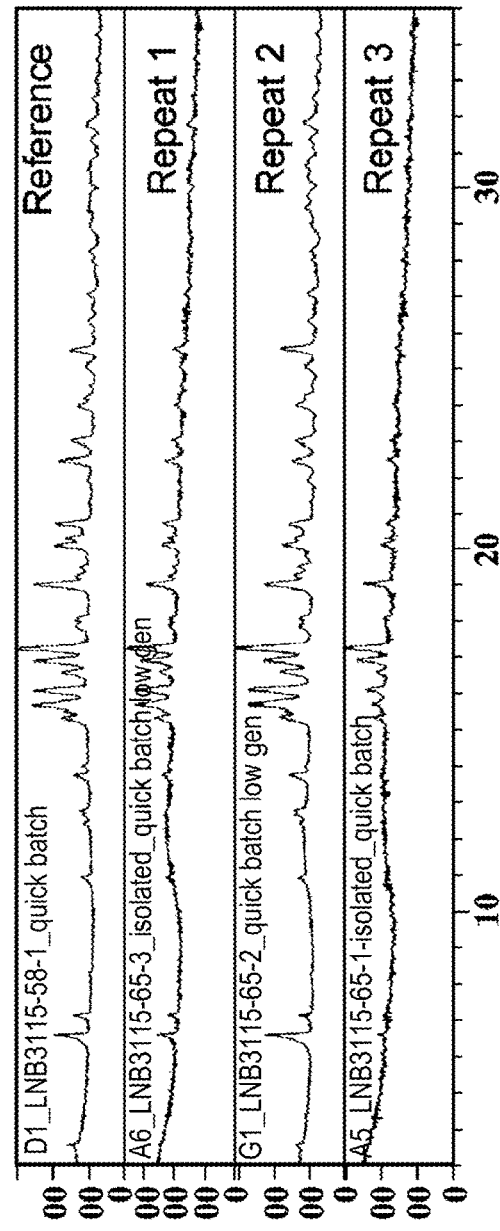

The process for making the crystalline solid was found to be robust with the same crystalline form being routinely produced (FIG. 34), and seeds have been used during the addition of dimethylaminoethanol to promote the crystallization process. On one occasion it was challenging to recover the solid material, even with seeding with crystals of deanol-RP-101 and evaporation of THF. On the addition of excess dimethylaminoethanol it was shown that the salt crystallized out. The issue was likely due the volatility of the dimethylaminoethanol which evaporated, thus making salt formation not possible. The sample has been routinely produced with excess amount of dimethylaminoethanol, where the counter ion was pre-dissolved in THF (to prevent potential degradation involving methanol) with the same crystalline form with comparable crystallinity produced.

Figure 35:
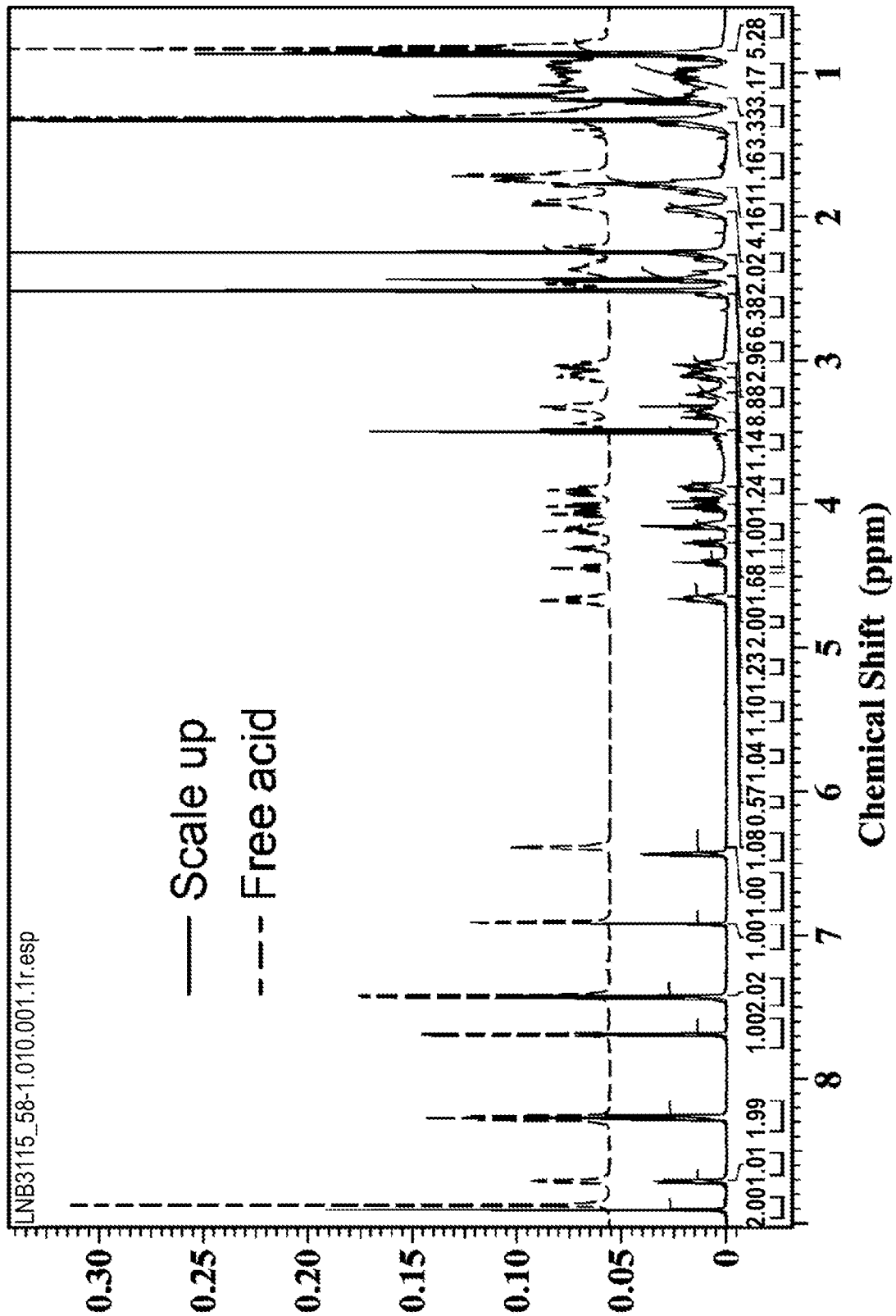
FIG. 35 shows the $^1$H-NMR of the dimethylaminoethanol salt.
Figure 36:
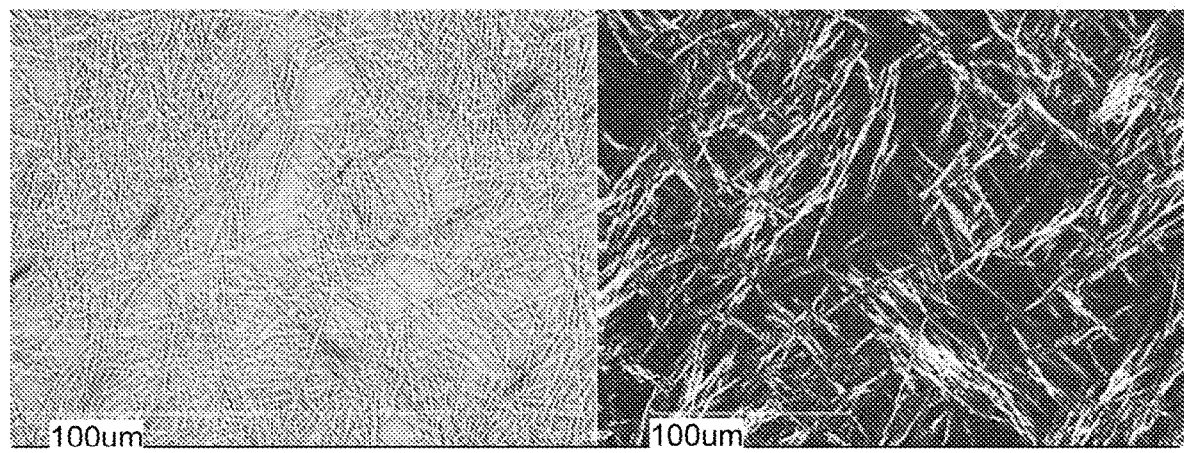
FIG. 36 shows PLM images of the dimethylaminoethanol salt.
Figure 37:
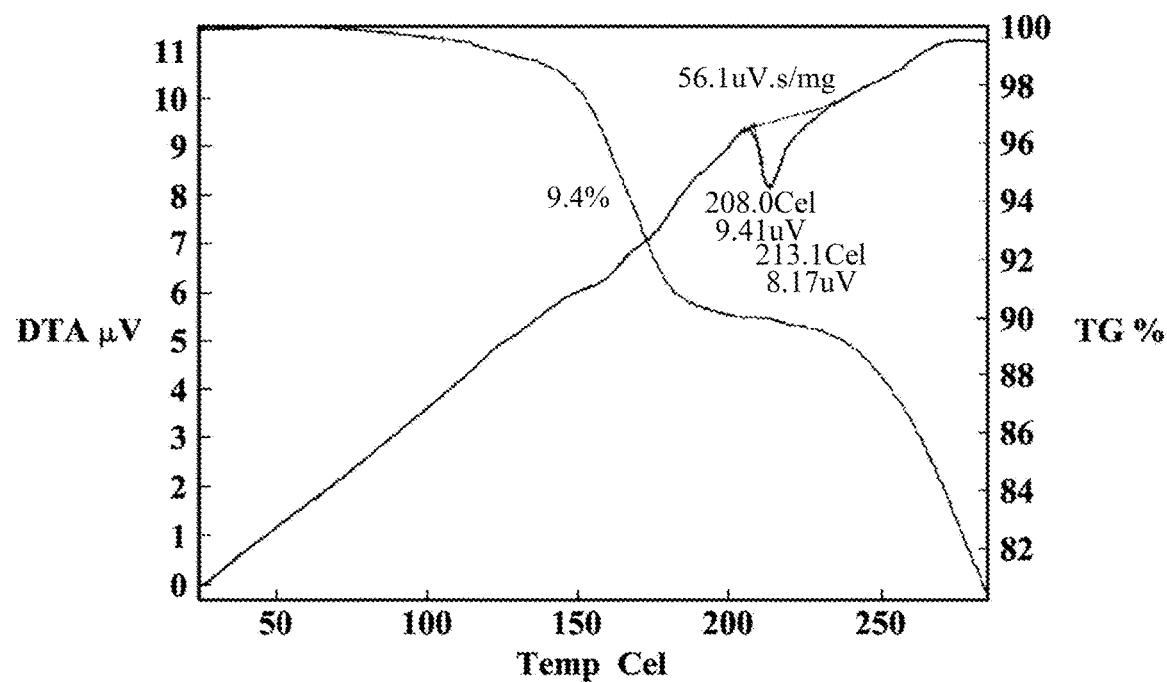
FIG. 37 shows a DTA thermogram of the dimethylaminoethanol salt.
Figure 38:
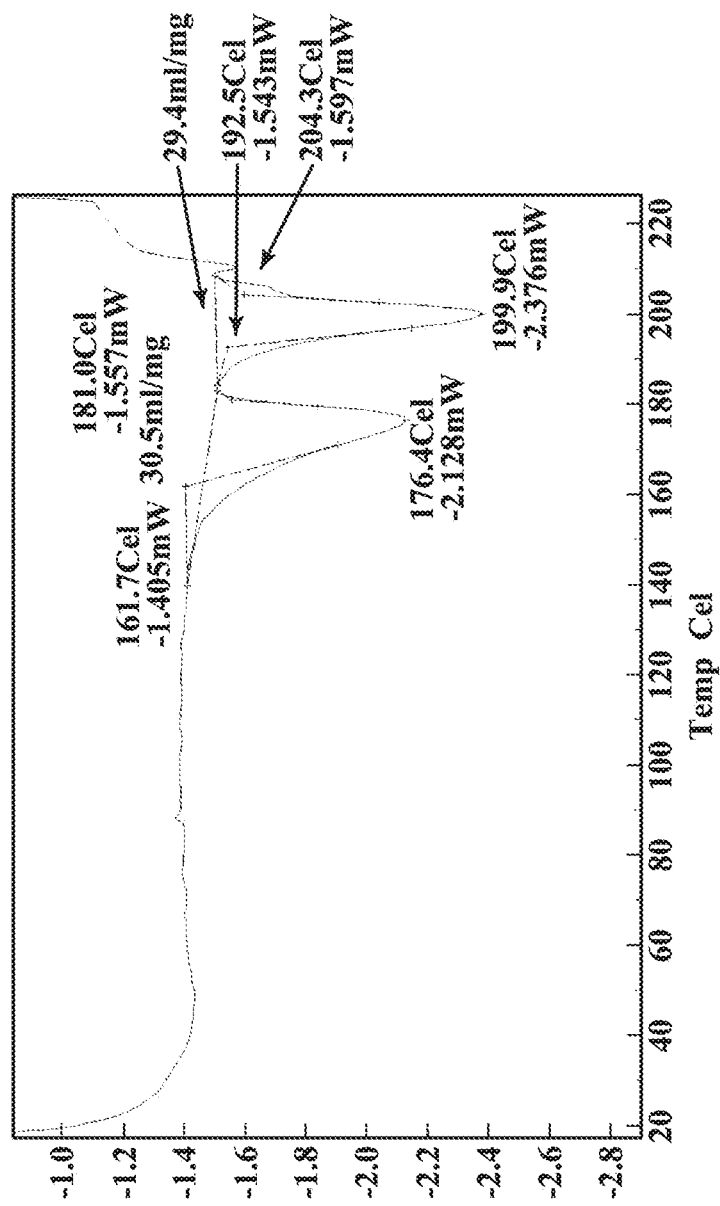
FIG. 38 shows a DSC thermogram of the dimethylaminoethanol salt.

The 1H NMR was performed on the crystalline solid (FIG. 35), which showed additional peaks relative to the free-acid. Along with some subtle chemical shifts it indicates that salt formation had occurred. The crystalline solid was characterized by PLM (FIG. 36), which clearly shows birefringence along with some potential needle morphology. The DTA (FIG. 37) shows a distinct mass loss (9.4%) at around 150° C., where a loss of one equivalent of dimethylaminoethanol equates to 11.5% by mass. The boiling point of dimethylaminoethanol is 133° C., which could correspond to the mass loss seen in the TGA. To help understanding the thermal properties, the sample was submitted for DSC (FIG. 38), which shows two clear thermal events present.

Figure 39:
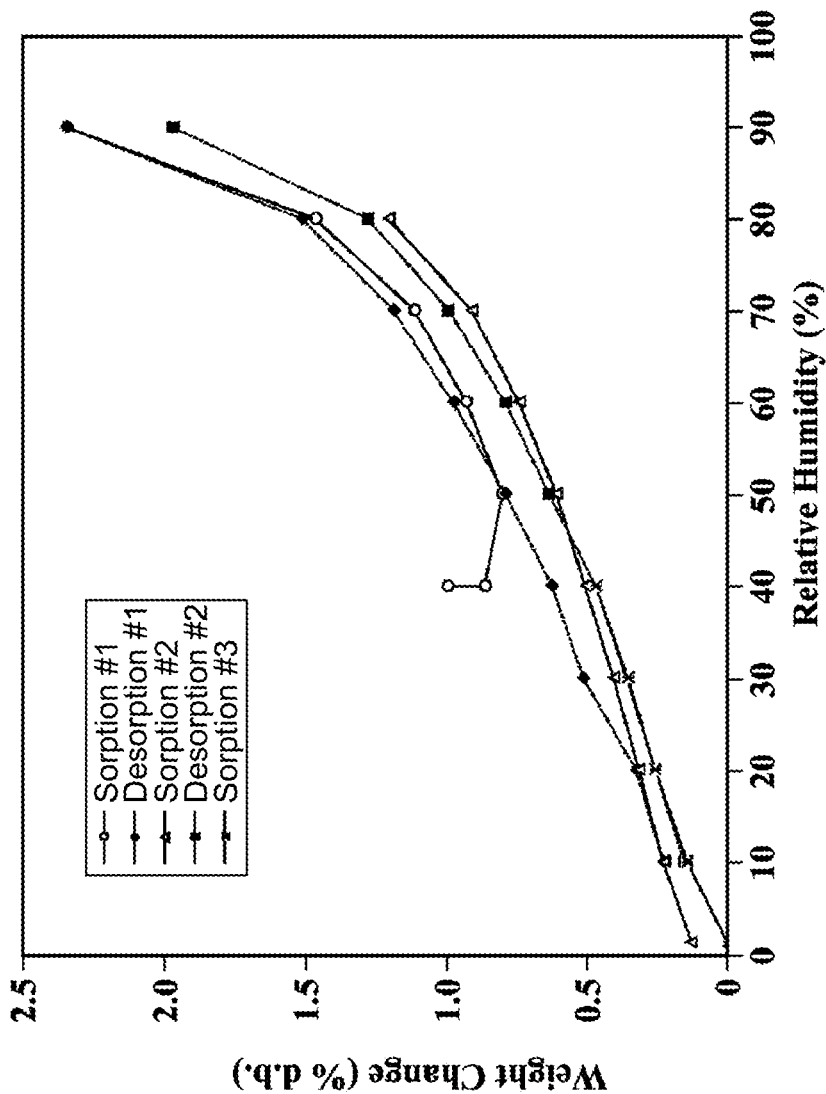
FIG. 39 shows a GVS profile of the dimethylaminoethanol salt.
Figure 40:
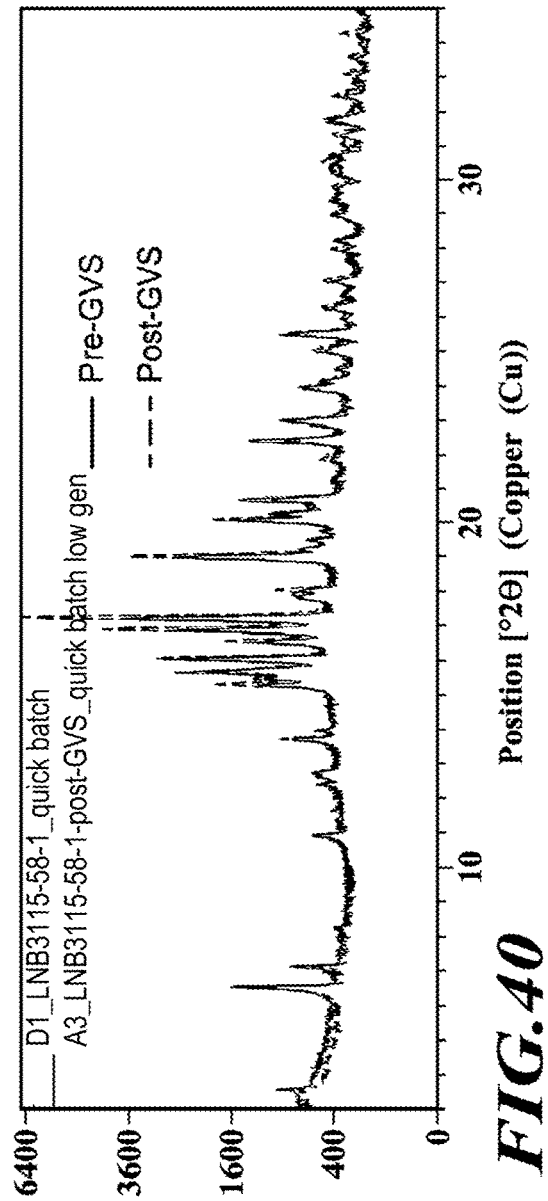
FIG. 40 shows XRPD diffractograms of the dimethylaminoethanol salt pre- and post-GVS profiling.

To determine the hygroscopicity of the dimethylaminoethanol salt the sample was submitted for DVS (FIG. 39). This showed that although there was an uptake in water seen, the process was reversible and did not indicate the conversion to a hydrate. The sample was also analyzed by XRPD post GVS (FIG. 40) and compared to the input material, with no change seen.

To understand the potential of forming hydrates the dimethylaminoethanol salt was slurried in a series of aqueous solvents, containing 10% by volume of water. The solvents selected are summarized in Table 9.

TABLE 9

Solvent to Water Ratios

| Solvent | Solvent/water ratio |
|---|---|
| Acetone | 90/10 (by volume) |
| Acetonitrile | 90/10 (by volume) |
| Methanol | 90/10 (by volume) |

Figure 41:
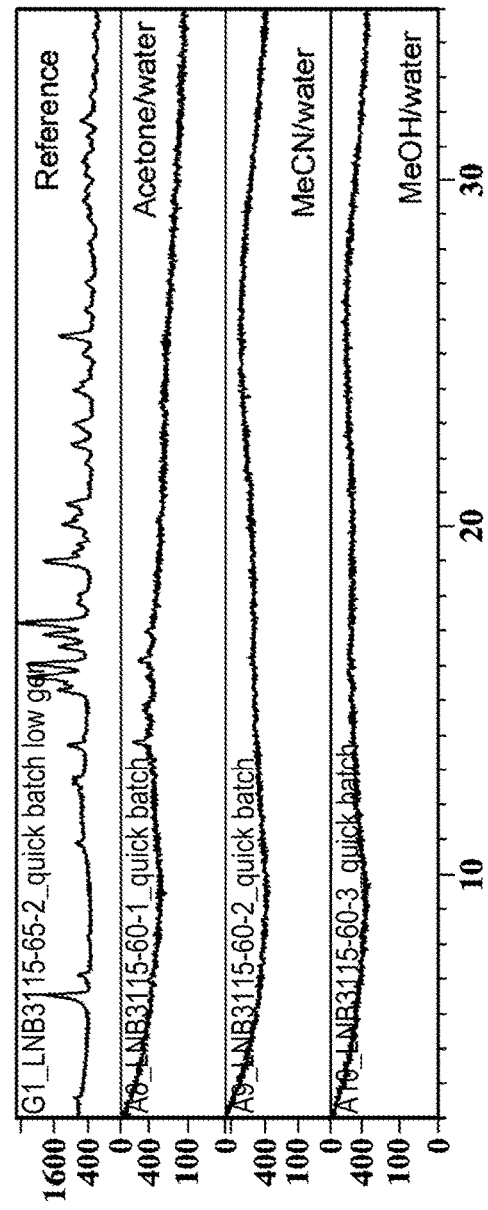
FIG. 41 shows XRPD diffractograms of the dimethylaminoethanol salt post hydration study.

When the solids were analyzed by XRPD post hydration study (FIG. 41), the majority of solids had been rendered amorphous. Only the acetone/water mixture had any signs of crystallinity, which corresponded to the input material. This indicates there is no obvious hydrate of the dimethylaminoethanol salt. The generation of amorphous material could be due to the high affinity of the molecule (RP-101) with solvents and water.

Figure 42:
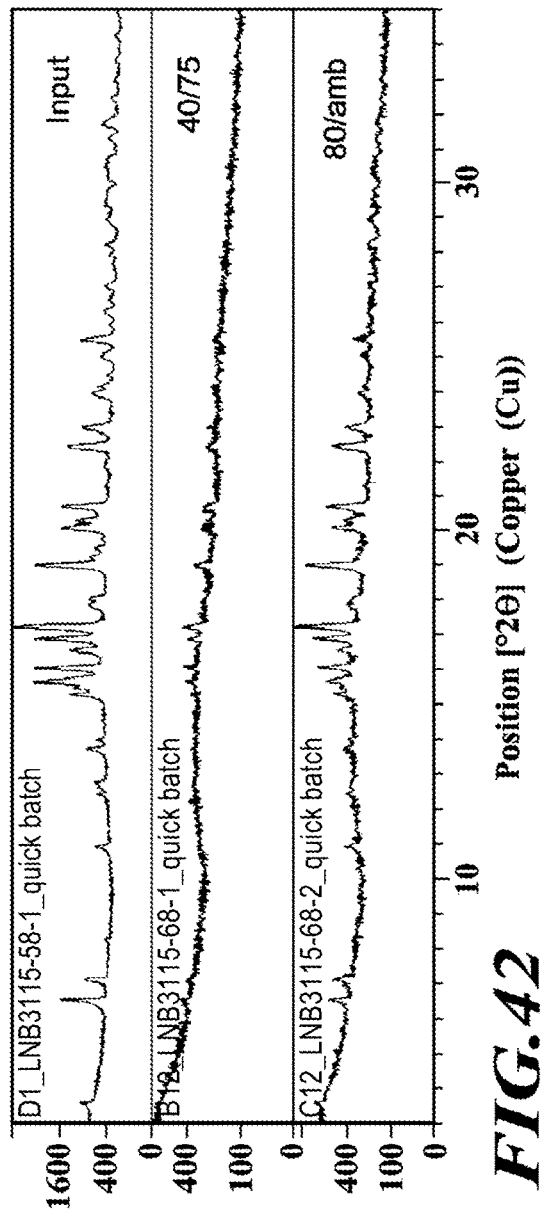
FIG. 42 shows XRPD diffractograms of the dimethylaminoethanol salt post stress testing.
Figure 43:
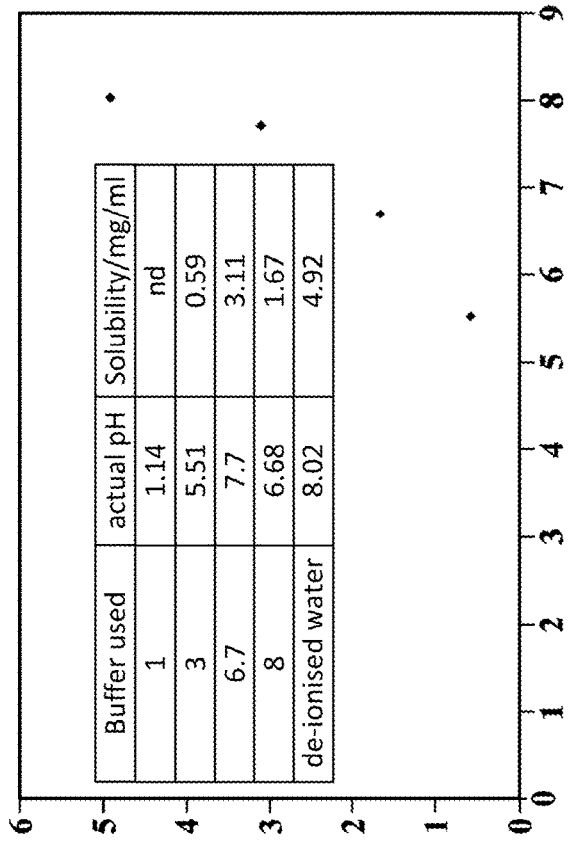
FIG. 43 shows a pH solubility curve for the dimethylaminoethanol salt.

To better understand the physical and chemical stability of the dimethylaminoethanol salt, the salt was placed under stressed condition (40° C./75% RH and 80° C./Ambient) for 1 week. The solids were then removed and analyzed via both XRPD and HPLC to determine physical and chemical stability, respectively. Analysis of the solids by XRPD post stability (FIG. 42) showed that in both cases the same crystalline form was present. There was a decrease in crystallinity seen for the 40/75 sample, although this could be linked to the high affinity with water for RP-101. The purity by HPLC showed to be essentially unchanged with purity of 97.3% and 96.8% for 40/75 and 80/ambient, respectively.

Figure 44:
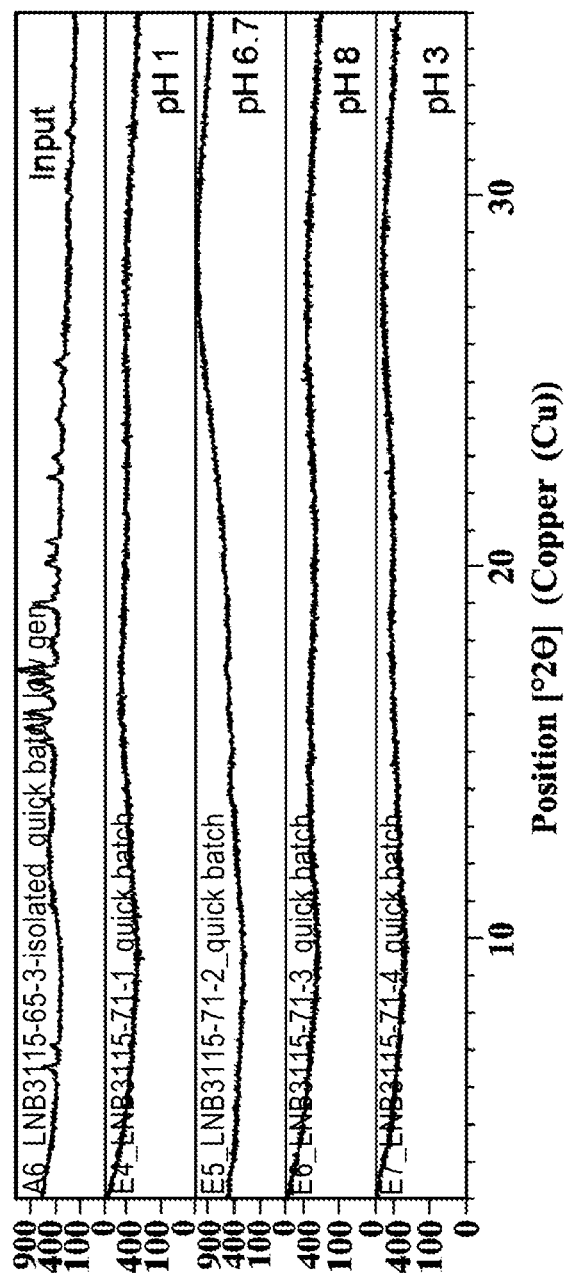
FIG. 44 shows XRPD diffractograms of the dimethylaminoethanol salt post solubility testing.

A range of buffers were made up (pH 1-pH 8) to understand the effect of pH on the measured solubility. In each case the pH is measured prior to isolation to ensure most accurate data. The pH solubility curve, including the tabulated data is shown in FIG. 44. The solubility is shown to be low for acidic conditions and rises significantly for basic conditions. Solubility in deionized water is shown to be relatively high. All solids were characterized by XRPD post solubility determination and shown all to be amorphous (FIG. 44), which is common when a solid is placed into aqueous conditions.

Benzathine:

The benzathine salt was scaled up for more a comprehensive characterization.

Attempt 1: The benzathine was pre-dissolved in methanol (453 mg in 0.5 mL) to form a stock solution, which was added (155.4 µL) to RP-101 (199 mgs in 10 mL of THF) which formed a clear solution. Sample was left to stir over the weekend at ambient with vial uncapped to allow solvent evaporation. On evaporation a brown oily substance was produced. The oil was re-dissolved in THF (5 mL), where a clear solution was formed. The solvent was allowed to evaporate, but prevented from going to dryness. As solvent evaporated a glassy solid was once again formed.

Attempt 2: The benzathine was pre-dissolved in methanol (453 mg in 0.5 mL) to form a stock solution, which was added (160 µL) to RP-101 (209 mgs in 10 mL of THF) which formed a clear solution. Sample was left to stir over the weekend at ambient with vial uncapped to allow solvent evaporation, which produced a significant amount of solid suspended in THF. Trying to isolate the solid by filtration under centrifuge proved problematic due to small particles present. As such slurry was centrifuged in 20 mL vial and solvent decanted off to leave voluminous white solid. Due to issues seen with initial benzathine salt attempt, the solid was allowed to dry at ambient conditions. As solvent evaporated the white voluminous solid slowly converted to brown sticky solid as seen in Attempt 1.

In short, difficulties were encountered with the salt formation stage for benzathine, particularly with regard to high solvent affinity. In the presence of solvent (THF) a stable solid is seen, but as the solvent evaporates, the solid converts to a less desirable sticky solid. The solid was briefly characterized to understand its suitability for development.

Figure 45:
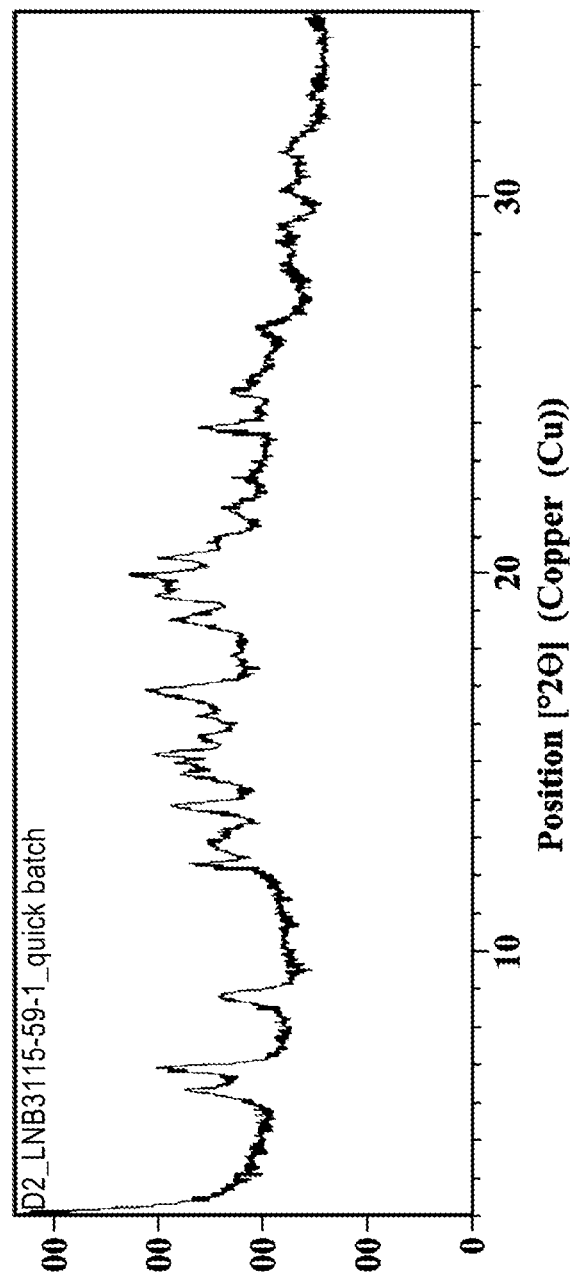
FIG. 45 shows an XRPD diffractogram of the benzathine salt.
Figure 46:
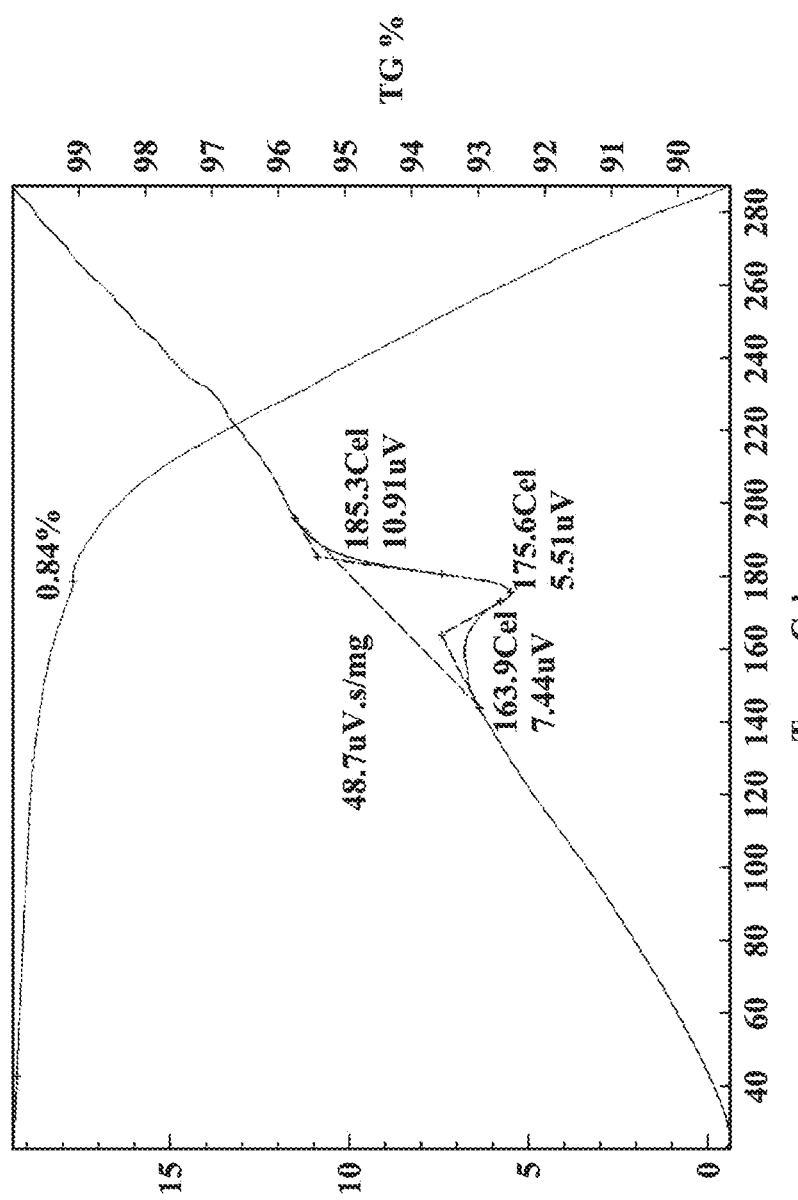
FIG. 46 shows a DTA thermogram of the benzathine salt.
Figure 47:
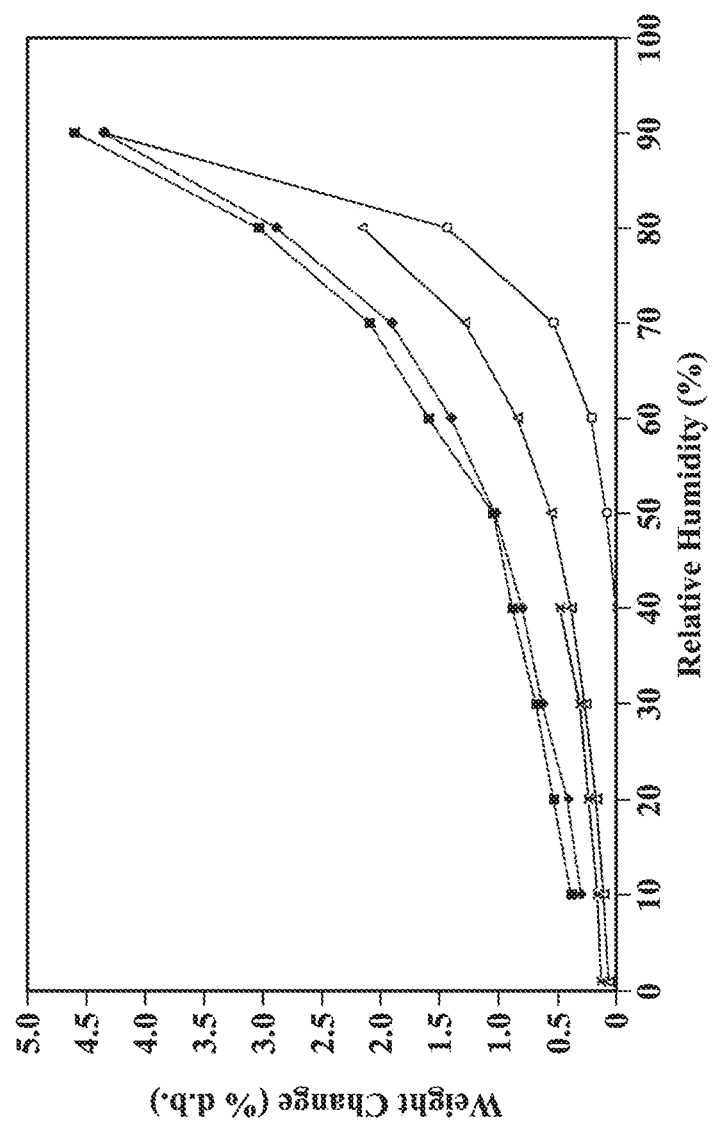
FIG. 47 shows a GVS profile of the benzathine salt.

To this end, the brown sticky solid was characterized by XRPD and it showed to be crystalline (FIG. 45), although considerably less than that of the dimethylaminoethanol salt. The benzathine salt was characterized by DTA (FIG. 46) which shows a single endothermic event in the DTA signal, which corresponded to a small mass loss (0.84%) in the TGA signal. The thermal event likely corresponds to the melt of the crystalline material. The hygroscopicity of the material was measured via GVS, which showed that the material was hygroscopic (FIG. 47), with an uptake of 4.5% at 90% RH seen. The profile indicates that there is no significant change in the solid (e.g. step changes), although there do appear to minor changes between first and second cycle. The solid post GVS was analyzed via XRPD (FIG. 48) and showed that the same crystalline form was present.

The physical properties of the benzathine salt are significantly less desirable than that of the dimethylaminoethanol salt; namely, isolation yielded a sticky partially crystalline solid; the hygroscopicity of the salt was higher than that of the dimethylaminoethanol salt; and the benzathine salt had a potentially higher affinity for solvent/water than dimethylaminoethanol salt, as shown by increase in crystallinity post GVS. Accordingly, further development of the benzathine salt was not pursued.

N-Methylglucamine:

The N-methylglucamine was pre-dissolved in 50/50 methanol/water (116 mg in 1 mL) to form a stock solution, which was added (492 µL) to RP-101 (202 mgs in 10 mL of MeCN) which formed a sticky solid and formed a ball like substance. When the system was heated to 40° C. the ball broke up and produced a milky suspension. The solid was characterized by XRPD and shown to be amorphous (FIG. 49). The sample was re-analyzed after slurrying at 40° C. for 1 week with the material still showing to be amorphous. Thus, further development of the N-methylglucamine was not pursued.

Figure 50:
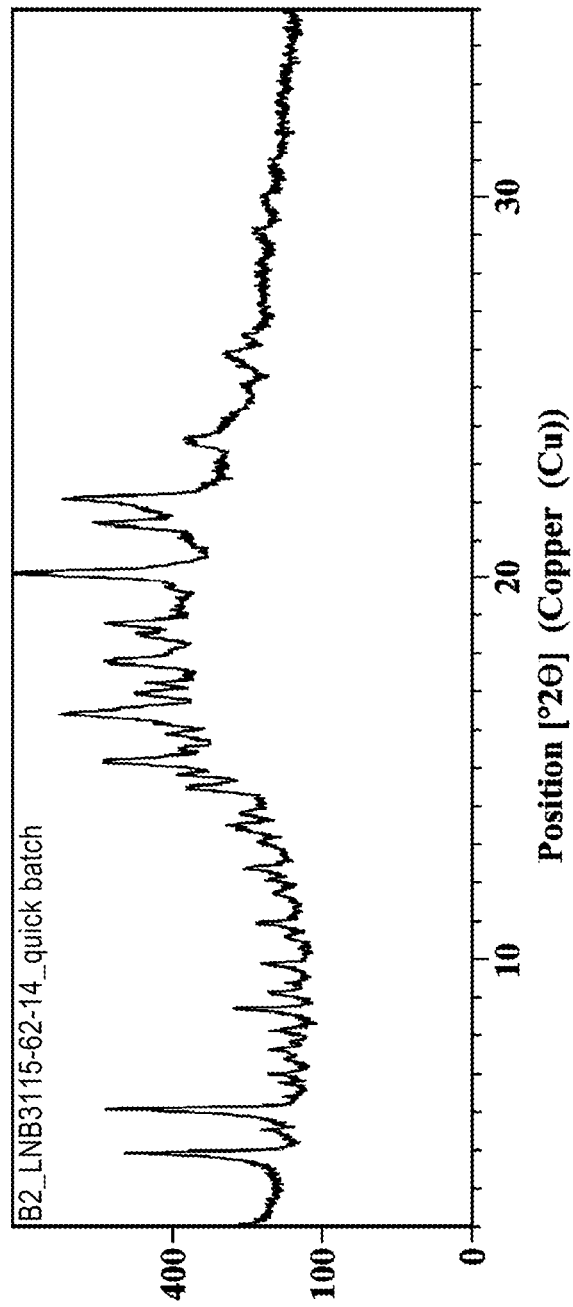
FIG. 50 shows an XRPD diffractogram of the choline hydroxide salt.
Figure 51:
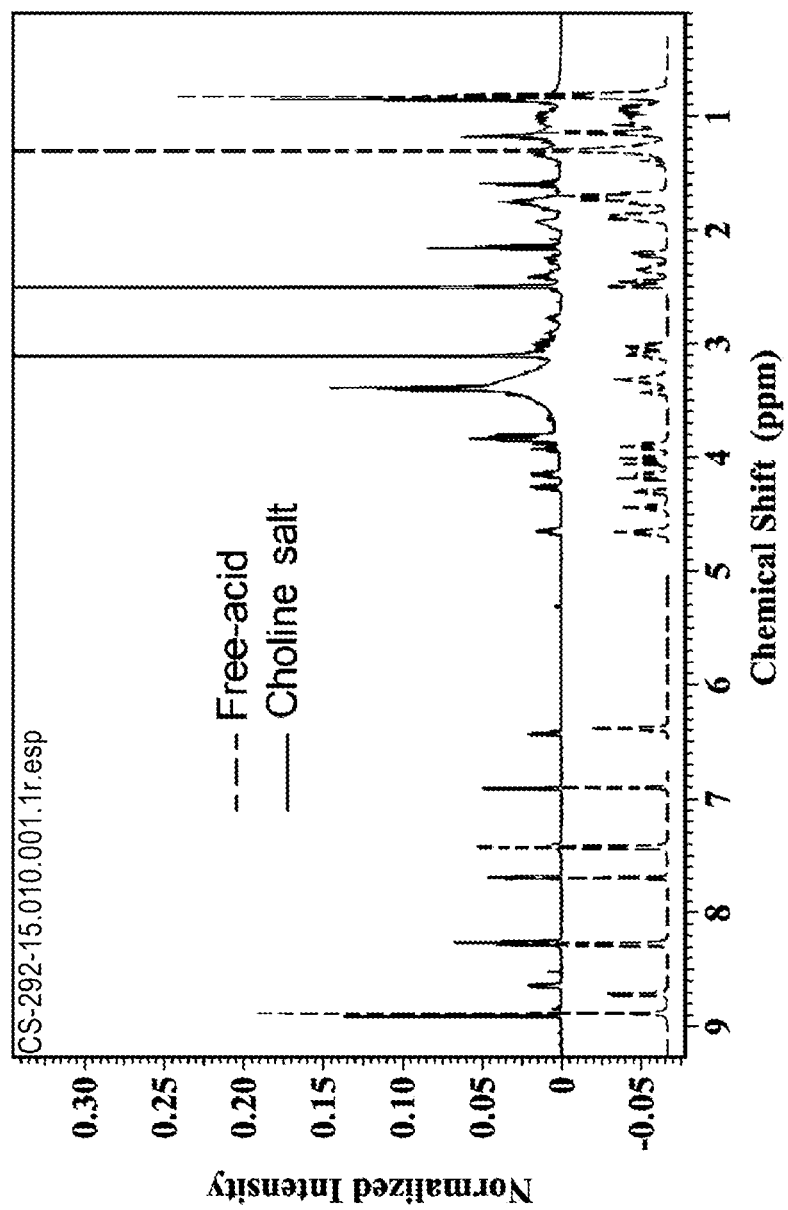
FIG. 51 shows the $^1$H-NMR of the choline hydroxide salt.

Choline Hydroxide:

The choline salt was shown to be significantly amorphous (partially crystalline) via XRPD (FIG. 50), the solid was submitted for $^1$H-NMR to determine if a salt has been formed (FIG. 51). The $^1$H-NMR was complex and inconclusive, although significant chemical shifts were seen (indicating salt formation has occurred). However, due to the amorphous nature of the choline salt, further development was not pursued.

Figure 52:
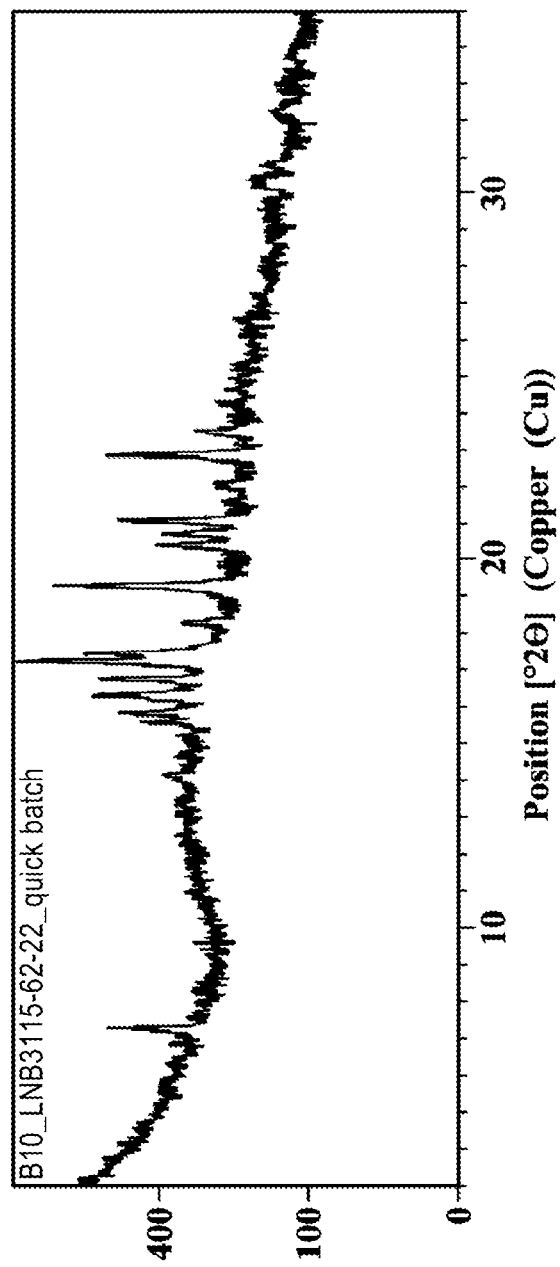
FIG. 52 shows an XRPD diffractogram of the diethylamine salt.
Figure 53:
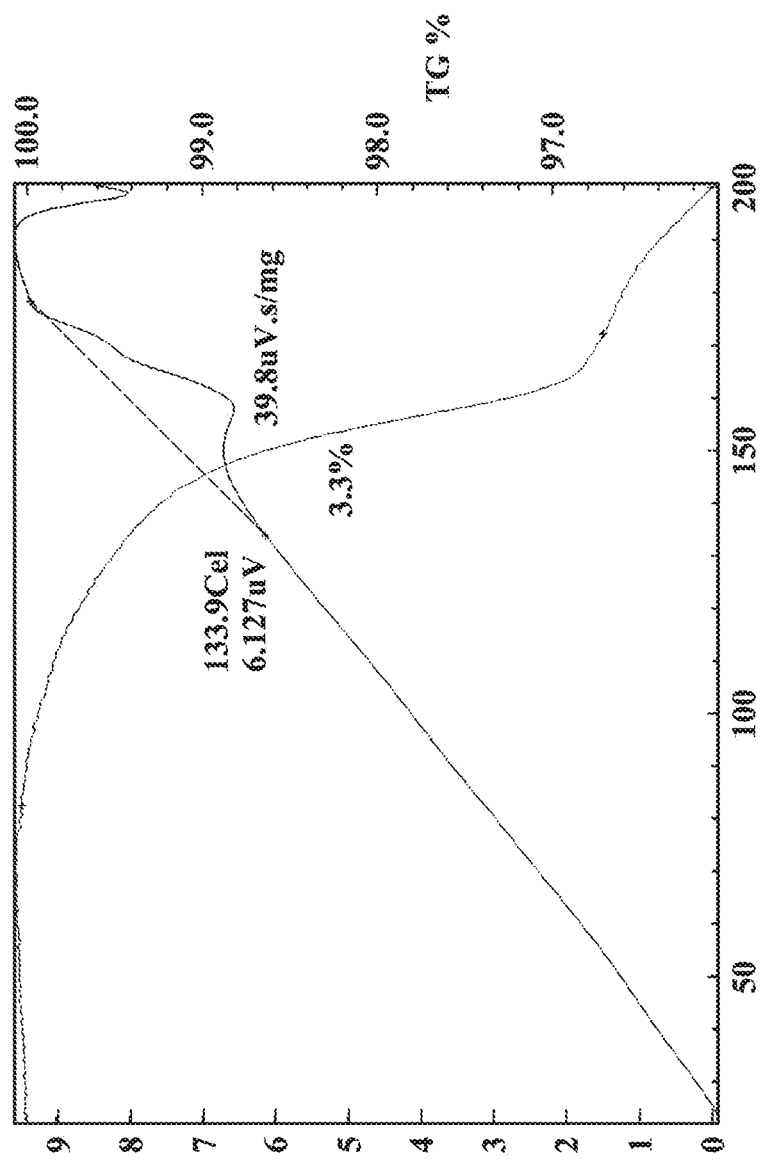
FIG. 53 shows a DTA thermogram of the diethylamine salt.
Figure 54:
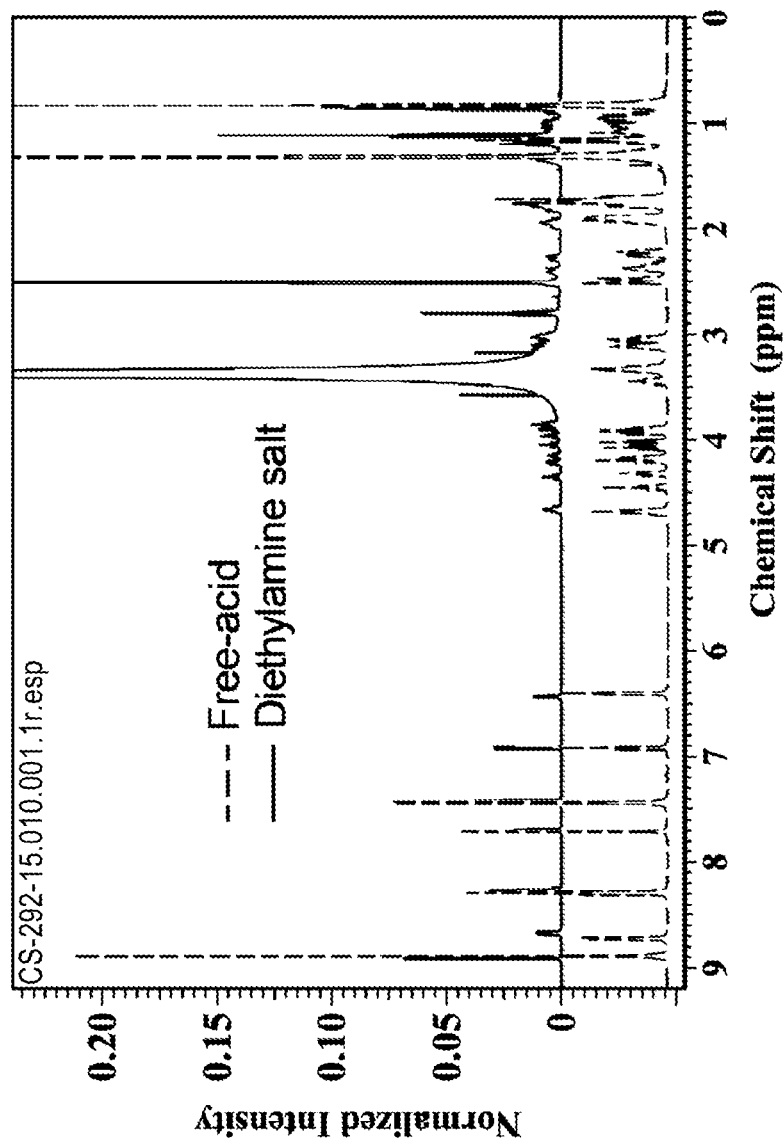
FIG. 54 shows the $^1$H-NMR of the diethylamine salt compared to the free acid.

Diethylamine:

The diethylamine salt is shown to be significantly amorphous (partially crystalline) via XRPD (FIG. 52), with more than one solvent system producing the same XRPD pattern. In the DTA signal (FIG. 53) a broad endothermic event was seen at 133° C., which corresponded to a 3.3% mass loss in the TGA. The solid was submitted for $^1$H-NMR to determine if a salt has been formed (FIG. 54). The $^1$H-NMR was complex and inconclusive, although significant chemical shifts were seen (indicating salt formation has occurred). However, due to the amorphous nature of the diethylamine salt, further development was not pursued.

Figure 55:
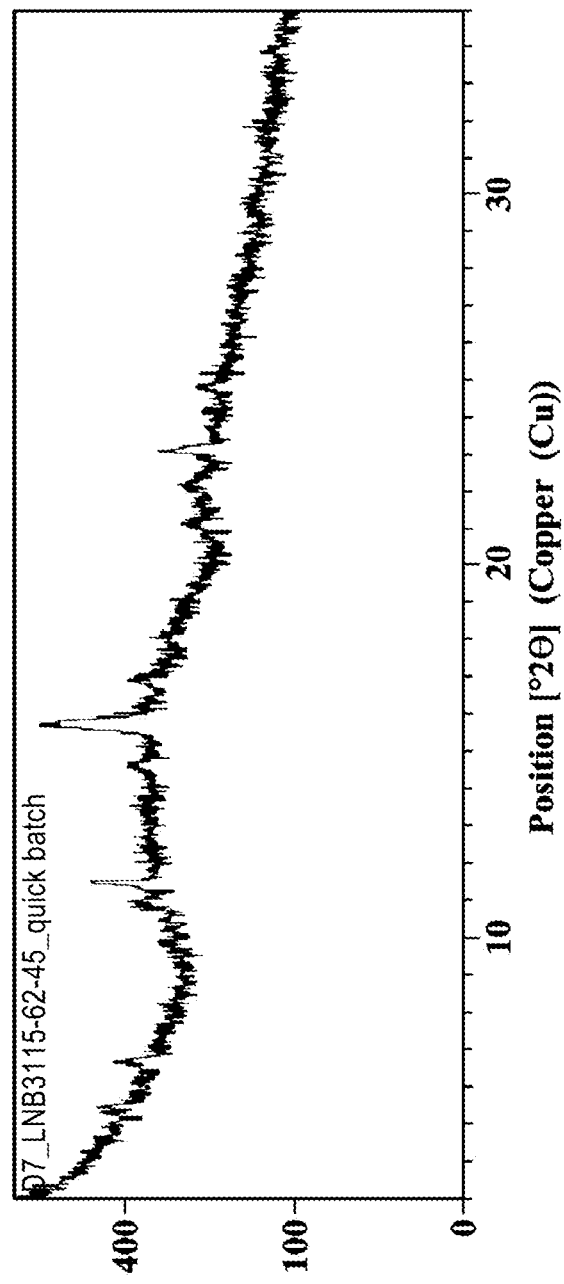
FIG. 55 shows an XRPD diffractogram of the ethanolamine salt.
Figure 56:
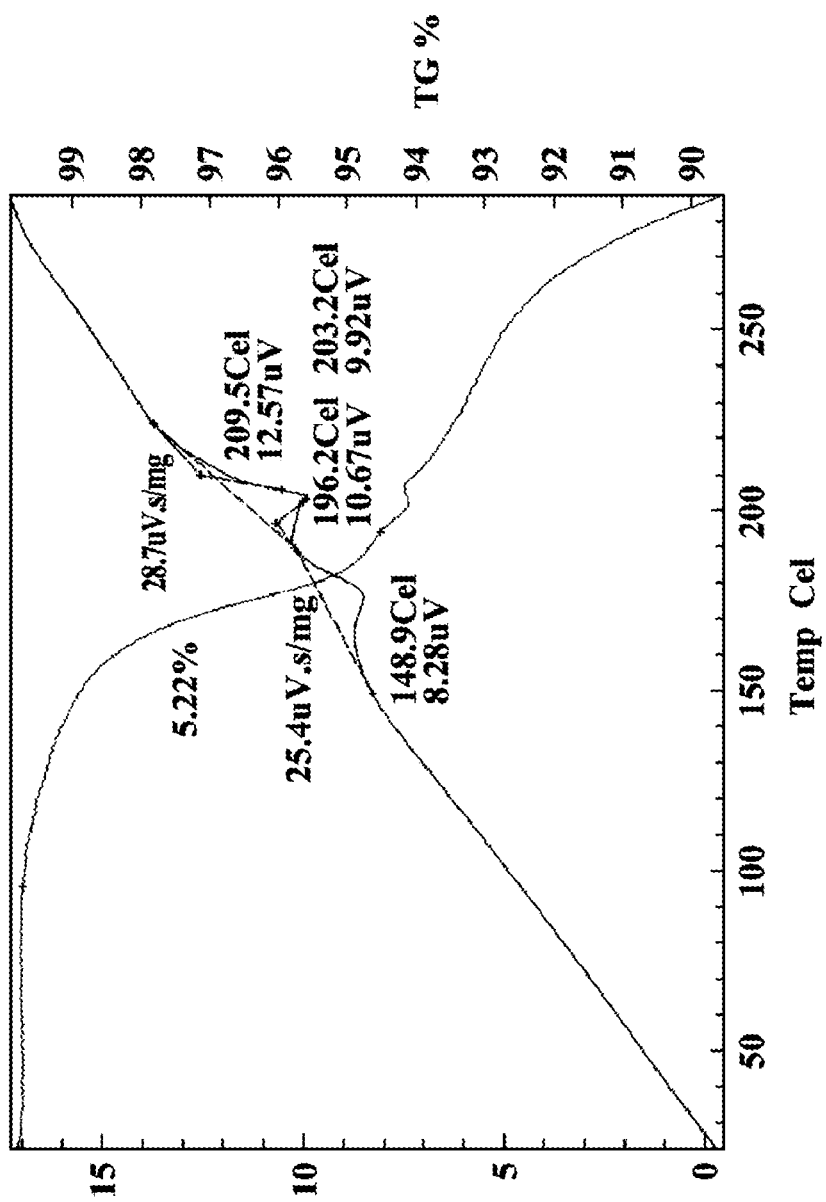
FIG. 56 shows a DTA thermogram of the ethanolamine salt.
Figure 57:
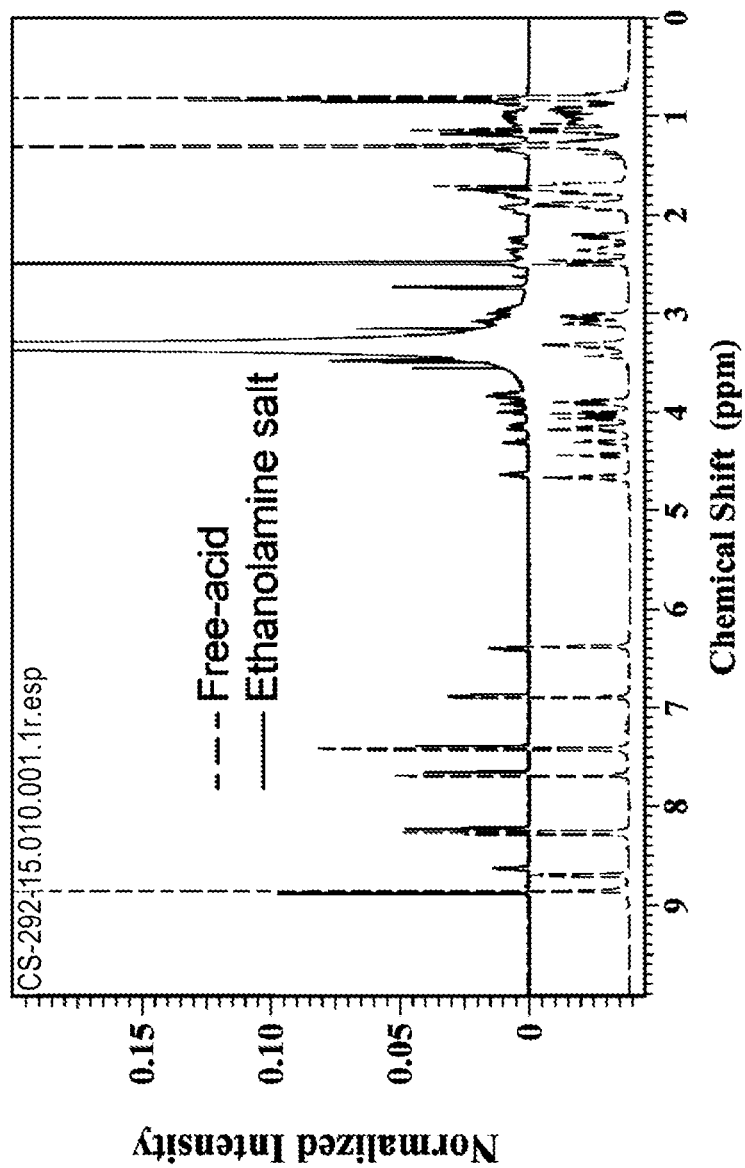
FIG. 57 shows the $^1$H-NMR of the ethanolamine salt compared to the free acid.

Ethanolamine:

The ethanolamine salt was found to be significantly amorphous (partially crystalline) from dioxane via XRPD (FIG. 55). In the DTA signal (FIG. 56) two broad endothermic events were seen at 149° C. and 203° C., which corresponded to a 5.2% mass loss in the TGA. The solid was submitted for $^1$H-NMR to determine if a salt has been formed (FIG. 57). The $^1$H-NMR was complex although significant chemical shifts were seen, indicating salt formation had occurred. However, due to the amorphous nature of the ethanolamine salt, further development was not pursued.

SUMMARY

In summary, the dimethylaminoethanol salt has surprisingly been found to possess superior crystallinity, solubility and/or thermal behavior compared to the other salts tested.

U.S. Provisional Patent Application No. 62/402,565, filed Sep. 30, 2016, to which the present application claims priority, is hereby incorporated herein by reference in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A compound having the following structure:

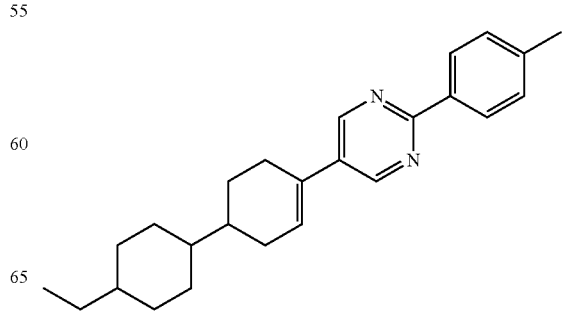

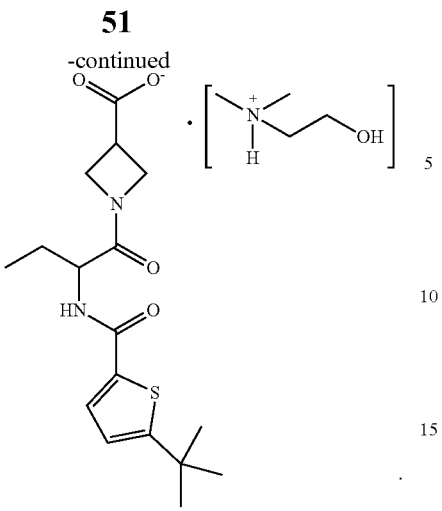
2. The compound of claim 1 having the following structure:
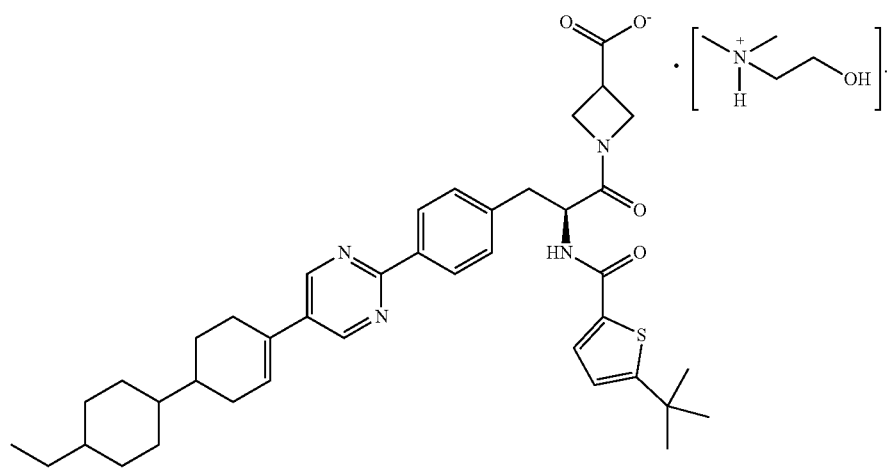
3. The compound of claim 1 having the following structure:
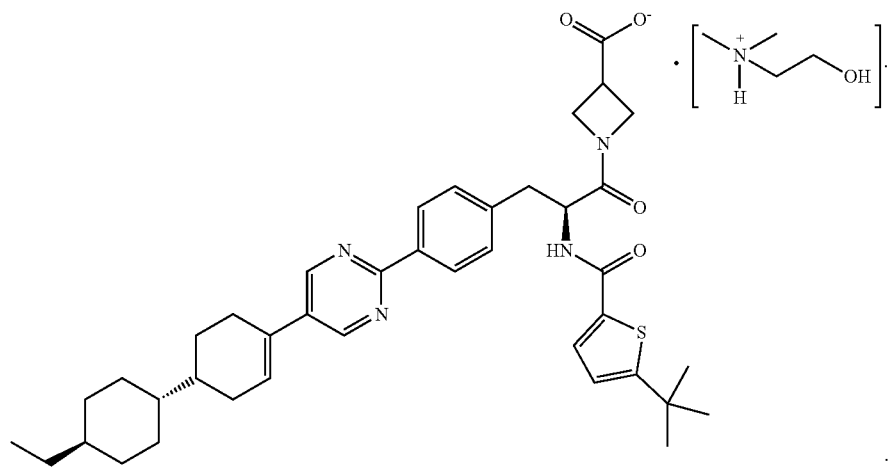
4. The compound of claim 1 having the following structure:

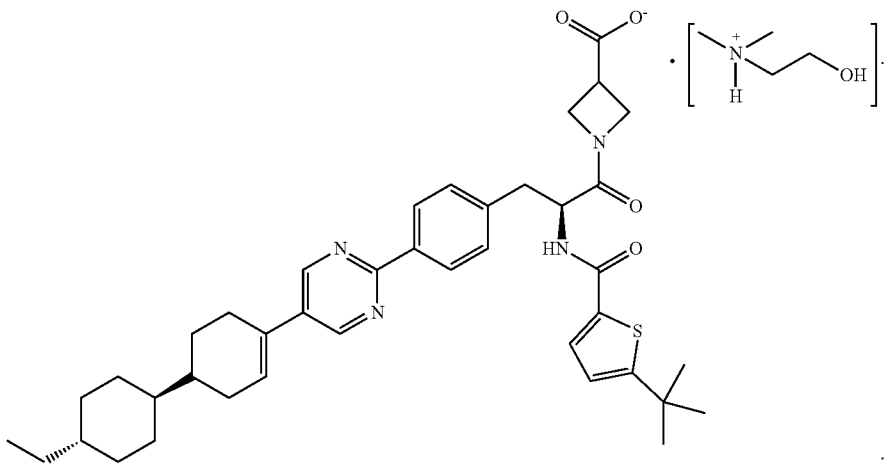

5. A racemic mixture of the compounds of claims 3 and 4.

6. Crystalline 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt.

7. Crystalline 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt having an XRPD pattern as shown in FIG. 1A.

8. Crystalline 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt having an XRPD pattern as shown in FIG. 2A.

9. Crystalline 2-hydroxy-N,N-dimethylethanaminium 1-(2-(5-(tert-butyl)-thiophene-2-carboxamido)-3-(4-(5-(4'-ethyl-[1,1'-bi(cyclohexan)]-3-en-4-yl)pyrimidin-2-yl)phenyl)propanoyl)azetidine-3-carboxylate salt having an XRPD pattern as shown in FIG. 3A.

10. Crystalline 2-hydroxy-N,N-dimethylethanaminium 1-(2-(5-(tert-butyl)-thiophene-2-carboxamido)-3-(4-(5-(4'-ethyl 1'-bi(cyclohexan)]-3-en-4-yl)pyrimidin-2-yl)phenyl) propanoyl)azetidine-3-carboxylate salt which exhibits an XRPD pattern having characteristic peaks expressed in distances (d-spacing) in degrees 2θ (+/−0.2° θ) as listed in Table 1A.

11. Crystalline 2-hydroxy-N,N-dimethylethanaminium 1-(2-(5-(tert-butyl)-thiophene-2-carboxamido)-3-(4-(5-(4'-ethyl 1'-bi(cyclohexan)]-3-en-4-yl)pyrimidin-2-yl)phenyl) propanoyl)azetidine-3-carboxylate salt which exhibits an XRPD pattern having characteristic peaks expressed in distances (d-spacing) in degrees 2θ (+/−0.2° θ) as listed in Table 1B.

12. Crystalline 2-hydroxy-N,N-dimethylethanaminium 1-(2-(5-(tert-butyl)-thiophene-2-carboxamido)-3-(4-(5-(4'-ethyl 1'-bi(cyclohexan)]-3-en-4-yl)pyrimidin-2-yl)phenyl) propanoyl)azetidine-3-carboxylate salt which exhibits an XRPD pattern having characteristic peaks expressed in distances (d-spacing) in degrees 2θ (+/−0.2° θ) as listed in Table 1C.

13. The compound of any one of claim 1, 2 or 6 having a purity in excess of 95% by weight.

14. The compound of any one of claim 1, 2 or 6 having a purity in excess of 98% by weight.

15. A pharmaceutical composition comprising a compound of any one of claim 1, 2 or 6 together with at least one pharmaceutically acceptable carrier, diluent or excipient.

16. A method of treating type II diabetes, comprising administering an effective amount of a compound of any one of claim 1, 2 or 6 to a patient at a frequency and for a duration of time sufficient to provide a beneficial effect to the patient.

* * * * *